US008173369B2

(12) United States Patent
Geschwind et al.

(10) Patent No.: US 8,173,369 B2
(45) Date of Patent: May 8, 2012

(54) PERIPHERAL GENE EXPRESSION BIOMARKERS FOR AUTISM

(75) Inventors: Daniel H. Geschwind, Santa Monica, CA (US); Yuhei Nishimura, Torrance, CA (US)

(73) Assignee: The Regents of the University of California, Oakland, CA (US)

( * ) Notice: Subject to any disclaimer, the term of this patent is extended or adjusted under 35 U.S.C. 154(b) by 343 days.

(21) Appl. No.: 12/467,115

(22) Filed: May 15, 2009

(65) Prior Publication Data

US 2010/0125042 A1 May 20, 2010

Related U.S. Application Data

(60) Provisional application No. 61/053,316, filed on May 15, 2008.

(51) Int. Cl.
*C12Q 1/68* (2006.01)
*G01N 33/53* (2006.01)

(52) U.S. Cl. ........................ 435/6.11; 435/6.12; 435/7.1

(58) Field of Classification Search ........................ None
See application file for complete search history.

(56) References Cited

FOREIGN PATENT DOCUMENTS

WO WO-2008021290 A2 * 2/2008

OTHER PUBLICATIONS

Abrahams, B. et al., "Advances in autism genetics: on the threshold of a new neurobiology," Nat. Rev. Genet. 9(5):341-355, 2008.
Alarcon, M. et al., "Evidence for a language quantitative trait locus on chromosome 7q in multiplex autism families," Am. J. Hum. Genet. 70(1):60-71, 2002.
Alarcon, M. et al., "Quantitative genome scan and ordered-subsets analysis of autism endophenotypes support language QTLs," Mol. Psychiatry 10(8):747-757, 2005.
Allen-Brady, K. et al., "A high-density SNP genome-wide linkage scan in a large autism extended pedigree," Mol. Psychiatry 14, 590-600, Feb. 19, 2008.
Auranen, M. et al., "A genomewide screen for autism-spectrum disorders: evidence for a major susceptibility locus on chromosome 3q25-27," Am. J. Hum. Genet. 71(4):777-790, 2002.
Baron, C. et al., "Genomic and functional profiling of duplicated chromosome 15 cell lines reveal regulatory alternations in UBE3A-associated ubiquitin-proteasome pathway processes," Hum. Mol. Genet., 15, 853-869, 2006.
Barrett, S. et al., "An autosomal genomic screen for autism," Am. J. Med. Genet. 88(6):609-615, 1999.
Belmonte, M. et al,. "Autism as a disorder of neural information processing: directions for research and targets for therapy," Mol. Psychiatry, 9, 646-663, 2004.
Belmonte, M. et al., "Fragile X syndrome and autism at the intersection of genetic and neural networks," Nat. Neurosci. 9(10):1221-1225, 2006.
Buxbaum, J. et al., "Evidence for susceptibility gene for autism on chromosome 2 and for genetic heterogeneity," Am. J. Hum. Genet. 68(6):1514-1520, 2001.
Cantor, R. et al., "Replication of autism linkage: fine-mapping peak at 17q21," Am. J. Hum. Genet. 76(6):1050-1056, 2005.
Duvall, J. et al., "A quantitative trait locus analysis of social responsiveness in multiplex autism families," Am. J. Psychiatry 164(4):656-662, 2007.
Folstein, S. et al., "Genetics of autism: Complex aetiology for a heterogeneous disorder," Nat. Rev. Genet. 2, 943-955, 2001.
Geschwind, D., "Autism: Many genes, common pathways?,"Cell 135(3)391-395, 2008.
Geschwind, D. et al., "Autism spectrum disorders: Developmental disconnection syndromes," Curr. Opin. Neurobiol. 17(1):103-111, 2007.
Geschwind, D., "DNA microarrays: Translation of the genome from laboratory to clinic," The Lancet Nuerol., 2, 275-282, 2003.
Geschwind, D., "Family connections," Nature 454(7206):838-839, 2008.
Herzing, L. et al., "Allele-specific expression analysis by RNA-FISH demonstrates preferential maternal expression of UBE3A and imprint maintenance within 15q11-q13 duplications," Hum. Mol. Genet., 11, 1707-1718, 2002.
Herzing, L. et al., "The human aminophospholipid-transporting ATPase gene ATP10C maps adjacent to UBE3A and exhibits similar imprinted expression," Am. J. Hum. Genet. 68:1501-1505, 2001.
Kakinuma, H. et al., "Variation in GABA-A subunit gene copy number in an autistic patient with mosaic 4 p duplications (p12p16)," Am. J. Med. Genet. B Neuroopsychiatr. Genet. 147B:973-975, 2008.
Liu, J. et al., "A genomewide screen for autism susceptibility Loci," Am. J. Hum Genet. 69(2):327-340, 2001.
Marshall, C. et al., "Structural variation of chromosomes in autism spectrum disorder," Am. J. Hum Genet. 82(2):477-488, 2008.
Mirnics, K. et al., "Critical appraisal of DNA microarrays in psychiatric genomics," Biol. Psychiatry 60:163-176, 2006.
Muhle, R. et al., "The genetics of autism," Pediatrics 113(5):472-286, 2004.
Nishimura, Y. et al., "Genome-wide expression profiling of lymphoblastoid cell lines distinguishes different forms of autism and reveals shared pathways," Hum. Mol. Genet. 16(14):1682-1698, 2007.
Schellenberg, G. et al., "Evidence for multiple loci from a genome scan of autism kindreds," Mol. Psychiatry 11(11)1049-1060, 2006.
Sebat, J. et al., "Strong association of de novo copy number mutations with autism," Science 316:445-449, 2007.
Sutcliffe, J. et al., "Genetics of childhood disorders: XLVII. Autism, part 6: Duplication and inherited susceptibility of chromosome 15q11-q13 genes in autism," J. Am. Acad. Child Adolesc. Psychiatry 42:253-256, 2003.
Szatmari, P. et al., "Mapping autism risk loci using genetic linkage and chromosomal rearrangements," Nat. Genet. 39(3):319-328, 2007.
Tang, Y. et al., "Blood expression profiles for tuberous sclerosis complex 2, neurofibromatosis type 1, and down's syndrome," Ann. Neurol. 56, 808-814, 2004.

(Continued)

*Primary Examiner* — James Martinell
(74) *Attorney, Agent, or Firm* — Gates & Cooper LLP

(57) ABSTRACT

The disclosed invention comprises methods and materials for screening cells for genetic profiles associated with autism spectrum disorders. The methods typically involve isolating a cell from an individual and then observing the expression profile of one or more genes in the cell, wherein certain expression patterns of the genes observed are associated with autism spectrum disorders.

17 Claims, 15 Drawing Sheets

OTHER PUBLICATIONS

Thomas, N. et al., "Estimate of the prevalence of chromosomes 15q11-q13 duplications," Am. J. Med. Genet. 120A:596-598, 2003.

Trikalinos, T. et al., "A heterogeneity-based genome search meta-analysis for autism-spectrum disorders," Mol. Psychiatry 11(1):29-36, 2006.

Veenstra-Vanderweele, J. et al., "Autism as a paradigmatic complex genetic disorder," Ann. Rev. Genomics Hum. Genet. 5:379-405, 2004.

Wang, N. et al., "High-resolution molecular characterization of 15q11-q13 rearrangements by array comparative genomic hybridization (array CGH) with detection of gene dosage," Am. J. Hum. Genet. 75:267-281, 2004.

Wiedmer-Mikhail, E. et al., "Chromosomes in autism and related pervasive developmental disorders: a cytogenetic study," J. Intellect. Disabil. Res. 42(Part 1):8-12, 1998.

Yonan, A. et al., "A genomewide screen of 345 families for autism-susceptibility loci," Am. J. Hum. Genet. 73:886-897, 2003.

* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1

ggggaagcat gtcgaagaaa                                                  20


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

ggccttgagc tccgaaatgt                                                  20


<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3

ggagcctttg ggggtttatt                                                  20


<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4

ccatcctcca tcaggcactt                                                  20


<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5

agccgaaaac accctgcaat c                                                21
```

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ctggatttcc tcttcgtgga gtt 23

<210> SEQ ID NO 7
<211> LENGTH: 2310
<212> TYPE: DNA
<213> ORGANISM: Homo sapiens

<400> SEQUENCE: 7
gggggctgcg ctcgctacgt ccgctgctgc tgcccggctc gggcctgagc gccgagcagg 60
atcccaagtg atggtggttt cctcggaggg cgagctgagt actgcgcgac tggttagcac 120
ggtggagctg gtagccacgc ctgctggctg gcgtgcgtga acaggtgtgg accgcaggat 180
ctcagcactc tgacccaagg ggaagcatgt cgaagaaagg ccggagcaag ggcgagaagc 240
ccgagatgga gacggacgcg gtgcagatgg ccaacgagga gctgcgggcc aagctgacca 300
gcattcagat cgagttccag caggaaaaaa gcaaggtggg caaactgcgc gagcggctgc 360
aggaggcgaa gctggagcgc gagcaggagc agcgacggca cacggcctac atttcggagc 420
tcaaggccaa gctgcatgag gagaagacca aggagctgca ggcgctgcgc gaggggctca 480
tccggcagca cgagcaggag gcggcgcgca ccgccaagat caaggagggc gagctgcagc 540
ggctacaggc cacgctgaac gtgctgcgcg acggcgcggc cgacaaggtc aagacggcgc 600
tgctgaccga ggcgcgcgag gaggcgcgca gggccttcga tggagagcgc ctgcggctgc 660
agcaggagat cctggagctc aaggcagcgc gcaatcaggc agaggaggcg ctcagtaact 720
gcatgcaggc cgacaagacc aaggcagccg acctgcgtgc cgcctaccag gcgcaccaag 780
acgaggtgca ccgcatcaag cgcgagtgcg agcgcgacat ccgcaggctg atggatgaga 840
tcaaagggaa agaccgtgtg attctggcct tggagaagga acttggcgtg caggctgggc 900
agacccagaa gctgcttctg cagaaagagg ctttggatga gcagctggtt caggtcaagg 960
aggccgagcg gcaccacagt agtccaaaga gagagctccc gcccgggatc ggggacatgg 1020
tggagctcat gggcgtccag gatcaacata tggacgagcg agatgtgagg cgatttcaac 1080
taaaaattgc tgaactgaat tcagtgatac ggaagctgga agacagaaat acgctgttgg 1140
cagatgagag gaatgaactg ctgaaacgct cacgagagac cgaggttcag ctgaagcccc 1200
tggtggagaa gaacaagcgg atgaacaaga agaatgagga tctgttgcag agtatccaga 1260
ggatggagga gaaaatcaag aacctcacgc gggaaaacgt ggaaatgaaa gaaaagctgt 1320
cagcgcaggc gtctctgaag cggcatacct ccttgaatga cctcagcctg acgagggatg 1380
agcaggagat cgagttcctg aggctgcagg tgctggagca gcagcacgtc attgacgacc 1440
tctcactgga gagagaacgg ctgttgcgct ccaaaaggca tcgagggaaa agtctgaaac 1500
cgcccaagaa gcatgttgtg gagacatttt ttggatttga tgaggagtct gtggactcag 1560
aaacgttgtc cgaaacatcc tacaacacag acaggacaga caggacccca gccacgcccg 1620
aagaagactt ggacgatgcc acagcccgag aggaggctga cctgcgcttc tgccagctga 1680
cccgggagta ccaggccctg caacgcgcct acgccctgct ccaggagcag gtgggaggca 1740
cgctggacgc tgagagggag gcccggactc gggagcagct acaagctgat ctgctgaggt 1800
gtcaggccaa aatcgaagat ttggagaagt tactggttga gaagggacag gattccaagt 1860

```
gggttgaaga gaagcagctg ctcatcagaa caaaccaaga cttgctggaa aagatttaca   1920

gactggaaat ggaagagaac cagctgaaga atgaaatgca agacgccaag gatcagaacg   1980

agctgttaga attcagagtg ctagaactcg aagtaagaga ctctatctgt tgtaaactct   2040

caaacggagc agacattctc tttgaaccca aactgaaatt catgtaaagc tctcagatgt   2100

tttcaagcat gtgtaaaggg gacatgttat agtttctttc tttctttctt tctttttttt   2160

tttaaatctg tatgttcaga ataatttcac tgccttaatg tgttctggag agcgtgctca   2220

cccaagtcta tggacatgta ccagagctaa tatatttatt gcctatggct tgttttgcac   2280

ttaataaaat aatttgtttt tacaaaaaaa                                     2310
```

<210> SEQ ID NO 8
<211> LENGTH: 1320
<212> TYPE: DNA
<213> ORGANISM: Homo sapiens

<400> SEQUENCE: 8

```
gcggacgcgg ggcgccagca ggtggcgctg gacgcgcaac ggacaaggag gcggggcctg     60

cagctggctt ggaggctccg cgctctggag gctcaggcgc cgcgtggggc ccgcacctct    120

gggcagcagc ggcagccgag actcacggtc aagctaaggc gaagagtggg tggctgaagc    180

catactattt tatagaatta atggaaagca gaaaagacat cacaaaccaa gaagaacttt    240

ggaaaatgaa gcctaggaga aatttagaag aagacgatta tttgcataag gacacgggag    300

agaccagcat gctaaaaaga cctgtgcttt tgcatttgca ccaaacagcc catgctgatg    360

aatttgactg cccttcagaa cttcagcaca cacaggaact ctttccacag tggcacttgc    420

caattaaaat agctgctatt atagcatctc tgacttttct ttacactctt ctgagggaag    480

taattcaccc tttagcaact tcccatcaac aatattttta taaaattcca atcctggtca    540

tcaacaaagt cttgccaatg gtttccatca ctctcttggc attggtttac ctgccaggtg    600

tgatagcagc aattgtccaa cttcataatg gaaccaagta taagaagttt ccacattggt    660

tggataagtg gatgttaaca agaaagcagt ttgggcttct cagtttcttt tttgctgtac    720

tgcatgcaat ttatagtctg tcttacccaa tgaggcgatc ctacagatac aagttgctaa    780

actgggcata tcaacaggtc caacaaaata aagaagatgc ctggattgag catgatgttt    840

ggagaatgga gatttatgtg tctctgggaa ttgtgggatt ggcaatactg gctctgttgg    900

ctgtgacatc tattccatct gtgagtgact ctttgacatg gagagaattt cactatattc    960

agagcaagct aggaattgtt tcccttctac tgggcacaat acacgcattg atttttgcct   1020

ggaataagtg gatagatata aaacaatttg tatggtatac acctccaact tttatgatag   1080

ctgttttcct tccaattgtt gtcctgatat ttaaaagcat actattcctg ccatgcttga   1140

ggaagaagat actgaagatt agacatggtt gggaagacgt caccaaaatt aacaaaactg   1200

agatatgttc ccagttgtag aattactgtt tacacacatt tttgttcaat attgatatat   1260

tttatcacca acatttcaag tttgtatttg ttaataaaat gattattcaa ggaaaaaaaa   1320
```

<210> SEQ ID NO 9
<211> LENGTH: 1700
<212> TYPE: DNA
<213> ORGANISM: Homo sapiens

<400> SEQUENCE: 9

```
gcggagtccg gacgtcggga gcaggatggc ggcggagcag gaccccgagg cgcgcgcggc     60

ggcgcggccg ctgctcactg acctctacca ggccaccatg gcgttgggct attggcgcgc    120
```

```
gggccgggcg cgggacgccg ccgagttcga gctcttcttc cgccgctgcc cgttcggcgg    180
cgccttcgcc ttggccgccg gcttgcgcga ctgtgtgcgc ttcctgcgcg ccttccgcct    240
gcgggacgcc gacgtgcagt tcctggcctc ggtgctgccc ccagacacgg atcctgcgtt    300
cttcgagcac cttcgggccc tcgactgctc cgaggtgacg gtgcgagccc tgcccgaggg    360
ctccctcgcc ttccccggag tgccgctcct gcaggtgtcc gggccgctcc tggtggtgca    420
gctgctggag acaccgctgc tctgcctggt cagctacgcc agcctggtgg ccaccaacgc    480
agcgcggctt cgcttgatcg cagggccaga gaagcggctg ctagagatgg gcctgaggcg    540
ggctcagggc cccgatgggg gcctgacagc ctccacctac agctacctgg gcggcttcga    600
cagcagcagc aacgtgctag cgggccagct gcgaggtgtg ccggtggccg ggaccctggc    660
ccactccttc gtcacttcct tttcaggcag cgaggtgccc cctgacccga tgttggcgcc    720
agcagctggt gagggccctg gggtggacct ggcggccaaa gcccaggtgt ggctggagca    780
ggtgtgtgcc cacctggggc tgggggtgca ggagccgcat ccaggcgagc gggcagcctt    840
tgtggcctat gccttggctt ttccccgggc cttccagggc ctcctggaca cctacagcgt    900
gtggaggagt ggtctcccca acttcctagc agtcgccctg gccctgggag agctgggcta    960
ccgggcagtg ggcgtgaggc tggacagtgg tgacctgcta cagcaggctc aggagatccg   1020
caaggtcttc cgagctgctg cagcccagtt ccaggtgccc tggctggagt cagtcctcat   1080
cgtagtcagc aacaacattg acgaggaggc gctggcccga ctggcccagg agggcagtga   1140
ggtgaatgtc attggcattg gcaccagtgt ggtcacctgc ccccaacagc cttccctggg   1200
tggcgtctat aagctggtgg ccgtgggggg ccagccacga atgaagctga ccgaggaccc   1260
cgagaagcag acgttgcctg ggagcaaggc tgctttccgg ctcctgggct ctgacgggtc   1320
tccactcatg gacatgctgc agttagcaga agagccagtg ccacaggctg ggcaggagct   1380
gagggtgtgg cctccagggg cccaggagcc ctgcaccgtg aggccagccc aggtggagcc   1440
actactgcgg ctctgcctcc agcagggaca gctgtgtgag ccgctcccat ccctggcaga   1500
gtctagagcc ttggcccagc tgtccctgag ccgactcagc cctgagcaca ggcggctgcg   1560
gagccctgca cagtaccagg tggtgctgtc cgagaggctg caggccctgg tgaacagtct   1620
gtgtgcgggg cagtccccct gagactcgga gcggggctga ctggaaacaa cacgaatcac   1680
tcacttttcc ccacaaaaaa                                                1700
```

<210> SEQ ID NO 10
<211> LENGTH: 11130
<212> TYPE: DNA
<213> ORGANISM: Homo sapiens

<400> SEQUENCE: 10

```
gggctggctg agcgcgggcg agtgtgagcg cgagtgtgcg cacgccgcgg gagcctctct     60
gccctctcct cgcaccctgc tcagggcatc tgaagagcct ggaaacgtga acaggcttga    120
agtatggcat gttgcaaaga tggtttctgc caagaaggta cccgcgatcg ctctgtccgc    180
cggggtcagt ttcgccctcc tgcgcttcct gtgcctggcg gtttgtttaa acgaatcccc    240
aggacagaac caaaaggagg agaaattgtg cacagaaaat ttcacccgca tcctggacag    300
tttgctcgat ggttatgaca acaggctgcg tcctggattt gggggtcctg ttacagaagt    360
gaaaactgac atatatgtca ccagctttgg acctgtttct gatgttgaaa tggaatacac    420
aatggatgtg ttcttcaggc agacatggat tgacaaaaga ttaaaatatg acggccccat    480
tgaaattttg agattgaaca atatgatggt aacgaaagtg tggacccctg atactttctt    540
```

```
caggaatgga aagaaatctg tctcacataa tatgacagct ccaaataagc tttttagaat    600
tatgagaaat ggtactattt tatacacaat gagactcacc ataagtgcgg agtgtcccat    660
gagattggtg gattttccca tggatggtca tgcatgccct ttgaaattcg ggagttatgc    720
ctatccaaag agtgagatga tctatacctg gacaaaaggt cctgagaaat cagttgaagt    780
tccgaaggag tcttccagct tagttcaata tgatttgatt gggcaaaccg tatcaagtga    840
aaccatcaaa tcaattacgg gtgaatatat tgttatgacg gtttacttcc acctcagacg    900
gaagatgggt tattttatga ttcagaccta tattccgtgc attatgacag tgattctttc    960
tcaagtttca ttttggataa ataaagaatc agttcccgct aggactgtat ttggaataac   1020
aactgtcctc accatgacca cactaagcat cagtgcacga cattctttgc ccaaagtgtc   1080
ctatgctacc gccatggact ggttcatagc tgtctgcttt gcttttgtat tttcggccct   1140
tatcgagttt gctgctgtca actatttcac caatattcaa atggaaaaag ccaaaaggaa   1200
gacatcaaag ccccctcagg aagttcccgc tgctccagtg cagagagaga agcatcctga   1260
agcccctctg cagaatacaa atgccaattt gaacatgaga aaaagaacaa atgctttggt   1320
tcactctgaa tctgatgttg gcaacagaac tgaggtggga aaccattcaa gcaaatcttc   1380
cacagttgtt caagaatctt ctaaaggcac acctcggtct tacttagctt ccagtccaaa   1440
cccattcagc cgtgcaaatg cagctgaaac catatctgca gcaagagcac ttccatctgc   1500
ttctcctact tctatccgaa ctggatatat gcctcgaaag gcttcagttg gatctgcttc   1560
tactcgtcac gtgtttggat caagactgca gaggataaag accacagtta ataccatagg   1620
ggctactggg aagttgtcag ctactcctcc tccatcggct ccaccacctt ctggatctgg   1680
cacaagtaaa atagacaaat atgcccgtat tctctttcca gtcacatttg ggcatttaa    1740
catggtttat tgggttgttt atttatctaa ggacactatg gagaaatcag aaagtctaat   1800
gtaatttcgt tgctatagta gtttgctaaa agatgatgaa aatgcagaat gtctttttaa   1860
atgtttttaa atataaacaa atattcttta ctaaaataaa aactctgtgt aatttttcca   1920
tttaaagata taagccagtt attgggagag ttaattaatt cctgagtgaa aaagtgaact   1980
atgttttttt tcagaaaaat tattttaaaa gaactcagca ttcagttaga tagaatacac   2040
accatcctgg aaagttggga taagagaaat agagctatta gagacaagtg gcgcatattt   2100
tttcattgat atttgaaaac agactatgac attttaaaaa tctgccctat gagtatcaac   2160
ctgccaccct aaatttccca gtggcactac ccttaaccag aattgtttat tagatgtcat   2220
atgcagtgac ctttggtgat cttcttagga acttcaagaa aaggaatttt cctgttaaat   2280
taaacattgg caaaaggaaa tggaatagta taaacactga tcaatagagt aaaatatctg   2340
ctgcataaaa aactaagaca aagaccagag gaaatatctt ccctttctta tgttggctaa   2400
acagtactta acagttgact tgaaattttg ttctctgagc caaagtttaa ctcattgtat   2460
gaattctttt tcatggtagt tcattcagtt atgtgtttat ttactacata gttattcaga   2520
gcctactgtg ttccaggaac tatgctagaa actgtctctc taggaaagct cttgcacctt   2580
tatctacaat attacttaaa aagtagaaca gtcaatgcat gccaaagaac cataaactag   2640
cagaggacat tgcattcttt agtgaaggac atttatttag agtctgacaa catattcaaa   2700
atatttttca gcctctactg atagtggata acaaatatat ttgttcacat aaccactttg   2760
atgtcagtac aacttcagca attggttttc aaaatagatg agaatatggt acagattgtt   2820
ctataagtga aaagcattat gtacttgaaa gtaaaaatca gggcaatata agacttaata   2880
gattaactgt cgcaaatttg atcagagtca cagagtagaa tttgatcaga atcacagaat   2940
```

```
catcagacat aggaactgag cacaggcttt ttcaggtgct ttccccaaga tagatctaga   3000
tattagctag tgaaatgcta aattttgaag agttttgtgt ccgtagttct gtaattctgg   3060
gcagtcatca tgttggtttt tttgggagtt tttttaaggt ttaataacta aggggaatat   3120
tttaaaatta agagagcagc aaatgaaagg agtaaagaaa aaaatagctg tcgggtagga   3180
tgccactgac tctgctatgt gatttatcag ggttttcatc tactgacttc tttctcatta   3240
ggtaggctta acaacttact tgagaatttt gcaactgtct atgcagctga atctaagtat   3300
ggtttttgt catattgcct ctagattttc ttctgtgctt ctctctatct gctctggaat   3360
ggatgagtga atgtgttctg ggtgttttag ggaacatatt gatagaaatg accaccttgc   3420
agacaaaatc tctctctctc tttttgtttt tatagaaaag aagtgatagt agttaattgg   3480
catcgatttt tcagatattg cactacctta taatggttgt ttttgatacc tgaaaattgt   3540
gcaaatgcca aatattaatt gtaagtcata tctgagaaat cattcttggc tgtctttcta   3600
ggtattccat agaatcaaca cattttaagg ctgaaagata ctgtcgaaat cacccagtcc   3660
caaccccca atttaaaatt gattctagta aaattaggtc cagtaacacc tgtatatatg   3720
tatatattta ataaagagta cttgtacaaa aaagcttatc ataaattatt tcatgaatgt   3780
gaatagattt ctggccttga ggacgatgtt tggaaatatg gttggaagca caattcattc   3840
gctactagtt attcagagcg tactttgttc caggaactat gctggaaact gatagttcac   3900
tattctgatg aaaaggctgg ttttgttgtt gttgttgttg ttgttgttgt tgtttttggt   3960
gaggaactct tactctttgc taatctattg gcctatctta agaaataatt atttggttat   4020
tcattggctt cctttaaaaa aaagtgttct tctacaaatc ttacagagtg taaagagata   4080
aaaagaaatg atttttttc ttacctttac atatgaaggt ttaaaaatac atcatgtggc   4140
caaagaatga gaaaggacag aattaaccaa ggattcttaa ttgttaattt gaagaacaca   4200
ttaaccagaa agcttaaaca ttattattaa aataaattat ttcatttgca cacaatgata   4260
ataatgatga taataataat aataataata ataataataa taataataat aatatgttgt   4320
ttgctttcct taactgaatt tcatcaaatt cattcagtga tttttatttt ggtcattatt   4380
tctatcttcc caataaccca gaggtacatc aagtaaaaac acttttgcaa agagccagtc   4440
acttttccct cttagaaaat ctcagaagaa tgattagggg cacccaaagt tctggttatc   4500
tatgaataat aatgaataat tttggctgag aatggtacct ttatataact cttttaaaga   4560
tgaaattcag aataatttta ttcaggacct agtatctgca gtccatgttg gccactaact   4620
gctacataat tactttcaat ttcctccagg catgactagg tataaacata tatttacatg   4680
attaatccac attttaaaat gacttgcact tgtgcatata catagtactt tgaataatgt   4740
atattttaaa ttggacctca caaatcttgt attaaagtag gtagagagta gagtcacact   4800
tttttgatg aaatgagtca cagagaagtt acatgacaaa gataaaatca cagggttgga   4860
aagaactttg aaaggtcatt tttcaataat ctcaccttaa aagtgacccc ttttcaaaca   4920
aagcataaac aatttatttg tggcttattt tacccatgag ctggccaata cttcctggcc   4980
tagaaaaata tctccactct ccccattcct gttcttaatg gtcttctctt ctcaatttgt   5040
aaatattctc cagtaaaaga caccaggtgt ggagatgggt cacttaattt caagttctga   5100
gtgtcttgtg gttttaaaca agtctcttaa cctctctaag actgattcct catttataac   5160
agggaggagg tggattatgt aatatctaag agcttttcag ttttaatact ctctgattct   5220
catagtaaat acaagcatac tcttgtaaga aaaacactga atactttgaa ccacaaataa   5280
gtgtttatgg acaaaaattt agttctactg cttgattact ttaagttcat tgcttgcttc   5340
```

```
aaactaaggt ttccctacct tcaaaaatat atataacatc tctccattta gataaagtat   5400
attcttcccc agggaagact gtattcttta aagacagtag aatattggct atttctcttt   5460
tctgggattt cctgggcttt tattcactaa atgggctcct gcccagtttg ggtactgtgc   5520
tgatttttag atatacagag ataaaaatag cccctttcct tgcaggtagt cacagtccgg   5580
aagagatgat agatgcatag acaaaaaatt atgggatgta actaatgctt cagtagaata   5640
cagcagggcc aaaactagag tgatactcat ctcaggcaca aatatatatg gggacatcaa   5700
aacttcaata atcaagatac ctaatattta agtgaatatt tttaaaactc aaaattaatg   5760
caaaagattt atgatgaaca gaatatacaa attttaaata aattaataga atcagtagta   5820
ataatatttt cttctgcctc aggctccaaa attgctcagc atagcactga tctagataga   5880
ggtggataaa agatccacat aacttaatta cattgttgaa ggagaggaac aagagtgata   5940
gcagagaagg tttcacagat ataatcttaa gctaaatttt atagaatgat ttggagttct   6000
tatagcctcc attcccactt ccacaaacaa acaaaaaaat gaaagcgcaa ttttatcagc   6060
acctgaggca ggagaagaga tgaggatgtg gaaagtcaag gggaactctt actacaaatt   6120
cttagttctg tgtttggagg taagggtgaa tgcagggaag tgagagttgt tgatgttgga   6180
aagacctaaa gagcctggat taggaagagt tttgtgtaaa ttactgaagg aatggaattt   6240
gatcaggatt agtggcaatt tattaaaaat cttgaagaat aatacgatga aaactaacat   6300
ccttattttt ctgttttaga gaaagcacct gattattgtg tgaactatgg tttggagggc   6360
cacaaatcta gaggtagtgg aacagttgag atctcttatt ttttctttcc tgtcttaaac   6420
tttgccttct attccttttt tctttttttg accgcaatga cttcattgtc atttgtaaaa   6480
gtgatacatg actgttaaag atagacattg tagaaactta aaaacaatct caaaattcta   6540
ccacccagaa atcagaaata ttttgtattt ggatatgttt gtctagaaga gtagattgct   6600
tgattaaaag acagagtttt ataaatgtag aagccaatat gacatacatg ctgccattaa   6660
ataataaaaa attaaattga cttttatctc aagataagat taaaattgga gggtaaaact   6720
gaagaaattg ttgaaatttg gatggtgctt ctttaaagca agagatttag agagtcagag   6780
ctttttatcc caggtttcaa tctttatttc aggaaaattt tctgcaattt tgtctaagtt   6840
aatttttttt ttttaagaaa tgccaattat gtcaaatccc ttttgtctct atacaatagt   6900
ccccaactgt tttggcaaca ggcacgggtg agggtggggg aatggttttc agatgaaatt   6960
gttccatctc agatcatcag gcattagtcg attctcataa ggagcggaca accttgcatg   7020
ccctcctatg agaatctaat gccgccgcta atctgacagg aggcagagct caggcgataa   7080
tgctcaatgg gtgccactca cctcctgttg tgctgcccaa ttcctaacag gtcatggata   7140
agtactggtc agtggcccag gggttgggga ccactgctct gtaactattt acagtattct   7200
ttgtaactac tttggtatct ttaaaatttt ctttaacttt tgtcaaccat aaccctagtg   7260
agttttcagt tgtgattatt ctattttgta acttccaatg tacttttcaa cttcataatg   7320
gttaattttg ttttccattg ctttcttggt cactgtcatt tcatttttct tctctttctc   7380
tatttttacc attgctttat tgaaatatct tctttgagct tctcatgttt ctctattaat   7440
gagatcatgt ctataatatt ttttgagact acagagacct atttatataa actcttcctc   7500
tatttcttga aaaagttttt atctggcgtg agcttcatct gctttttcat tgaggtttta   7560
tctcccttgc ctatttttgg ggctggtttc tttctattaa tcactgagca gagccagcta   7620
tttactgaac tacagtgtgg gaagtggtgg gagggtgagt cagatcagcc cacagaagct   7680
atttaaattt caggtttcaa gcccacctcc ccaaaaccgt tttatgtgtt ttttcttctg   7740
```

```
cccaggcacc atatttttat atctattttt gacatttggg cggcctatgt agttcacagt   7800
gtaaaactct ctgttttact ttctttatgt tattgctagt gattattgct tgtagtccca   7860
ccccccttccc cacattagcc ttagtattct atattattca gcaagcttgt tcacaactct   7920
caaatatagt ctatcagaat ttttatcttt acctctacat tccactattc ggaagtatat   7980
agtaaaatcg tatgaagaca gattttgtct ttttcttgcc tgtttacact ctatcttaca   8040
gaggtttcaa acaaaccatc tttgtttgaa acatcgcagg ataatgatac ttattgaaat   8100
ctacatcctg cccaagatat atgccagtca atttcctttc tcctattagt gcaaatggct   8160
acctacttaa aagctgctga ctatagtttg tcatcaatta cttgttaatt acagatatgg   8220
ttttcatttt tttttctcaa tttttcatta tgttattttt ggagactgtc ttaggtgggg   8280
agtgaattat aaatattttt atttcaccac ctttaactga gtcaccatat gttatttgca   8340
cttccaatag accagggatt gaccagagta tcttttactg atatgaccac cagagctaca   8400
tggcttttac cttctgtata tcagatgtca ctggaatcaa gcattaaacc tagattaaat   8460
ctggattaaa ccagctgtat ggcaccttag aaaattgaga aggactagga agctgataga   8520
aagaactcct gtataaaaaa taaattcttt ttacattttc cttggtagta tttctgcaag   8580
cttctttagt ttctataggg gaatcccaga gttttcctct gagattgctt ccctttcctt   8640
tgtattttca tttttccctc ttgggcttta cttttcagtc gtgtatttct atcccaatgt   8700
taatttatta cactgtttat attttcctgt ccttcaattc atcagtagat tagtgaagta   8760
cttattcctt taattataag tataaacgtt tttaatttct ttttggataa cgatacattt   8820
aatggaaaat ttttaaatgc tatggtttct taatagcttt tctctaccac taattacttc   8880
cgttaaaaaa aaaaagaaat acccatgcgt aatataaaag aaattttgaa taaaatgtta   8940
tcctttcctt ttactagaga caaacatctc cacttcaaaa tggaaaaatg gaactatgca   9000
aaggaaattt acgatattca agagtatgat attatcactg aaccgattaa tttaattgaa   9060
aatactaacc tgcaaaaaag aattacacaa atgtatttga aatgtcatca gatacctcaa   9120
gctatgacag agttgattat gttacacaag tagtaaagga taaattaaat atattctata   9180
ttaacactaa gatttaaaac taattatagt cttctttaat ttttctactg tatacatttc   9240
atctagtttt cagtaaaaca aactttttcat tacttttact tatcccatgc aaatctagtt   9300
gctataagat ataacctaat ttggaaatac ctccctgtaa tacattggaa ttttggtgtg   9360
agtgtgtgtg atcagagagg ataaacaaat ggtgtcagca aaatagaatg taaaatatgg   9420
agataatgtg gatttacaca atttgataaa aattctccct tgaattttgc agatcatata   9480
tgaatatcat catgtgaagt gcaattagga ttttttcata tattaataca tatacatcat   9540
ctctttaata aaatatttttg ctgaactcgt ttaatatttc tcatgtctca tatttcatat   9600
tttctcatat gtctcatatt ttatattttc tcatatgtgt ctcattttta ttattactat   9660
agtatccatt aaaggagact ggcaaatacc tgaacaaagt tatgttgttg gcaatataag   9720
atattaccaa ttgcataata ttatttccaa aggcaaatta atatgcaaac tatagatttc   9780
catgggtatc tatacaaatt attacttgaa gtccatagaa aacagcttcc ttagagggaa   9840
gtaaaagaag ctctgataac agacaatgta tagcatttca gttaaagttt gattgacata   9900
tttttttctc agtcttttat acttgtgaat tatagtctac attttgtctt tacagatgtt   9960
gctaacacag tgcagcatgt tggcttgtca ttttactgat tatgtatatt gtctcctagt  10020
tcaagtatac agtaaatcag agctttcatt tttcaagggg cagaaaaata attgttggtt  10080
gataaggtaa ggttatatga ttttgaggga gcttcattgt aaattgaatg agaatccggt  10140
```

```
tttcatgcaa aggtgtatct atgcgataat actttgaatg tctgtagttt gaaatagaag  10200
gttaattttt tccactggct tatccttaat gaaggaaatc ccctgataat tactttgatt  10260
ctgaaaatgt tgaaaactcc agaagaaata aagcttttct ttgatttctc agctgaagtg  10320
ttgtacaaac tgaggaatat gaagtccatt cccttctttc ttctcttgaa taattttaaa  10380
attgtttgtt tagttgtaca attgaaaata ttccttatta tagaagtaaa aaaacaataa  10440
tgcatatttc ctcatatcat aaaaactaaa tttgttatca tctgagcttc aatattcttg  10500
ctcaattaga atagtaaata taaagtgtga tatttataac agttcaaggt ttgataggag  10560
atagaggtgt tttgatttta tgggaaaatt acttcctcaa gaacacattt cttgaggttt  10620
tagtaatcac atttgactcc ctgaaattgg caattttatt caatgtagga atattatcat  10680
ggtatattat agtgaggagc acatagtcat tattattttg tttttgcaaa tttattttga  10740
aaaaaaggag cattatcaaa tattggttta ctattttaaa gtaattcatc aggaaatgat  10800
tttttaaaca ctgtcccttt aagtaaatgt cccttgcttt tcaaagctca acttattact  10860
tatggtaata gagttacttt gcttcttaaa acaaagttta tactagagca tagcattgta  10920
gaattattca ggtctcaatt tctcactgga aaatgagtct ttaaaatagt aaggatttaa  10980
atttctataa aatttaatca cagatactta tattttaaga taaatgtgtt ggagctaaac  11040
tctggaatta ttaaaatata aaacattata tccctctaat gtattttttc tatttaaatt  11100
taaaacaata aacataaata tctttggaaa                                  11130
```

<210> SEQ ID NO 11
<211> LENGTH: 1520
<212> TYPE: DNA
<213> ORGANISM: Homo sapiens

<400> SEQUENCE: 11

```
ccacgcgtcc ggtggtaaag ggacggaggg gaagccctga gaggactgag aggatgggaa    60
attctctgct gagagaaaac aggcggcagc agaacactca agagatgcct tggaatgtga   120
gaatgcaaag ccccaaacag agaacatcca gatgctggga tcaccatatc gctgaagggt   180
gtttctgcct tccatggaaa aaaatactca tttttgaaaa gaggcaagat tcccaaaacg   240
aaaatgaaag aatgtcatct actcccatcc aggacaatgt tgaccagacc tactcagagg   300
agctgtgcta taccctcatc aatcatcggg ttctctgtac aaggccatca gggaactctg   360
ctgaagagta ctatgagaat gttccctgca aagctgagag acccagagag tccttgggag   420
gaactgagac tgagtattca cttctacata tgccttctac agaccccagg catgcccgat   480
ccccagaaga tgaatatgaa cttctcatgc ctcacagaat ctcctctcac tttctgcaac   540
agccacgtcc acttatggcc ccttctgaga ctcagttttc ccatttatag tgaagtggct   600
ggactagcat ttgtttagca ccaacaaata aaaggtggga tgggggatct gcctgaagca   660
gggatgggac acaaagtccc tccagcttat ctcccacaac aaccctttcc ctgcagagca   720
tggtttgtat accacaagcc ctcttagcac gcaaaagcca aaatctaaag atcaaccatt   780
tatcctgaac aacaccattt gagaaagagg taaccatctt tggttctaca tggtttggag   840
agtatagtgg taggaggggc tccctgattc ccctaaagct atgcacacca caaggggctc   900
tgctcttctg tctgggatct tcttataaag tgttcccatg atcattctct aaagtcacga   960
ggaagcttta ctcatcatac taagtgtgcc caagggggag ttcactcatt actgtgacct  1020
tccagctcag tccccaccca tgggagcctg tgttgctcct ctcactccat gtgtctaagt  1080
catgtctttt acatagtgtc ctttgacctg ttggccccca tggtctggtt agttatgtga  1140
```

```
gttgaatcaa gaggctctag gccagatgtt tacataattt taacctatat gattttattt   1200

ttaactttgt atttctccct agaaatctta ataagacaat tatgccatca gacaatgtta   1260

agaagaacga tccttggaga tcccgtaatc ccactaccct tctttggctc agagaggata   1320

atttgcctaa tgatacatta aagttagtgg caaaacttaa tttggagcct gatttcctac   1380

tgacttccaa tttagtgctc ccccagtatg ctaaatagaa agccctctgc aatatattaa   1440

atgtatacta aatgtatata tttaataatg tcatgtataa aatatgaata aaatgtccac   1500

ataggaaatt aacacataaa                                               1520


<210> SEQ ID NO 12
<211> LENGTH: 1300
<212> TYPE: DNA
<213> ORGANISM: Homo sapiens

<400> SEQUENCE: 12

ataagaggtt gggctttgga tagatagaca gactcctggg tccggtcaac cgtcaaaatg     60

tccaaagaac ctctcattct ctggctgatg attgagtttt ggtggcttta cctgacacca    120

gtcacttcag agactgttgt gacggaggtt ttgggtcacc gggtgacttt gccctgtctg    180

tactcatcct ggtctcacaa cagcaacagc atgtgctggg ggaaagacca gtgcccctac    240

tccggttgca aggaggcgct catccgcact gatggaatga gggtgacctc aagaaagtca    300

gcaaaatata gacttcaggg gactatcccg agaggtgatg tctccttgac catcttaaac    360

cccagtgaaa gtgacagcgg tgtgtactgc tgccgcatag aagtgcctgg ctggttcaac    420

gatgtaaaga taaacgtgcg cctgaatcta cagagagcct caacaaccac gcacagaaca    480

gcaaccacca ccacacgcag aacaacaaca acaagcccca ccaccacccg acaaatgaca    540

acaaccccag ctgcacttcc aacaacagtc gtgaccacac ccgatctcac aaccggaaca    600

ccactccaga tgacaaccat tgccgtcttc acaacagcaa acacgtgcct ttcactaacc    660

ccaagcaccc ttccggagga agccacaggt cttctgactc ccgagccttc taaggaaggg    720

cccatcctca ctgcagaatc agaaactgtc ctccccagtg attcctggag tagtgctgag    780

tctacttctg ctgacactgt cctgctgaca tccaaagagt ccaaagtttg ggatctccca    840

tcaacatccc acgtgtcaat gtggaaaacg agtgattctg tgtcttctcc tcagcctgga    900

gcatctgata cagcagttcc tgagcagaac aaaacaacaa aaacaggaca gatggatgga    960

atacccatgt caatgaagaa tgaaatgccc atctcccaac tactgatgat catcgccccc   1020

tccttgggat ttgtgctctt cgcattgttt gtggcgtttc tcctgagagg gaaactcatg   1080

gaaacctatt gttcgcagaa acacacaagg ctagactaca ttggagatag taaaaatgtc   1140

ctcaatgacg tgcagcatgg aagggaagac gaagacggcc tttttaccct ctaacaacgc   1200

agtagcatgt tagattgagg atgggggcat gacactccag tgtcaaaata agtcttagta   1260

gatttccttg tttcataaaa aagactcact taaaaaaaaa                         1300


<210> SEQ ID NO 13
<211> LENGTH: 1730
<212> TYPE: DNA
<213> ORGANISM: Homo sapiens

<400> SEQUENCE: 13

tttacggcgc ggagccggag agacctgggc tggcgcgggc gggagctgcg gcggataccc     60

ttgcgtgctg tggagaccct actctcttcg ctgagaacgg ccgctagcgg ggactgaagg    120

ccgggagccc actcccgacc cggggctagc gtgcgtccct agagtcgagc ggggcaaggg    180
```

```
agccagtggc cgccgacggg ggaccgggaa acttttctgg gctcctgggc gcgccctgta    240
gccgcgctcc atgctccggc agcggcccga aacccagccc cgccgctgac ggcgcccgcc    300
gctccgggca gggcccatgc cctgcgcgct ccgggggtcg taggctgccg ccgagccggg    360
gctccggaag ccggcggggg cgccgcggcc gtgcggggcg tcaatggatc gccactccag    420
ctacatcttc atctggctgc agctggagct ctgcgccatg gccgtgctgc tcaccaaagg    480
tgaaattcga tgctactgtg atgctgccca ctgtgtagcc actggttata tgtgtaaatc    540
tgagctcagc gcctgcttct ctagacttct tgatcctcag aactcaaatt ccccactcac    600
ccatggctgc ctggactctc ttgcaagcac gacagacatc tgccaagcca aacaggcccg    660
aaaccactct ggcaccacca tacccacatt ggaatgctgt catgaagaca tgtgcaatta    720
cagagggctg cacgatgttc tctctcctcc caggggtgag gcctcaggac aaggaaacag    780
gtatcagcat gatggtagca gaaaccttat caccaaggtg caggagctga cttcttccaa    840
agagttgtgg ttccgggcag cggtcattgc cgtgcccatt gctggagggc tgattttagt    900
gttgcttatt atgttggccc tgaggatgct tcgaagtgaa aataagaggc tgcaggatca    960
gcggcaacag atgctctccc gtttgcacta cagctttcac ggacaccatt ccaaaaaggg   1020
gcaggttgca aagttagact tggaatgcat ggtgccggtc agtgggcacg agaactgctg   1080
tctgacctgt gataaaatga gacaagcaga cctcagcaac gataagatcc tctcgcttgt   1140
tcactggggc atgtacagtg ggcacgggaa gctggaattc gtatgacgga gtcttatctg   1200
aactacactt actgaacagc ttgaaggcct tttgagttct gctggacagg agcactttat   1260
ctgaagacaa actcatttaa tcatctttga gagacaaaat gacctctgca aacagaatct   1320
tggatatttc ttctgaagga ttatttgcac agacttaaat acagttaaat gtgttatttg   1380
cttttaaaat tataaaaagc aaagagaaga ctttgtacac actgtcacca gggttatttg   1440
catccaaggg agctggaatt gagtacctaa ataaacaaaa atgtgcccta tgtaagcttc   1500
tacatcttga tttattgtaa agatttaaaa gaaatatata tattttgtct gaaatttaat   1560
agtgtctttc ataaatttaa ctgggaaacg tgagacagta catgttaatt atacaaatgg   1620
ccatttgctg ttaataattt gttctcaact ctaggatgtg gcttggtttt tttttttctc   1680
ttttcttttt taaacaagac caagatcttg cttattcttc catgaaaaaa              1730
```

<210> SEQ ID NO 14
<211> LENGTH: 7240
<212> TYPE: DNA
<213> ORGANISM: Homo sapiens

<400> SEQUENCE: 14

```
acggccatgg aggacgcggg agcagctggc ccggggccgg agcctgagcc cgagcccgag     60
ccggagcccg agcccgcgcc ggagccggaa ccggagccca agccgggtgc tggcacatcc    120
gaggcgttct cccgactctg gaccgacgtg atgggtatcc tggacggttc actgggaaac    180
atcgatgacc tggcgcagca gtatgcagat tattacaaca cctgtttctc cgacgtgtgc    240
gagaggatgg aggagctgcg gaaacggcgg gtttcccagg acctggaagt ggagaaaccc    300
gatgctagcc ccacgtcact tcagctgcgg tcccagatcg aagagtcgct tggcttctgt    360
agcgccgtgt caaccccaga agtggaaaga aagaaccctc ttcataaatc aaactcagaa    420
gacagctctg taggaaaagg agactggaag aagaaaaata agtatttctg gcagaacttc    480
cgaaagaacc agaaaggaat aatgagacag acttcaaaag gagaagacgt tggttatgtt    540
gccagtgaaa taacgatgag cgatgaggag cggattcagc taatgatgat ggtcaaagaa    600
```

```
aagatgatca caattgagga agcacttgct aggctcaagg aatacgaggc ccagcaccgg    660
cagtcggctg ccctggaccc tgctgactgg ccagatggtt cttacccaac gtttgatggc    720
tcatcaaact gcaattcaag agaacaatcg gatgatgaga ctgaggagtc ggtgaagttt    780
aagaggttac acaagctggt aaactccact cgcagagtca gaaagaaact aattagggtg    840
gaagaaatga aaaaacccag cactgaaggt ggggaggagc acgtgtttga gaattcgccg    900
gtcctggatg aacggtccgc cctctactct ggcgtgcaca agaagcccct tttctttgat    960
ggctctcctg agaaacctcc cgaagatgac tcagactctc tcaccacgtc tccatcctcc   1020
agcagcctgg acacctgggg ggctggccgg aagttggtca aaaccttcag caaaggagag   1080
agccggggcc tgattaagcc ccccaagaag atggggacat tcttctccta cccagaagaa   1140
gaaaaggccc agaaagtgtc ccgctccctc accgaggggg agatgaagaa gggtctcggg   1200
tccctaagcc acgggagaac ctgcagtttt ggaggatttg acttgacgaa tcgctctctg   1260
cacgttggca gtaataattc tgacccaatg ggtaaagaag gagactttgt gtacaaagaa   1320
gtcatcaaat cacctactgc ctctcgcatc tctcttggga aaaaggtgaa atcagtgaaa   1380
gagacgatga gaaagagaat gtctaaaaaa tacagcagct ctgtctctga gcaggactcg   1440
ggccttgatg gaatgcctgg ctcccctccg ccttcacagc ccgaccccga acacttggac   1500
aagcccaagc tcaaggccgg gggttctgta gaaagtcttc gcagttctct cagtgggcag   1560
agctccatga gcggtcaaac agtgagcacc actgattcct caaccagcaa ccgggaaagc   1620
gtcaagtcgg aagatgggga tgacgaagag ccgccttacc gaggcccgtt ctgcgggcgt   1680
gccagggtgc acaccgactt cacccccagt ccctatgaca cagactcact caagctcaag   1740
aaaggagata tcatcgatat aatcagcaag ccacccatgg ggacctggat gggcctgctg   1800
aacaacaaag tcggcacgtt caagttcatc tacgtggacg tgctcagtga agacgaggag   1860
aaacccaaac gccccaccag gaggcgtcgg aaaggacgac caccccagcc caagtctgtg   1920
gaggatctcc tggatcggat taacctaaaa gagcacatgc ccactttcct gttcaatgga   1980
tatgaagatt tggacacctt taagctgctg gaggaggaag acttggatga gttaaatatc   2040
agggacccgg aacacagagc tgttctcttg acagcagtgg agctgttaca agagtatgac   2100
agtaacagcg accagtcagg atcccaggag aagctgctcg ttgacagcca gggcctgagt   2160
ggatgctcac cccgagactc aggatgctac gaaagcagtg agaacctgga aaacggcaag   2220
actcggaaag ctagcctcct atctgccaag tcatccaccg agcccagctt gaagtctttt   2280
agcagaaacc agttgggcaa ttacccaaca ttgcctttaa tgaaatcagg ggatgcactg   2340
aagcagggac aggaggaggg caggctgggt ggtggccttg ccccagacac gtccaagagc   2400
tgtgacccac ctggtgtgac tggtttgaat aaaaaccgaa gaagcctccc agtttccatc   2460
tgccggagct gtgagaccct ggagggcccc cagactgtgg acacttggcc ccgatcccat   2520
tccctggatg accttcaagt ggagcctggt gctgagcaag acgtgcctac cgaggtgaca   2580
gaaccgcccc ctcagattgt acctgaagtg ccacagaaga cgaccgcctc ttccacgaag   2640
gcccagcccc tggagcgaga ctctgctgtc gacaatgcat tgctactgac ccaaagcaag   2700
agattttctg aacctcagaa attgacaact aagaaactgg agggctcaat cgcagcctct   2760
ggtcgcggcc tgtcaccccc tcagtgtttg cccagaaact atgatgctca gcctcctgga   2820
gctaaacacg gtttagcaag gacgcctctg gagggccaca gaaaaggaca cgagtttgaa   2880
ggaacacacc atcccctggg caccaaagaa ggggtagatg ctgagcagag aatgcagccc   2940
aaaattccat cacagcctcc acctgttcct gccaaaaaga gcagagaacg ccttgctaac   3000
```

```
ggactccacc ctgttcccat gggccccagt ggggccctcc ccagtcccga tgcgccatgc   3060
ctgccagtga aaaggggcag ccccgccagc cccaccagcc ctagcgactg tcccccagca   3120
ctggctccca ggcctctctc agggcaggcg cctggcagcc caccaagcac aaggccgccc   3180
ccctggctct cagagctccc cgagaacaca agcctccagg agcacggtgt gaagctgggc   3240
ccggctttga ccaggaaggt ctcctgtgcc cggggagtgg atctagaaac gctcactgaa   3300
aacaagctgc acgctgaagg catcgatctc acggaggagc cgtattctga taagcatggc   3360
cgctgtggga ttcctgaagc cctggtgcag agatacgcag aggacttgga tcagcccgag   3420
cgggacgtcg ccgccaacat ggaccagatc cgggtgaagc agcttcggaa gcagcaccgc   3480
atggcgattc caagtggtgg actcacggaa atctgccgaa agcccgtctc tcctgggtgc   3540
atttcgtctg tgtcagattg gctcatttcc atcggtctgc ccatgtacgc cggcaccctc   3600
tccaccgcgg gcttcagcac actgagccaa gtgccttctc tgtctcacac ttgccttcag   3660
gaggccggca tcacagagga gagacacata agaaagctcc tatctgcagc cagactcttc   3720
aaactgccgc caggccctga ggccatgtag ccaggcccgg aatgggcctc tctggacaag   3780
agccaccctt tcactgtgca tatgatgctg atgcaattcc tccatcatct ctggacgtgc   3840
agaccagatc cagaagaaag gcctggcgtg tggccaaaca gcgtgaaacc ttggcacagg   3900
actgaggatc ctctcctcca gaaaagcccc ctcgaggaaa taaattagtg cggttctctt   3960
tgacctccaa agacaagaca agcacttatt tttattttca gaagacaaaa gaaccaagat   4020
gccaactggc tgcgaatgct ctatctccag tctgtctctg tgtactggta gaggctggga   4080
ggagtagggg gcagcctgtt ccatttctga tagtgccctt gctcttctgt ctgtcatctt   4140
gcaggatgcc cgagggccag atgggcttag ctaggccaaa gtaacagact caagagttat   4200
tgtacattac tgaccacgct catttgttca aaagttagaa catctggctg caccaggaaa   4260
aaaaaaaaaa aaaagtcctg ttcttcttta gataaacaag agacattttc ataattgctt   4320
tctagcaatc agcttttatt tgccttaata taagctttta agcagttatc taactagtgt   4380
ccacaaccct gtaaccatac ttccacatct tcagcttagg cagacatcga acctctctgg   4440
gatgtttcca gcaaaagtga gcttttctaa tcgtctcatt gtaacatggc ttattttgta   4500
gaggtattca tcagccacac acttcatgtt ggtttttggt ttttaagcta actacaaatc   4560
tagtaaaaag ctatctgaaa ttcacaaata tcatgtgtgt gcgtgcgtgc gtgcgcgtgt   4620
gtgtctgtat tcatagtgac tgcttttggt tttaaccagt ttagtatcgt tactgtgtgg   4680
atcgtcgcgc tgcagtattg acttggaatc ctgaccatgt ccatcccaaa attcagtcct   4740
cagttaacgg atcatgtttg caaaaggtca ctgtgaggct gcatatttca gaaagatgtc   4800
cttaataagg gaagtcatgt ataagatgtt ttctaaaaga cttttcagta ttacaactaa   4860
tactattatt atccttcttt ttttatttag ataattcttt taatttaaac aaaggttcac   4920
tatggaacca gacaaatctc attagccatg tgttaagtat ttgctacttt aaattgtttt   4980
acaactgatt tcagcacatt ctatcctttt tttttttga aatggagttt cgctcttgtc   5040
acccaggctg gagtgcaatg gcacgatctt ggctcactgc aacctcagtc tcccaggttc   5100
aagtgattct cctgccttag cctcccgagt agctgggatt ataggcaccc accaccacgc   5160
ccagctaatt tttgtattat tagtagagac agggtttcac catgttggcc aggctggtct   5220
caaactcaac tcctgacctc aggtggtcca cccgcctcag cctcccaaag tgctgggatt   5280
acaggtgtga gccaccgcac ctggcctctg tcctctttta gtctagtgtc tggttttcta   5340
gcaaacagta aatttaaaca agtaaactat tatggtttcc attgcttaca aaatgatttt   5400
```

cctttacatt cttatcatga acactatttt aagcatcaaa tgcaatcatc taaaatataa 5460
aggtcaatca tttataatag aaacaccttg accacaagcc cttgattgaa cattttataa 5520
tatttcatct acttattaaa acaaataatt tcccttgggt tggaggggaa gtgatttcat 5580
aaattaatta gaaagccatc tttagcatat tgcttatgtc tggatccatg tttctgagga 5640
aaaagacatt ctcaggtgat gtattttttt catgcattag tatgcatttt taaaaaataa 5700
tgcatgtttc tttaataatt aattttcatc ttctataaga tgccatgtga agaagttgtg 5760
gaaatgtaga ataaaaagct aaagctgcca aatttctgtt gaactcttaa aaacagctca 5820
tgtttgtttg tcctctcggg ttgtggccta gcctatttgc aatgtaatga agctgcaggg 5880
ttcttgtata gctaaagcgt tcaatgcatt tcacgtgctg tggtggatgt gggtgctgta 5940
gacaggcttc ttctcttcct gctctcaaaa tacctcggct tgacatttgg acagatcctg 6000
tcattgttta agctgagcaa aaaaccacac aaaagttgtg taagagatga gataacaaag 6060
gagcgagaga aatctcatgt gaatttccaa gttttaattc gttctccatg aaggattttc 6120
atttcagtga aagtcgcagc agaagaggga actttctgga gtttttgaga atgccaaacc 6180
acatttttat cacacttctt tggaaatcaa tgcctttgca tagaaaatca aattcaggga 6240
ccacaaagaa ttttcagtgg gaatgtctag tctgaggggt ctgaggttgt ttttacttta 6300
ttgtgttgtt taaatatttt aaaaatatct ttagcgtttg gtcttttttt tttctgtaaa 6360
catttaattt ggtctgagaa aagctgaatg tttgggtgtg acgtttgact gaggtggatt 6420
ggggctgcct gtggacatta gtgaacaggt ggtaggcttc aggaatatcc agttttaatc 6480
agttgcattt ggtacagaat tttgagtaat ggtgaaaatt gttgtctttg gaaagcacaa 6540
aagaaacctg gaaaggcagt tcggctcagg tagctacaca taacattgtg tatgattttc 6600
acttcaaagc tgtctggaag gaaatgcagt cagctccagc tagtactatt tatgtaccca 6660
gataactaag atattgtttc atggccttgc cttagtcaga ggccctttc tctgtcctga 6720 acccccaggt atgggtgaaa ttggaaatta ctaatctatt ggaaatcagt tcctgacata 6780
gtaaagtttg ctttcataac tgcagcaaaa aaggtcaact tgccaagtca ctgctgccat 6840
gtgtgtactg tattattttc agaaaaaaat ataatagtct gagtccaagt tatcttgatt 6900
taaaattgat agagaaaaga aactgtcgag caagttatat aacaactaac aacattgcac 6960
tttctgtata tgaaatcaat atttaaataa cttatttttc tccattgctg ttcttaaaaa 7020
cattgtaagt agctgtaata taccagtacc aatatgttct tgcaattgct tcagcccaag 7080
aaagctgtgt attgttttaa aaattgtaaa aattattgtg atgattcatt tagcataaag 7140
agaggtggac ggaagggttt tcctatgtat caaaacttgt ctataattat gtcatctatg 7200
tacctagaaa aaagtaaata aatttcttca gttgaatatg 7240

<210> SEQ ID NO 15
<211> LENGTH: 3877
<212> TYPE: DNA
<213> ORGANISM: Homo sapiens

<400> SEQUENCE: 15
ggcggtcgcg cgcaggactc gagggcttct agccaccgtc cccgccagcg ccgcgccccg 60
ccacagggcg gcatgagccc acccgcggcc gcagccctag cgccctgctc ctccgcctgg 120
gcggcccggc tgcggtgacg gctctcgctg cccgactggg ggccatgaag ccgagtccgg 180
ccgggacggc gaaggagctg gagcctccgg cgccggcccg aggcgagcag cgcacggcgg 240
agcccgaggg gcgctggcgg gagaagggcg aggcagacac cgagcggcag cgcacccggg 300

```
agcggcagga ggccacgctg gccgggctgg cggagctgga gtacctgcgc cagcgccaag    360
agctgctggt caggggcgcc ctgcgcggcg ccgggggtgc gggagccgct gcgccccgcg    420
ctggggagct actgggggag gcggcgcagc gcagtcgcct ggaggagaag ttcttggagg    480
agaacatctt gctgctaaga aagcaattga actgtttgag gcgaagagat gctggtttgt    540
tgaatcagtt gcaagagctt gacaagcaga taagtgacct gagactggat gtagaaaaga    600
catctgaaga gcacctggag acagacagtc ggcctagctc agggttttat gagctgagtg    660
atggggcttc aggatccctt tccaattcct ctaactcggt gttcagtgag tgtttatcca    720
gttgtcattc cagcacctgc ttttgcagcc ccttggaggc gaccttgagt ctctcagatg    780
gttgccccaa atctgcagat ctcataggat tgttggaata taaagaaggc cactgtgaag    840
accaggcctc aggggcagtt tgccgttccc tctccacacc acaatttaat tcccttgatg    900
tcattgcaga tgtgaatccc aagtaccagt gtgatctggt gtctaaaaac gggaatgatg    960
tatatcgcta tcccagtcca cttcatgctg tggctgtgca gagcccaatg tttctccttt   1020
gtctgacggg caaccctctg agggaagagg acaggcttgg aaaccatgcc agtgacattt   1080
gcggtggatc tgagctagat gccgtcaaaa cagacagttc cttaccgtcc ccaagcagtc   1140
tgtggtctgc ttcccatcct tcatccagca agaaaatgga tggctacatt ctgagcctgg   1200
tccagaaaaa aacacaccct gtaaggacca acaaaccaag aaccagcgtg aacgctgacc   1260
ccacgaaagg gcttctgagg aacgggagcg tttgtgtcag agccccgggc ggtgtctcac   1320
agggcaacag tgtgaacctt aagaattcga aacaggcgtg tctgccctct ggcgggatac   1380
cttctctgaa caatgggaca ttctccccac cgaagcagtg gtcgaaagaa tcaaaggccg   1440
aacaagccga aagcaagagg gtgcccctgc cagagggctg cccctcaggc gctgcctccg   1500
accttcagag taagcacctg ccaaaaacgg ccaagccagc ctcgcaagaa catgctcggt   1560
gttccgccat tgggacaggg gagtccccta aggaaagcgc tcagctctca ggggcctctc   1620
caaaagagag tcctagcaga ggccctgccc cgccgcagga gaacaaagtt gtacagcccc   1680
tgaaaaagat gtcacagaaa aacagcctgc agggcgtccc cccggccact cctcccctgc   1740
tgtctacagc tttccccgtg gaagagaggc ctgccttgga tttcaagagc gagggctctt   1800
cccaaagcct ggaggaagcg cacctggtca aggcccagtt tatcccgggg cagcagccca   1860
gtgtcaggct ccaccggggc cacaggaaca tgggcgtcgt gaagaactcc agcctgaagc   1920
accgcggccc agccctccag gggctggaga acggcttgcc caccgtcagg gagaaaacgc   1980
gggccgggag caagaagtgt cgcttcccag atgacttgga tacaaataag aaactcaaga   2040
aagcctcctc caaggggagg aagagtgggg gcgggcccga ggctggtgtt cccggcaggc   2100
ccgcgggcgg gggccacagg gcggggagca gggcgcatgg ccacggacgg gaggcggtgg   2160
tggccaaacc taagcacaag cgaactgact accggcggtg gaagtcctcg gccgagattt   2220
cctacgaaga ggccctgagg agggcccggc gcggtcgccg ggagaatgtg gggctgtacc   2280
ccgcgcctgt gcctctgccc tacgccagcc cctacgccta cgtggctagc gactccgagt   2340
actcggccga gtgcgagtcc ctgttccact ccaccgtggt ggacaccagt gaggacgagc   2400
agagcaatta caccaccaac tgcttcgggg acagcgagtc gagtgtgagc gagggcgagt   2460
tcgtggggga gagcacaacc accagcgact ctgaagaaag cgggggctta atttggtccc   2520
agtttgtcca gactctgccc attcaaacgg taacggcccc agaccttcac aaccaccccg   2580
caaaaacctt tgtcaaaatt aaggcctcac ataacctcaa gaagaagatc ctccgctttc   2640
ggtctggctc tttgaaactg atgacgacgg tttgagtgac atcattggtg tagaaagttt   2700
```

```
gtgtgttttt ttttcttctc cctagttgcc aaaattaaaa aggtggtgtt ttcatttttg   2760
tataatactt taatggaatg ctttttaaaa aaatataaaa ccaaggtaaa ttattgtttc   2820
atcttcacgt atggatgcta gtgcctttaa tggaaggtaa agaatgtttt gctagttaga   2880
agtacatatt gaggttttaa tggtggtgat agtgagtttt gtggcaccag ctgtttttta   2940
ttttaaactt tctgagcatc cggcaaggta caggttttga tgttcaagtt ttattgggat   3000
aagatctttt gatcccaagg tcaggtggat ggaatttttg gatttatatt tgttccttga   3060
gtcttcaggg cagtgtctcc atgagggttt tcctgttgag ggcaccacaa tacaatagtg   3120
tgaagtaggt atgaggggca gtcattgtat tctatagttt ttttatgtag tctacatttc   3180
tcagatgtat ccccattcgg ttttattctc agaactgtta ctagactcat gacttggagg   3240
ccaaacctta aatccagaga tagcagcctc gatagggacc ttaaaaggat tcacaaaaac   3300
ttttgccaca cttggtgcct aggccctgtt cctaataacc ccttctaggg ccgtttatcc   3360
aacatttaga tgccttcttt tccctcccta atttgtagcc agtccaacct ttcattcctt   3420
ggaggattta gttttgggat aaaattttgg tccttgggca cagagacatt cactattaat   3480
gaagtaaccc ttgggcatga ctccaatccc agaattgctc actgagcgct atgccaccga   3540
agcgttgacc tgaacatatt agtgcaatcc agtccagatt ggacctttga tcctatgtgg   3600
aagggctgtt ttttaagaaa aaatttttgg taaacagtat tgtgtaaaat tgctttttgt   3660
ataccaatat atgcatgttt tgtgcatgag tagtacttgt gttgatactc ctgttgatgt   3720
taaattacta tataatataa acagtatgtg tttttatata tcattgtgta aatttaatat   3780
aacatatgca gtaataaacc atttgtttta ctgctgttaa gtttgttatt tgggtataaa   3840
accagatgtt tacacctgta aaaaaaaaaa aaaaaaa                            3877
```

<210> SEQ ID NO 16
<211> LENGTH: 2583
<212> TYPE: DNA
<213> ORGANISM: Homo sapiens

<400> SEQUENCE: 16

```
gtggaatccg gcgtgggctg gggggtccga gccgcggggg gcagtgccat gcacaagcac     60
cagcactgct gtaagtgccc tgagtgctat gaggtgaccc gcctggccgc cctgcggcgc    120
ctcgagcctc cgggctacgg cgactggcaa gtccccgacc cttacgggcc aggtgggggc    180
aacggcgcca gcgcgggtta tgggggctac agctcgcaga ccttgccctc gcaggcgggg    240
gccaccccca cccctcgcac caaggccaag ctcatcccca ccggccggga tgtggggccg    300
gtgcctccta agccagtccc gggcaagagc acccccaaac tcaacggcag cggccccagc    360
tggtggccag agtgcacctg taccaaccgg gactggtatg agcaggtgaa tggcagtgat    420
ggcatgttca aatatgagga aatcgtactt gagaggggca actctggcct gggcttcagt    480
atcgcaggtg gcatcgacaa tccccatgtc cctgatgacc ctggcatctt tattaccaag    540
attatccctg gtggagcagc tgccatggat gggaggctgg gggtgaatga ctgtgtgctg    600
cgggtgaatg aggtggacgt gtcggaggtg gtacacagcc gggcggtgga ggcgctgaag    660
gaggcaggcc ctgtggtgcg attggtggtg cggaggcgac agcctccacc cgagaccatc    720
atggaggtca acctgctcaa agggcccaaa ggcctgggtt tcagcattgc tgggggtatt    780
ggcaaccagc acatcccagg agacaacagc atctacatca ccaagatcat tgagggggt     840
gctgctcaga aggatggacg cctacagatt ggggaccggc tgctggcggt gaacaacacc    900
aatctgcagg atgtgaggca cgaggaagct gtggcctcac tgaagaacac atctgatatg    960
```

```
gtgtatttga aggtggccaa gccaggcagc ctccacctca acgacatgta cgctccccct   1020

gactacgcca gcacttttac tgccttggct gacaaccaca taagccataa ttccagcctg   1080

ggttatctcg gggctgtgga gagcaaggtc agctaccctg ctcctcctca ggttcccccc   1140

acccgctact ctcctattcc caggcacatg ctggctgagg aggacttcac cagagagcct   1200

cgcaagatca tcctgcacaa aggctccaca ggcctgggct tcaacatcgt aggaggagag   1260

gatggagaag gcatttttgt ctccttcatc ctggcaggag gcccagctga cctgagtggg   1320

gagctgcgca ggggagaccg gatcttatcg gtgaatggag tgaatctgag gaatgcaact   1380

catgagcagg ctgcagctgc tctgaaacgg gccggccagt cagtcaccat tgtggcccag   1440

tacagacctg aagaatacag tcgctttgaa tcgaagatac atgacttacg agaacaaatg   1500

atgaacagca gcatgagctc tgggtctggg tccctccgaa caagtgaaaa gaggtccttg   1560

tatgtcaggg ccctgtttga ttatgatcgg actcgggaca gctgcctgcc aagccagggg   1620

ctcagcttct cttatggtga cattctgcat gtcattaatg cctctgatga tgagtggtgg   1680

caggcaaggc tggtgacccc acacggagaa agtgagcaga tcggtgtgat ccccagtaag   1740

aagagggtgg aaaagaaaga aagagctcga ttgaaaactg tgaagttcca tgccaggacg   1800

gggatgattg agtctaacag ggacttcccg ggttaagtg acgattatta tggagcaaag   1860

aacctgaaag gacaagagga tgctattttg tcatatgagc cagtgacacg gcaagaaatt   1920

cactatgcaa ggcctgtgat catcctgggc ccaatgaagg accgagtcaa tgatgacctg   1980

atctccgaat ttccacataa atttggatcc tgtgtgccac atactacccg gcctcgacgt   2040

gataatgagg tggatggaca agactaccac tttgtggtgt cccgagaaca aatggagaaa   2100

gatattcagg acaacaagtt catcgaggcg ggccaattta atgataacct ctatgggacc   2160

agcatccagt cagtgcgggc agttgcagag aggggcaagc actgcatctt agatgtttcc   2220

ggcaatgcta tcaagagact gcagcaagca caactttacc ccattgccat tttcatcaag   2280

cccaagtcca ttgaagccct tatggaaatg aaccgaaggc agacatatga acaagcaaat   2340

aagatctatg acaaagccat gaaactggag caggaatttg gagagtactt tacagccatt   2400

gtacagggtg actcactgga agagatttat aacaaaatca aacaaatcat tgaggaccag   2460

tctgggcact acatttgggt cccatcccct gaaaaactct gaagaatccc ctccaaccat   2520

tctcttgtga acagaagaaa tcaagtccct cttccctcct ccctcttcat tcctgtcccc   2580

atg                                                                 2583
```

PERIPHERAL GENE EXPRESSION BIOMARKERS FOR AUTISM

REFERENCE TO RELATED APPLICATIONS

This application claims priority under Section 119(e) from U.S. Provisional Application Ser. No. 61/053,316, filed May 15, 2008, the contents of which are incorporated herein by reference.

STATEMENT OF GOVERNMENT SUPPORT

This invention was made with Government support of Grant No. MH064547, awarded by the National Institutes of Health. The Government has certain rights on this invention.

FIELD OF THE INVENTION

The invention relates to methods and materials for observing gene expression profiles that are associated with conditions such as autism.

BACKGROUND OF THE INVENTION

Autism comprises a behaviorally defined spectrum of disorders characterized by impairment of social interaction, deficiency or abnormality of speech development, and limited activities and interest. To standardize the diagnosis of autism spectrum disorders (ASD), diagnostic criteria have been defined by the World Health Organization (International Classification of Diseases, 10th Revision (ICD-10), 1992) and the American Psychiatric Association (*Diagnostic and Statistical Manual of Mental Disorders,* 4th edition, Text Revision. Washington DC, American Psychiatric Association, 2000 (DSM-IV)).

Genetic factors are significant determinants of autism spectrum disorders (see, e.g. Geschwind et al., (2007), Curr Opin Neurobiol, 17, 103-11). It has been shown that individuals with ASD carry chromosomal abnormality at a greater frequency than the general population (see, e.g. Veenstra-Vanderweele et al., (2004), Annu Rev Genomics Hum Genet, 5, 379-405; Vorstman et al., (2006), Mol Psychiatry, 11, 1, 18-28; Jacquemont et al. (2006), J Med Genet, 43, 843-9; Szatmari et al. (2007), Nat Genet, 39, 319-28; Sebat et al. (2007), Science, 316, 445-9). Maternally inherited duplication of 15q11-13 (dup15q) is the most common chromosomal abnormality in ASD. Over-expression of genes located in the duplicated region, including cytoplasmic FMR1 interacting protein 1 (CYFIP1), was shown in lymphoblastoid cell lines from ASD with dup15q (see, e.g. Nishimura et al. (2007), Hum Mol Genet, 16, 1682-98). A cryptic deletion at the boundary of the first exon and first intron of ataxin-2 binding protein-1 (A2BP1) was identified in a female with ASD, resulting reduced mRNA expression in the individual's lymphocytes (see, e.g. Martin et al. (2007), Am J Med Genet B Neuropsychiatr Genet). Loss of copy number of neurexin 1 (NRXN1) was identified in two females sibs with ASD but not in either parent (see, e.g. Szatmari et al. (2007), Nat Genet, 39, 319-28). Loss of copy number and decreased expression of SH3 and multiple ankyrin repeat domains 3 (SHANK3) were identified in four individuals with ASD (see, e.g. Jeffries et al., (2005), Am J Med Genet A, 137, 139-47; and Durand et al. (2007), Nat Genet, 39, 25-7). Recently, a common 'C' allele in the promoter region of met protooncogene (MET) was shown to have strong association with ASD (see, e.g. Campbell et al., (2006), Proc Natl Acad Sci USA, 103, 16834-9). The 'C' variant causes a twofold decrease in MET promoter activity. These findings suggest that dysregulation of gene expression due to variation in genomic sequence may affect susceptibility or cause ASD.

Transcriptome profiling using DNA microarray represents an efficient manner in which to uncover unanticipated relationship between gene expression alterations and neuropsychiatric diseases (see, e.g. Geschwind, D. H. (2003), Lancet Neurol, 2, 275-82; and Mimics et al., (2006), Biol Psychiatry, 60, 163-76). Several studies have suggested that blood-derived cells can be used to identify candidate genes in neuropsychiatric diseases, including ASD. Hu et al. analyzed gene expression profiling of lymphoblastoid cells from monozygotic (MZ) twins discordant in severity of ASD (see, e.g. Hu et al., (2006), BMC Genomics, 7, 118). Several genes were differentially expressed between MZ twins, suggesting candidate genes for ASD may be differentially expressed in lymphoblastoid cells from individuals with ASD. We previously analyzed genome-wide expression profiles of lymphoblastoid cells from ASD with full mutation of FMR1 (FMR1-FM) or dup15q, each of which account for 1-2% of ASD cases in large series, and non-autistic controls (see, e.g. Nishimura et al. (2007), Hum Mol Genet, 16, 1682-98). The gene expression profiles clearly distinguished ASD from controls and separated individuals with ASD based on their genetic etiology. The expression profiles also revealed shared pathways between ASD with FMR1-FM and ASD with dup15q.

While progress in understanding genetic factors associated with autism spectrum disorders has been made, specific assays for constellations of genetic factors associated with autism spectrum disorders would be a significant benefit to medical personnel. Tests for genetic factors associated with autism spectrum disorders are valuable for the diagnosis of this syndrome, as well as useful for research on the genetic mechanisms involved in autism spectrum disorders. Moreover, while there is no known medical treatment for autism, success has been reported for early intervention with behavioral therapies. In this context, an assay would facilitate the early identification of the disease, one now typically diagnosed between ages three and five. Thus, there is a need for methods and materials that can be used to identify subjects having genetic polymorphisms associated with autism spectrum disorders.

SUMMARY OF THE INVENTION

Autism spectrum disorder is a heterogeneous condition and is likely to result from the combined effects of multiple, subtle genetic changes interacting with environmental factors. The disclosure provided herein shows that genome-wide expression profiling of lymphoblastoid cells from ASD subjects distinguishes different forms of ASD and reveals shared pathways. This disclosure identifies genes dysregulated in common among the idiopathic ASD as well as ASD with known genetic disorders. These results provide evidence that studies of gene expression in cells such as blood derived lymphoblastoid cells can be used for example in assays designed to identify and characterize specific polymorphisms associated with ASD.

The invention disclosed herein has a number of embodiments. One illustrative embodiment is a method of identifying a human cell having a gene expression profile associated with autism spectrum disorders comprising: observing an expression profile of at least one gene in the cell whose expression is shown to be dysregulated in autism spectrum disorders (e.g. one or more of the genes disclosed in the Tables below); wherein an expression profile of this gene that is at least two, three or four standard deviations from a mean expression profile of the gene in a control cell identifies the human cell as having a gene expression profile associated with autism spectrum disorders. Typically, such methods are used to facilitate the diagnosis of an autism spectrum disorder. For example, in certain embodiments of the invention, the cell examined by this method is obtained from an individual identified as being predisposed to and/or exhibiting a behavior associated with autism spectrum disorders, while the control cell is one obtained from an individual previously identified as not being predisposed to and/or exhibiting a behavior associated with autism spectrum disorders. In certain embodiments, the cell examined by this method and the control cell are obtained from individuals who are related as siblings or as a parent and a child. Typically one or more cells used in these methods are leukocytes obtained from the peripheral blood.

In illustrative methods for observing an expression profile of one or more genes, mRNA expression is observed, for example by using a using quantitative PCR (qPCR) technique. In certain embodiments of the invention, the expression profile of the genes in is observed using a microarray of polynucleotides. Alternatively, polypeptide expression is observed and quantified, for example by using an antibody specific for a polypeptide encoded by a gene whose expression is shown to be dysregulated in autism spectrum disorders (e.g. using an ELISA technique or the like). Alternatively, the expression profile of a gene is observed using a Southern blotting technique (e.g. to identify deletions and/or duplications in genomic sequences).

Embodiments of the invention include kits comprising, for example, a first container, a label on said container, and a composition contained within said container; wherein the composition includes polymerase chain reaction (PCR) primer effective in the quantitative real time analysis of the mRNA expression levels of one or more genes disclosed herein whose expression is shown to be dysregulated in autism spectrum disorders (e.g. one or more of the genes disclosed in the Tables below); the label on said container, or a package insert included in said container indicates that the composition can be used to observe expression levels of these genes in at least one type of human leukocyte; a second container comprising a pharmaceutically-acceptable buffer; and instructions for using the PCR primer to obtain an expression profile of the one or more genes. Optionally the kit comprises 2, 3, 4, 5, 6, 7, 8, 9 or 10 polymerase chain reaction (PCR) primers effective in the quantitative real time analysis of the mRNA expression levels of different genes disclosed in the Tables below.

In some embodiments of the invention, one can observe an expression profile of at least, 2, 3, 4, 5, 6, 7, 8, 9 or 10 or more genes whose expression is shown to be dysregulated in autism spectrum disorders (e.g. using microarray technologies). In certain embodiments of the invention, the method is performed on a plurality of individuals and the results are then categorized based upon similarities or differences in their gene expression profiles. Optionally, the expression profile(s) is observed and/or collected and/or stored using a computer system comprising a processor element and a memory storage element adapted to process and store data from one or more expression profiles (e.g. in a library of such profiles). In this context, certain embodiments of the invention comprise an electronically searchable library of profiles, wherein the profiles include an individual's gene expression data in combination with other diagnostic data, for example assessments of behavior associated with autism spectrum disorders.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 8 shows differentially expressed probes identified by microarray analysis. Venn diagram shows the number of probes differentially expressed in idiopathic ASD (N=15), ASD with FMR1-FM (N=6) and ASD with dup15q (N=7) compared with control (N=15). 124 probes, representing 92 genes were identified in common in all three forms of ASD.

DETAILED DESCRIPTION OF THE INVENTION

Figure 1:
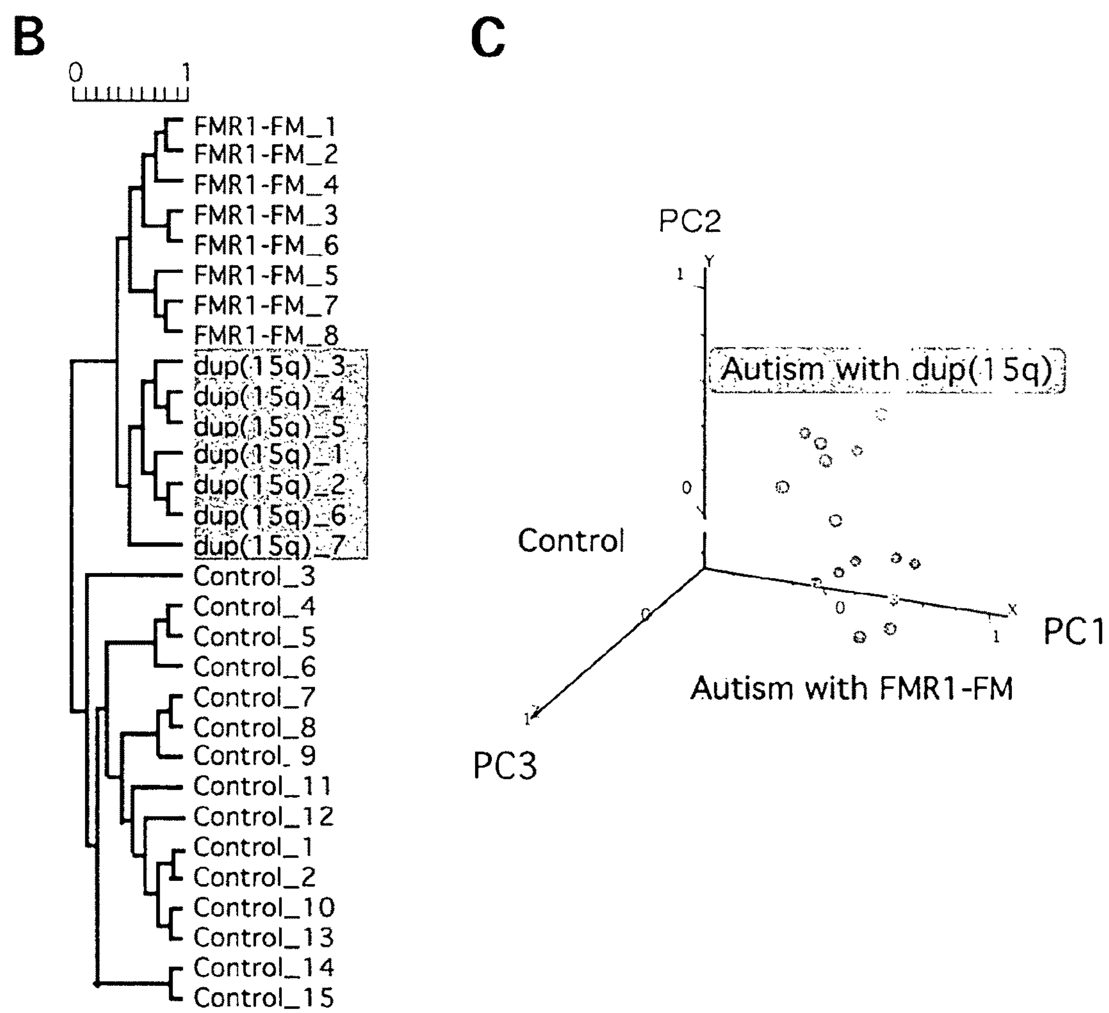
FIG. 1 provides data showing that hierarchical clustering and principal component analysis differentiate individuals based on their etiology. ANOVA identified 293 probes with significantly different expression between autism with FMR1-FM (n=8), autism with dup(15q) (n=7) and control (n=15). The probes were subjected to hierarchical clustering and principal component analysis (PCA). A) Hierarchical clustering of the 30 individuals and genes. Each row represents an individual and each column represent one of the 293 probes. A pseudo-colored representation of the relative intensity was shown, such that a red color indicates high expression and green color low expression, with the scale shown below. Relative distance of each probe (horizontal axis) and individuals (vertical axis) are also demonstrated. B) Enlargement of the hierarchical clustering dendrogram of the sample in A). All 8 autism with FMR1-FM, 7 autism with dup(15q), and 15 controls correctly clustered within their etiological categories. The scale showed the Spearman rank correlation coefficient used to construct the dendrogram. C) PCA of the expression profile of the 293 probes from 30 individuals. Shown here were three principle components. Autism with FMR1-FM were depicted as red, autism with dup(15q) as green and control as blue. The individuals were clustered closely according to their genetic etiologies.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. It must also be noted that as used herein and in the appended claims, the singular forms "a", "and", and "the" include plural referents unless the context clearly dictates otherwise. All numbers recited in the specification and associated claims that refer to values that can be numerically characterized with a value other than a whole number (e.g. a number of standard deviations from a mean) are understood to be modified by the term "about".

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Illustrative Embodiments of the Invention

Autism is part of a spectrum of disorders including Asperger syndrome (AS) and other pervasive developmental disorders (PPD). The term "autism" is used herein according to its art accepted meaning and encompasses conditions of impaired social interaction and communication with restricted repetitive and stereotyped patterns of behavior, interests and activities present before the age of 3, to the extent that health may be impaired. AS is typically distinguished from other autistic disorders by a lack of a clinically significant delay in language development in the presence of the impaired social interaction and restricted repetitive behaviors, interests, and activities that characterize the autism-spectrum disorder (ASD). PPD-NOS (PPD, not otherwise specified) is typically used to categorize children who do not meet the strict criteria for autism but who come close, either by manifesting atypical autism or by nearly meeting the diagnostic criteria in two or three of the key areas.

In about 5 percent of autism cases, another disorder is also present (i.e. an autism-associated disorder). Nearly one-third of those with autism also show signs of epilepsy by adulthood. About 6 percent of those with autism also have tuberous sclerosis, a disorder that shares many symptoms with autism, including seizures that result from lesions, or cuts on the brain. About 25 percent of persons with autism also have some degree of mental retardation. About 2 percent of those with autism also have Fragile X syndrome, the most common inherited form of mental retardation.

The disclosure provided herein identifies genes that are observed to be Dysregulated in Autism Spectrum Disorders. In the instant disclosure, these genes are collectively referred to as "DASD genes" for purposes of convenience. Human DASD genes useful in embodiments of the invention are shown for example in Tables 1-6 below as well as the Tables found in Nishimura et al., Human Molecular Genetics 2007 16(14): 1682-1698 (the contents of which are incorporated by reference), disclosure which includes information such as the gene name, gene symbol, RefSeq number, and gene locus for these genes. Because the genes disclosed herein are known in the art and further because of the high level of skill possessed by artisans in this technical field, the information as disclosed herein and/or in Nishimura et al., Human Molecular Genetics 2007 16(14): 1682-1698 places artisans in possession of the polynucleotide and polypeptide sequences of these genes by providing them with the specific disclosure which allows them to retrieve this sequence information from library sources such as GenBank and/or UniProtKB/Swiss-Prot with only minimal effort. As is know in the art, GenBank® is the NIH genetic sequence database, an annotated collection of all publicly available DNA sequences; and UniProtKB/Swiss-Prot is a curated protein sequence database which provides a high level of annotation (e.g. technical references describing the features of these genes), a minimal level of redundancy and high level of integration with other databases. The DASD gene polynucleotide and polypeptide sequence information can be retrieved from GenBank and/or UniProtKB/Swiss-Prot library databases by, for example, querying these databases using the DASD disclosure information as provided herein and/or incorporated by reference into the instant specification (e.g. the gene name, gene symbol, gene RefSeq number, gene locus etc.).

As disclosed in detail below, this disclosure provides methods and materials that can be used in the diagnosis and treatment of autism spectrum disorders, and autism-associated disorders. In typical embodiments of the invention one observes an expression profile of at least one gene disclosed herein, wherein a dysregulated expression profile provides evidence of an autism spectrum disorder. Embodiments of invention can be used for example in the diagnosis of (including a predisposition to), and/or treatment of autism spectrum disorders such as Asperger syndrome, pervasive developmental disorder, mental retardation, speech delay, and other associated psychiatric and neurological phenomena.

The invention disclosed herein has a number of embodiments. One embodiment is a method of identifying a individual having a gene expression profile associated with autism spectrum disorders comprising: observing an expression profile of at least one DASD gene in a test cell (e.g. mRNA expression in a peripheral blood leukocyte obtained from an individual suspected of having an autism spectrum); wherein an expression profile of a DASD gene in the test cell that is at least two standard deviations from a mean expression of the DASD gene as observed in a control cell (e.g. a peripheral blood leukocyte obtained from a non-effected sibling) identifies the test cell as having a gene expression profile associated with autism spectrum disorders. In typical embodiments of the invention, the gene expression profile comprises data relating to the levels of mRNA expressed by a DASD gene in the cell. In embodiments of the invention, gene expression can be quantified using a comparison of expression in a test cell relative to a mean expression observed in a control cell. For example, in some embodiments of the invention, the expression of a DASD gene is identified as being associated with autism spectrum disorders when it is at least three, four or five standard deviations from the mean expression of the gene observed in a control cell. In related embodiments of the invention, the expression of a DASD gene is identified as being associated with autism spectrum disorders when the expression level is at least 20, 30, 40, 50, 60 or 70% above or below the expression level of that gene in a control cell.

Typically in such methods of observing an expression profile of a DASD gene, mRNA expression is observed, for example by using a using quantitative PCR (qPCR) technique. In certain embodiments of the invention, the expression profile of the DASD gene in the test cell is observed using a microarray of polynucleotides. Alternatively, DASD polypeptide expression is observed, for example by using an antibody specific for a polypeptide encoded by a DASD gene (e.g. using an ELISA technique or the like). Alternatively, the expression profile is observed using Southern blotting (e.g. to identify deletions in or duplications of DASD genomic sequences).

Autism spectrum disorder is a heterogeneous condition that appears to result from the combined effects of multiple, subtle genetic changes interacting with environmental factors. Consequently, in some embodiments of the invention, an expression profile of at least, 2, 3, 4, 5, 6, 7, 8, 9 or 10 or more DASD genes are observed in order to obtain a detailed profile of these multiple genetic changes and/or to stratify individuals into subsets of autism spectrum disorders (e.g. using microarray technologies). For example, in certain embodiments of the invention, the method is performed on a plurality of individuals and then segregated based upon similarities or differences in their gene expression profiles. Optionally, the expression profile(s) of the test mammalian cell is observed using a computer system comprising a processor element and a memory storage element adapted to process and store data from one or more expression profiles (e.g. in a library of such profiles). In this context, one embodiment of the invention comprises an electronically searchable library of profiles, wherein the profiles include individual's gene expression data in combination with other diagnostic data, for example assessments of whether the individual exhibits behavior associated with an autism spectrum disorder (e.g. behavioral test data such as that obtained in an Autism Diagnostic Interview (ADI-R)).

In typical embodiments of the invention, these methods are used to facilitate diagnosis of an autism spectrum disorder in an individual. In this context, a cell examined in the methods of the invention can be a leukocyte obtained from the peripheral blood of the individual. In certain embodiments of the invention, the test cell is obtained from an individual previously identified as exhibiting a behavior associated with autism spectrum disorders. In some embodiments of the invention, the test cell is obtained from an individual identified as having a family member previously identified as exhibiting a behavior associated with autism spectrum disorders. In typical embodiments, the control mammalian cell is obtained from an individual previously identified as not exhibiting a behavior associated with autism spectrum disorders. Embodiments of the invention include methods which perform a further diagnostic procedure for autism spectrum disorders on an individual identified as having a gene expression profile associated with autism spectrum disorders (e.g. a procedure following standard validating measures, such as the Autism Diagnostic Interview (ADI-R)). Optionally, the test mammalian cell and the control mammalian cell are obtained from individuals who are related as siblings or as a parent and a child.

Embodiments of the invention further include a kit comprising: a first container, a label on said container, and a composition contained within said container; wherein the composition includes polymerase chain reaction (PCR) primer effective in the quantitative real time analysis of the mRNA expression levels of one or more DASD genes, the label on said container, or a package insert included in said container indicates that the composition can be used to observe expression levels of one or more DASD genes in at least one type of human leukocyte; a second container comprising a pharmaceutically-acceptable buffer; and instructions for using the PCR primer to obtain an expression profile of the one or more DASD genes. Optionally the kit comprises 2, 3, 4, 5, 6, 7, 8, 9 or 10 polymerase chain reaction (PCR) primers effective in the quantitative real time analysis of the mRNA expression levels of different DASD genes.

In certain embodiments of the invention, a kit further comprises a computer readable a memory storage element adapted to process and store data from one or more expression profiles. In some of these embodiments, the memory storage element organizes expression profile data into a format adapted for electronic comparisons with a library of expression profile data.

Embodiments of the invention further comprise, for example, methods of assessing the response of a subject to a treatment of an autism spectrum disorder, or an autism-associated disorder (e.g. treatment comprising the administration of a therapeutic agent), the method comprising detecting altered DASD gene or polypeptide expression in a sample from the treated subject, the presence of the alteration being indicative of a response to the treatment.

As noted above, embodiments of the invention compare DASD gene expression in a test cell (e.g. a cell obtained from an individual suspected of having an autism spectrum disorder) with DASD gene expression in a normal cell (e.g. a cell obtained from an individual not having an autism spectrum disorder) in order to determine if the test cell exhibits altered DASD gene expression. In addition to using normal cells as a comparative sample for DASD expression, in certain situations one can also use a predetermined normative value such as a predetermined normal sequence, and/or level of DASD mRNA or polypeptide expression (see, e.g., Grever et al., J. Comp. Neurol. 1996 Dec. 9; 376(2):306-14 and U.S. Pat. No. 5,837,501) to evaluate levels of DASD expression in a given sample. The term "status" in this context is used according to its art accepted meaning and refers to the condition or state of a gene and its products. Typically, skilled artisans use a number of parameters to evaluate the condition or state of a gene and its products. These include, but are not limited to the level, sequence of and biological activity of expressed gene products (such as DASD mRNA, polynucleotides and polypeptides). In certain embodiments of the invention, the expression of a DASD gene product is characterized by observing how far the expression level of a DASD mRNA in a sample deviates from a mean expression level of that mRNA in control cells in order to obtain a statistical measure of precision. Standard deviation is a measure of the variability or dispersion of a data set, in this case, the levels of mRNA expression of selected genes. Standard deviation in this context allows determinations of how spread out a set of expression values is and how a given sample fits into such analyses. Illustrative statistical methods for determining such values can be found for example in Cui et al., Genome Biol. (2003) 4:210; Tusher et al., Proc. Natl Acad. Sci. USA (2001) 98:5116-5121; Jeffery et al., BMC Bioinformatics (2006) 7:359; and Breitling et al., FEBS Lett. (2004) 573:83-92, the contents of which are incorporated by reference.

As discussed in detail below, the status of a DASD gene can be analyzed by a number of techniques that are well known in the art. Typical protocols for evaluating the status of the DASD gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). The status of a DASD gene in a biological sample is evaluated by various methods utilized by skilled artisans including, but not limited to genomic Southern analysis (to examine, for example perturbations in DASD genomic sequences), Northern analysis and/or PCR analysis of DASD mRNA (to examine, for example alterations in the polynucleotide sequences or expression levels of DASD mRNAs), and, Western and/or immunohistochemical analysis (to examine, for example alterations in polypeptide sequences, alterations in expression levels of DASD proteins etc.). Detectable DASD polynucleotides include, for example, a DASD gene or fragment thereof, DASD mRNA, alternative splice variants, DASD mRNAs, and recombinant DNA or RNA molecules comprising a DASD polynucleotide.

By examining a biological sample obtained from an individual (e.g. a peripheral blood leukocyte) for evidence altered gene expression of one or more genes whose expression is dysregulated in individuals diagnosed with autism spectrum disorders, medical personnel can obtain information useful in the identification, treatment and/or management of these disorders. Typically, the methods comprise detecting in a sample from a subject the presence of altered DASD gene expression, the presence of the alteration being indicative of the presence of, or predisposition to autism, an autism spectrum disorder, or an autism-associated disorder. In this context, "altered gene expression" encompasses altered DASD mRNA and/or polypeptide levels; altered DASD polynucleotide and polypeptide sequences, altered DASD genomic DNA methylation patterns and the like, alterations that are typically absent in individuals not having an autism spectrum disorder. In such examinations, the status of one or more DASD polynucleotides and/or polypeptides in a biological sample of interest (e.g. a peripheral blood leukocyte obtained from an individual suspected of having an autism spectrum disorder) can be compared to a standard or control, for example, or to the status of the DASD polynucleotide(s) or polypeptide(s) in a corresponding normal sample (e.g. a peripheral blood leukocyte obtained from a non-effected sibling or another individual not having a autism spectrum disorder). An alteration in the status of DASD gene expression in the biological sample (as compared to a control or standardized sample and/or value) then provides evidence of an autism spectrum disorder.

As noted above, embodiments of invention provide methods that comprise for example observing the expression status of one or more DASD genes in a subject in order to obtain diagnostically and/or prognostically useful information. Such methods typically use a leukocyte obtained from a subject to assess the status of a DASD gene. The sample may be any biological sample derived from a subject, which contains nucleic acids or polypeptides. Examples of such samples include fluids, tissues, cell samples, organs, biopsies, etc. Most preferred samples are blood and other leukocyte containing tissues etc. Pre-natal diagnosis may also be performed by testing for example fetal cells or placental cells. Any biological sample from which DASD genes and/or the products of DASD genes can be isolated is suitable. The sample may be collected according to conventional techniques and used directly for diagnosis or stored. The sample may be treated prior to performing the method, in order to render or improve availability of nucleic acids and/or polypeptides for testing. Treatments include, for example, lysis (e.g., mechanical, physical, chemical, etc.), centrifugation, etc. Also, the nucleic acids and/or polypeptides may be pre-purified or enriched by conventional techniques, and/or reduced in complexity. Nucleic acids and polypeptides may also be treated with enzymes or other chemical or physical treatments to produce fragments thereof.

The isolation of biological samples from a subject which contain nucleic acids and/or polypeptides is well know in the art. For example, certain embodiments isolate leukocytes from the circulating blood in order to assess the status of DASD genes in these cells. In such embodiments, blood is typically collected from subjects into heparinized blood collection tubes by personnel trained in phlebotomy using sterile technique. The collected blood samples can be divided into aliquots and centrifuged, and the buffy coat layer can then be removed (this fraction contains the leukocytes). RNA can then be extracted using a commercial RNA purification kit (e.g. RNeasy; Qiagen, Valencia, Calif.). RNA quality can be determined, for example, with an A260/A280 ratio and capillary electrophoresis on an apparatus such as an Agilent 2100 Bioanalyzer automated analysis system (Agilent Technologies, Palo Alto, Calif.).

In typical embodiments of the invention, a sample is contacted with reagents such as probes, primers or ligands (e.g. antibodies) in order to assess the presence of altered gene expression of a DASD gene. Such methods may be performed by a wide variety of apparatuses used in the art, such as a plate, tube, well, glass, etc. In specific embodiments, the contacting is performed on a substrate coated with the reagent, such as a nucleic acid array or a specific ligand (e.g. antibody) array. The substrate may be solid or semi-solid substrate such as any support comprising glass, plastic, nylon, paper, metal, polymers and the like. The substrate may be of various forms and sizes, such as a chip, a slide, a membrane, a bead, a column, a gel, etc. The contacting may be made under any condition suitable for a complex to be formed between the reagent and the nucleic acids or polypeptides of the sample.

A wide variety of methods known in the art can be used to examine the expression of DASD polypeptides and polynucleotides in cells such as peripheral blood leukocytes. For example, certain embodiments of methods which examine DASD polynucleotides and polypeptides in such cells are analogous to those methods from well-established diagnostic assays known in the art such as those that observe the expression of biomarkers such as prostate specific antigen (PSA) polynucleotides and polypeptides. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA expression, the DASD polynucleotides identified herein can be utilized in the same way to observe DASD overexpression or underexpression or other alterations in these genes. Similarly, just as PSA polypeptides are used to generate antibodies specific for PSA which can then be used to observe the presence and/or the level of PSA proteins in methods to monitor PSA protein expression (see, e.g., Stephan et al., Urology 55(4):560-3 (2000)) in prostate cells (see, e.g., Alanen et al., Pathol. Res. Pract. 192(3):233-7 (1996)), the DASD polypeptides described herein can be utilized to generate antibodies for use in detecting DASD expression in peripheral blood leukocytes and the like. Accordingly, the status of DASD gene products provides information useful for predicting a variety of factors including the presence of and/or susceptibility to autism spectrum disorders. As discussed in detail herein, the status of DASD gene products in patient samples can be analyzed by a variety protocols that are well known in the art including immunohistochemical analysis, the variety of Northern blotting techniques including in situ hybridization, RT-PCR analysis (e.g. quantitative RT-PCR), Western blot analysis, polynucleotide and polypeptide microarray analysis and the like.

Exemplary embodiments of the invention include methods for identifying a cell that overexpresses or underexpresses DASD polynucleotides and/or polypeptides. One such embodiment of the invention is an assay that quantifies the expression of the DASD gene in a cell by detecting the absence/presence and/or relative levels of DASD mRNA concentrations in the cell. Methods for the evaluation of particular mRNAs in cells are well known and include, for example, hybridization assays using complementary DNA probes (such as in situ hybridization using labeled DASD riboprobes, Northern blot and related techniques) and various nucleic acid amplification assays (such as qPCR using complementary primers specific for DASD, and other amplification type detection methods, such as, for example, branched DNA, SISBA, TMA and the like).

Embodiments of the invention include methods for detecting a DASD mRNA in a biological sample by generating cDNA in the sample by reverse transcription using at least one primer; amplifying the cDNA so produced using an DASD polynucleotides as sense and antisense primers to amplify DASD cDNAs therein; and detecting the presence of the amplified DASD cDNA. One exemplary PCR method that can be used in embodiments of the invention is a real-time quantitative PCR (qPCR) assay. Such real-time assays provide a large dynamic range of detection and a highly sensitive methods for determining the amount of DNA template of interest. When qPCR follows a reverse transcription reaction, it can be used to quantify RNA templates as well. In addition, qPCR makes quantification of DNA and RNA much more precise and reproducible because it relies on the analysis of PCR kinetics rather than endpoint measurements. Illustrative qPCR assays are disclosed for example in U.S. Patent Application Nos.: 2006/0008809; 2003/0219788; 2006/0051787; and 2006/0099620, the contents of which are incorporated by reference.

Some embodiments of the invention can use next-generation sequencing technologies for the expression profiling of DASD genes, for example those that are commercially available from vendors such as APPLIED BIOSYSTEMS and ILLUMINA. Typically in these embodiments, one can count the number of copies of each DASD gene that is expressed in order to provide assays that quantify the expression levels of all mRNA molecules in a cell. Because such methods are based on sequencing and not hybridization, they can provide an unbiased, probe-less measurement of all mRNA molecules in a sample. Illustrative aspects of such technologies are disclosed for example in U.S. Patent No. 20080262747, the contents of which are incorporated by reference.

Another embodiment of the invention is a method of detecting DASD genes having altered copy numbers (i.e. genes having a copy numbers that is above or below the number of copies observed in cells obtained from normal individuals) and/or another chromosomal rearrangement in a biological sample by isolating genomic DNA from the sample; amplifying the isolated genomic DNA using DASD polynucleotides as sense and antisense primers; and detecting the presence of the altered DASD gene. Any number of appropriate sense and antisense probe combinations can be designed from the nucleotide sequence provided for the DASD and used for this purpose.

The invention also provides assays for detecting the presence of a DASD protein in a tissue or other biological sample and the like. Methods for detecting a DASD-related protein are also well known and include, for example, immunoprecipitation, immunohistochemical analysis, Western blot analysis, molecular binding assays, ELISA, ELIFA and the like. For example, a method of detecting the presence of a DASD-related protein in a biological sample comprises first contacting the sample with a DASD antibody, a DASD-reactive fragment thereof, or a recombinant protein containing an antigen binding region of a DASD antibody; and then detecting the binding of DASD-related protein in the sample. Optionally, DASD polypeptide expression is measured in a tissue microarray.

In another embodiment of the invention, one can evaluate the status DASD nucleotide and amino acid sequences in a biological sample in order to identify perturbations in the structure of these molecules. These perturbations can include insertions, deletions, substitutions, duplications and the like in the coding and regulatory regions of the DASD gene. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of an DASD 5' or 3' regulatory enhancer and/or promoter sequence may provide evidence of dysregulated expression. Such assays therefore have diagnostic and predictive value where a mutation in DASD is indicative of dysregulated expression.

A wide variety of assays for observing perturbations in nucleotide and amino acid sequences are well known in the art. For example, the size and structure of nucleic acid or amino acid sequences of DASD gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 and 5,952,170, the contents of which are incorporated by reference).

The mutation in a DASD gene may be a single base substitution mutation resulting in an amino acid substitution, a single base substitution mutation resulting in a translational stop, an insertion mutation, a deletion mutation, or a gene rearrangement. The mutation may be located in an intron, an exon of the gene, or a promotor or other regulatory region which affects the expression of the gene. Screening for mutated nucleic acids can be accomplished by direct sequencing of nucleic acids. Nucleic acid sequences can be determined through a number of different techniques which are well known to those skilled in the art, for example by chemical or enzymatic methods. The enzymatic methods rely on the ability of DNA polymerase to extend a primer, hybridized to the template to be sequenced, until a chain-terminating nucleotide is incorporated. The most common methods utilize dideoxynucleotides. Primers may be labelled with radioactive or fluorescent labels. Various DNA polymerases are available including Klenow fragment, AMV reverse transcriptase, *Thermus aquaticus* DNA polymerase, and modified T7 polymerase.

Ligase chain reaction (LCR) is yet another method of screening for mutated nucleic acids. LCR can be carried out in accordance with known techniques and is especially useful to amplify, and thereby detect, single nucleotide differences between two DNA samples. In general, the reaction is carried out with two pairs of oligonucleotide probes: one pair binds to one strand of the sequence to be detected; the other pair binds to the other strand of the sequence to be detected. The reaction is carried out by, first, denaturing (e.g., separating) the strands of the sequence to be detected, then reacting the strands with the two pairs of oligonucleotide probes in the presence of a heat stable ligase so that each pair of oligonucleotide probes hybridize to target DNA and, if there is perfect complementarity at their junction, adjacent probes are ligated together. The hybridized molecules are then separated under denaturation conditions. The process is cyclically repeated until the sequence has been amplified to the desired degree. Detection may then be carried out in a manner like that described above with respect to PCR.

Southern hybridization is also an effective method of identifying differences in sequences. Hybridization conditions, such as salt concentration and temperature can be adjusted for the sequence to be screened. Southern blotting and hybridizations protocols are described in Current Protocols in Molecular Biology (Greene Publishing Associates and Wiley-Interscience), pages 2.9.1-2.9.10. Probes can be labelled for hybridization with random oligomers (primarily 9-mers) and the Klenow fragment of DNA polymerase. Very high specific activity probe can be obtained using commercially available kits such as the Ready-To-Go DNA Labelling Beads (Pharmacia Biotech), following the manufacturer's protocol. Briefly, 25 ng of DNA (probe) is labelled with $^{32}$P-dCTP in a 15 minute incubation at 37° C. Labelled probe is then purified over a ChromaSpin (Clontech) nucleic acid purification column.

Determinations of the presence of the polymorphic form of a DASD protein can also be carried out, for example, by isoelectric focusing, protein sizing, or immunoassay. In an immunoassay, an antibody that selectively binds to the mutated protein can be utilized (for example, an antibody that selectively binds to the mutated form of DASD encoded protein). Such methods for isoelectric focusing and immunoassay are well known in the art. For example, changes resulting in amino acid substitutions, where the substituted amino acid has a different charge than the original amino acid, can be detected by isoelectric focusing. Isoelectric focusing of the polypeptide through a gel having an ampholine gradient at high voltages separates proteins by their pI. The pH gradient gel can be compared to a simultaneously run gel containing the wild-type protein. Protein sizing techniques such as protein electrophoresis and sizing chromatography can also be used to detect changes in the size of the product.

As an alternative to isoelectric focusing or protein sizing, the step of determining the presence of the mutated polypeptides in a sample may be carried out by an antibody assay with an antibody which selectively binds to the mutated polypeptides (i.e., an antibody which binds to the mutated polypeptides but exhibits essentially no binding to the wild-type polypeptide without the polymorphism in the same binding conditions). Antibodies used to selectively bind the products of the mutated genes can be produced by any suitable technique. For example, monoclonal antibodies may be produced in a hybridoma cell line according to the techniques of Kohler and Milstein, Nature, 265, 495 (1975), which is hereby incorporated by reference. A hybridoma is an immortalized cell line which is capable of secreting a specific monoclonal antibody. The mutated products of genes which are associated with autism may be obtained from a human patient, purified, and used as the immunogen for the production of monoclonal or polyclonal antibodies. Purified polypeptides may be produced by recombinant means to express a biologically active isoform, or even an immunogenic fragment thereof may be used as an immunogen. Monoclonal Fab fragments may be produced in *Escherichia coli* from the known sequences by recombinant techniques known to those skilled in the art.

Additionally, one can examine the methylation status of the DASD gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Embodiments of the invention include compositions that can be used for example in various methods disclosed herein. Compositions useful in the methods disclosed herein typically include for example one or more DASD nucleic acid molecules designed for use as a probe such as a PCR primer in a method used to monitor DASD mRNAs or genomic sequences in a cell. Optionally, the probe or primer has 8, 9, 19, 11, 12, 13, 14, 15, 16, 17, 18, 19, 20, 21, 22, 23, 24, 25 or more nucleotides that are complementary to a DASD mRNA. In certain embodiments, the probe or primer comprises 5-25 heterologous polynucleotide sequences (e.g. to facilitate cloning). Typically, the probe or primer will hybridize to the DASD mRNA under "stringent conditions" i.e. those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

Specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of DASD. For example, antisense molecules can be RNAs or other molecules, including peptide nucleic acids (PNAs) or non-nucleic acid molecules such as phosphorothioate derivatives, that specifically bind DNA or RNA in a base pair-dependent manner. Compositions of the invention include one or more antibodies that bind DASD and which can be used as a probe to monitor DASD polypeptide expression in a cell. A skilled artisan can readily prepare these polynucleotide and polypeptide compounds using the DASD polynucleotides and polynucleotide sequences and associated information that is disclosed herein.

For use in the methods described above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for DASD protein or DASD gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kits of the invention have a number of embodiments. A typical embodiment is a kit comprising a container, a label on the container, and a composition contained within the container; wherein the composition includes: (1) a polynucleotide that hybridizes to a complement of the DASD polynucleotide and/or (2) an antibody that binds the DASD polypeptide, the label on the container indicates that the composition can be used to evaluate the expression level of the DASD gene product in at least one type of mammalian cell (e.g. a human peripheral blood leukocyte), and instructions for using the DASD polynucleotide or antibody for evaluating the presence of DASD RNA, DNA or protein in at least one type of mammalian cell.

Autism is a heterogeneous condition and is likely to result from the combined effects of multiple, genetic changes including copy number variations and single nucleotide polymorphisms, interacting with environmental factors (see, e.g. Folstein et al., (2001) Nat. Rev. Genet., 2, 943-955; Belmonte et al., (2004) Mol. Psychiatry, 9, 646-663; Veenstra-Vanderweele et al., (2004) Annu Rev Genomics Hum Genet, 5, 379-405; and Muhle et al., (2004) Pediatrics, 113, e472-486). Classifications such as a computer based hierarchy of autistic patients based on genotypic and phenotypic information is one effective way to identify more homogeneous subgroups and hasten the identification of genes underlying autism (see, e.g. Folstein et al., (2001) Nat. Rev. Genet., 2, 943-955; Belmonte et al., (2004) Mol. Psychiatry, 9, 646-663; Veenstra-Vanderweele et al., (2004) Annu Rev Genomics Hum Genet, 5, 379-405; and Muhle et al., (2004) Pediatrics, 113, e472-486). About 3% of autistic children have either FMR1-FM or dup(15q), thus comprising more homogeneous populations with a single major genetic etiology for their autism.

In this context, embodiments of the invention further provides methods of obtaining a gene expression profile associated with autism spectrum disorders and methods of generating a database, or collection, of such profiles. The methods generally involve observing a gene expression profile associated with autism spectrum disorders, storing the data on a computer readable medium (CRM), and linking the data with at least one additional data point such as an individual identifying code and/or familial genetic information and/or the presence or absence of other phenomena (e.g. behavioral phenomena) associated with autism spectrum disorders such as Asperger syndrome, pervasive developmental disorder, mental retardation, speech delay, and other associated psychiatric and neurological phenomena. The profile having this information is then recorded on a CRM.

Figure 11:
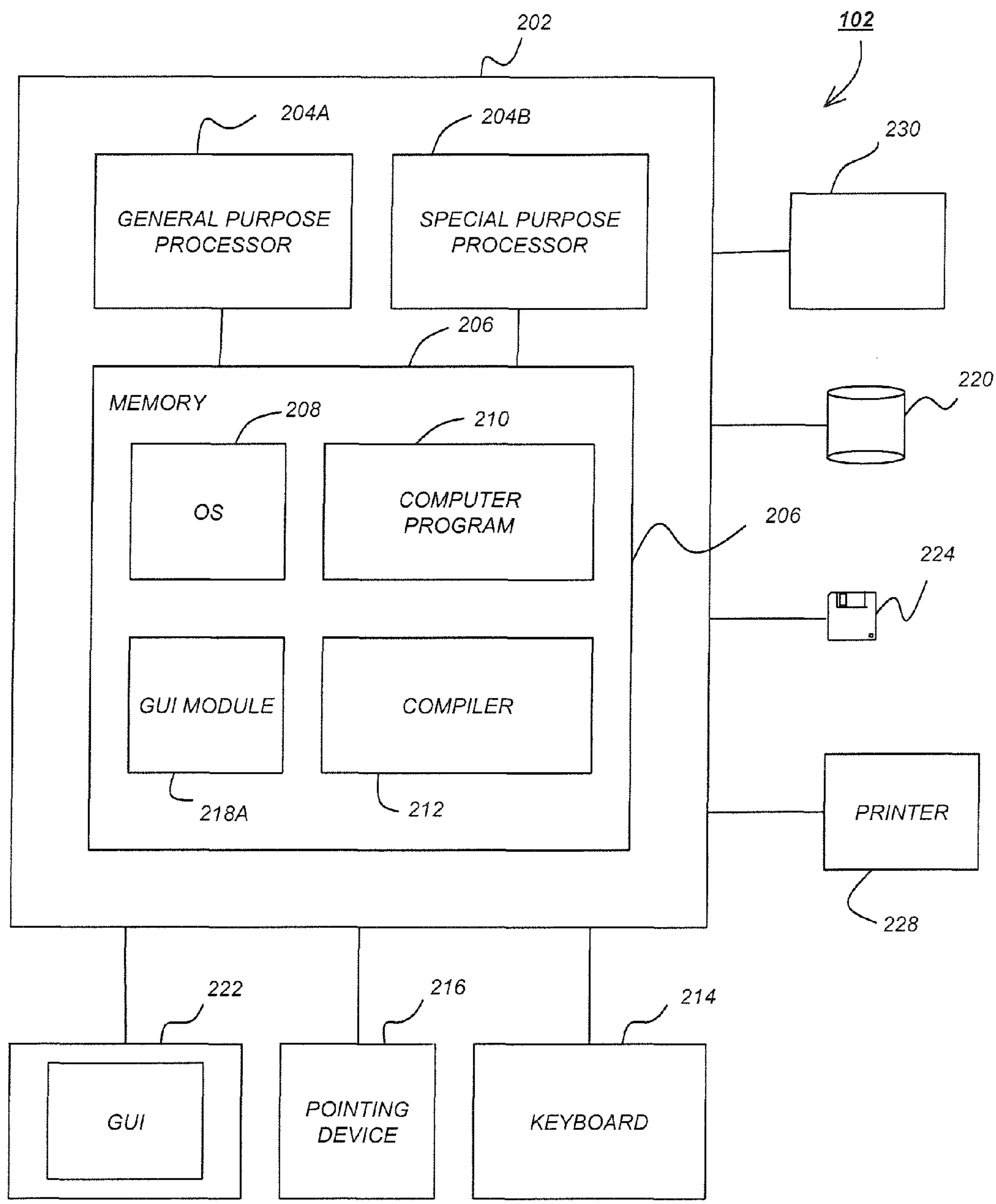
FIG. 11 shows an embodiment of an illustrative computer system that can be used with embodiments of the invention.

Computer related embodiments of the invention disclosed herein can be performed for example, using one of the many computer systems known in the art. For example, embodiments of the invention can include a searchable database library comprising a plurality of cell profiles recorded on a computer readable medium, each of the profiles comprising further information such as identifying codes and/or familial relationships and/or gene expression and/or behavioral phenomena associated with autism spectrum disorders. In this context, one can then use this library of gene expression and behavioral data to, for example, classify and/or examine etiological subsets of autism as well as to explore the pathophysiology of this condition. In one embodiment of the invention, data obtained from a new test sample is compared to data in such a library in order to, for example, find similar comparative profiles in the library from which diagnostic and/or prognostic information can be inferred. FIG. 11 illustrates an exemplary generalized computer system 202 that can be used to implement elements the present invention. The computer 202 typically comprises a general purpose hardware processor 204A and/or a special purpose hardware processor 204B (hereinafter alternatively collectively referred to as processor 204) and a memory 206, such as random access memory (RAM). The computer 202 may be coupled to other devices, including input/output (I/O) devices such as a keyboard 214, a mouse device 216 and a printer 228.

In one embodiment, the computer 202 operates by the general purpose processor 204A performing instructions defined by the computer program 210 under control of an operating system 208. The computer program 210 and/or the operating system 208 may be stored in the memory 206 and may interface with the user and/or other devices to accept input and commands and, based on such input and commands and the instructions defined by the computer program 210 and operating system 208 to provide output and results. Output/results may be presented on the display 222 or provided to another device for presentation or further processing or action. In one embodiment, the display 222 comprises a liquid crystal display (LCD) having a plurality of separately addressable liquid crystals. Each liquid crystal of the display 222 changes to an opaque or translucent state to form a part of the image on the display in response to the data or information generated by the processor 204 from the application of the instructions of the computer program 210 and/or operating system 208 to the input and commands. The image may be provided through a graphical user interface (GUI) module 218A. Although the GUI module 218A is depicted as a separate module, the instructions performing the GUI functions can be resident or distributed in the operating system 208, the computer program 210, or implemented with special purpose memory and processors.

Some or all of the operations performed by the computer 202 according to the computer program 210 instructions may be implemented in a special purpose processor 204B. In this embodiment, some or all of the computer program 210 instructions may be implemented via firmware instructions stored in a read only memory (ROM), a programmable read only memory (PROM) or flash memory in within the special purpose processor 204B or in memory 206. The special purpose processor 204B may also be hardwired through circuit design to perform some or all of the operations to implement the present invention. Further, the special purpose processor 204B may be a hybrid processor, which includes dedicated circuitry for performing a subset of functions, and other circuits for performing more general functions such as responding to computer program instructions. In one embodiment, the special purpose processor is an application specific integrated circuit (ASIC).

The computer 202 may also implement a compiler 212 which allows an application program 210 written in a programming language such as COBOL, C++, FORTRAN, or other language to be translated into processor 204 readable code. After completion, the application or computer program 210 accesses and manipulates data accepted from I/O devices and stored in the memory 206 of the computer 202 using the relationships and logic that was generated using the compiler 212. The computer 202 also optionally comprises an external communication device such as a modem, satellite link, Ethernet card, or other device for accepting input from and providing output to other computers.

In one embodiment, instructions implementing the operating system 208, the computer program 210, and the compiler 212 are tangibly embodied in a computer-readable medium, e.g., data storage device 220, which could include one or more fixed or removable data storage devices, such as a zip drive, floppy disc drive 224, hard drive, CD-ROM drive, tape drive, etc. Further, the operating system 208 and the computer program 210 are comprised of computer program instructions which, when accessed, read and executed by the computer 202, causes the computer 202 to perform the steps necessary to implement and/or use the present invention or to load the program of instructions into a memory, thus creating a special purpose data structure causing the computer to operate as a specially programmed computer executing the method steps described herein. Computer program 210 and/or operating instructions may also be tangibly embodied in memory 206 and/or data communications devices 230, thereby making a computer program product or article of manufacture according to the invention. As such, the terms "article of manufacture," "program storage device" and "computer program product" as used herein are intended to encompass a computer program accessible from any computer readable device or media.

Of course, those skilled in the art will recognize that any combination of the above components, or any number of different components, peripherals, and other devices, may be used with the computer 202. Although the term "user computer" is referred to herein, it is understood that a user computer 102 may include portable devices such as medication infusion pumps, analyte sensing apparatuses, cellphones, notebook computers, pocket computers, or any other device with suitable processing, communication, and input/output capability.

Yet another embodiment of this invention comprises a method of screening for a compound that modulates DASD protein expression comprising the steps of contacting a cell that expresses an endogenous or exogenous DASD protein with one or more compounds and then determining if the one or more compounds modulates DASD protein expression in the cell (e.g. by qPCR techniques practiced on the cell in the presence and absence of the one or more compounds). Another embodiment of this invention comprises a method of screening for a compound that interacts with an DASD protein comprising the steps of contacting one or more compounds with the DASD protein, and then determining if a compound interacts with the DASD protein (e.g. by binding techniques that separating compounds that interact with the DASD protein from compounds that do not). This embodiment of the invention can be used for example to screen chemical libraries for compounds which modulate, e.g., inhibit, antagonize, or agonize or mimic, the expression of a DASD as measured by one of the assays disclosed herein. The chemical libraries can be peptide libraries, peptidomimetic libraries, chemically synthesized libraries, recombinant, e.g., phage display libraries, and in vitro translation-based libraries, other non-peptide synthetic organic libraries. Exemplary libraries are commercially available from several sources (e.g. e, Tripos/PanLabs, ChemDesign, Pharmacopoeia). Typical peptide libraries and screening methods that can be used to identify compounds that modulate the expression of and/or interact with DASD protein sequences are disclosed for example in U.S. Pat. Nos. 5,723,286 and 5,733,731, the contents of which are incorporated by reference.

Various aspects of the invention are further described and illustrated by way of the examples that follow, none of which are intended to limit the scope of the invention. Certain disclosure in the examples below can be found in Nishimura et al., Human Molecular Genetics 2007 16(14): 1682-1698, the contents of which are incorporated by reference. In addition, certain methods and materials used in embodiments of the invention can be those found for example n U.S. Patent Application Nos.: 2002/0155450; 2006/0141519; 2007/0134664; and 2009/0011414, the contents of which are incorporated by reference.

EXAMPLES

Example 1

Genome-Wide Expression Profiling of Lymphoblastoid Cell Lines Distinguishes Different Forms of Autism and Reveals Shared Pathways Autism is a heterogeneous condition that is likely to result from the combined effects of multiple genetic factors interacting with environmental factors. Given its complexity, the study of autism associated with Mendelian single gene disorders or known chromosomal etiologies provides an important perspective. We used microarray analysis to compare the mRNA expression profile in lymphoblastoid cells from males with autism due to a Fragile X mutation (FMR1-FM), or a 15q11-q13 duplication (dup(15q)), and non-autistic controls. We were able to clearly distinguish autism from controls and separate individuals with autism based on their genetic etiology. Sixty-eight genes were dysregulated in common between autism with FMR1-FM and dup(15q). We identified a potential molecular link between FMR1-FM and dup(15q), the cytoplasmic FMR1 interacting protein 1 (CYFIP1), which was up-regulated in dup(15q) patients. We were able to confirm this link in vitro by showing common regulation of two other dysregulated genes, JAKMIP1 and GPR155, downstream of FMR1 and CYFIP1. We also confirmed the reduction of the JAKMIP1 protein in FMR1 knock out mice, demonstrating in vivo relevance. Finally, we showed independent confirmation of roles for JAKMIP1 and GPR155 in autism spectrum disorders (ASD) by showing their differential expression in male sib pairs discordant for idiopathic ASD. These results provide evidence that blood-derived lymphoblastoid cells gene expression is likely to be useful for identifying etiological subsets of autism and to explore its pathophysiology.

It has become increasingly clear that genetic factors are significant determinants of autism pathophysiology (see, e.g. Folstein et al., (2001) Nat. Rev. Genet., 2, 943-955; Belmonte et al., (2004) Mol. Psychiatry, 9, 646-663; Veenstra-Vanderweele et al., (2004) Annu Rev Genomics Hum Genet, 5, 379-405; Muhle et al., (2004) Pediatrics, 113, e472-486). Although, multiple genetic approaches have been undertaken to identify loci or genes for autism spectrum disorders (ASD) (1-18), identification of causal genes has been hampered by genetic and phenotypic heterogeneity. Thus, it seems reasonable to accelerate the gene discovery process by using combinations of experimental approaches, such as the study of "single gene" or more simple causes, such as chromosomal copy number imbalances, whose phenotypes include ASD (see, e.g. Folstein et al., (2001) Nat. Rev. Genet., 2, 943-955; Belmonte et al., (2004) Mol. Psychiatry, 9, 646-663; Veenstra-Vanderweele et al., (2004) Annu Rev Genomics Hum Genet, 5, 379-405; Muhle et al., (2004) Pediatrics, 113, e472-486). One such disorder is fragile X syndrome (FXS) (see, e.g. Folstein et al., (2001) Nat. Rev. Genet., 2, 943-955; Belmonte et al., (2004) Mol. Psychiatry, 9, 646-663; Veenstra-Vanderweele et al., (2004) Annu Rev Genomics Hum Genet, 5, 379-405; Muhle et al., (2004) Pediatrics, 113, e472-486; and Brown et al. (1986) Am. J. Med. Genet., 23, 341-352), which is caused by an expansion of the trinucleotide repetitive sequence (CGG)n in the promoter region of the fragile X mental retardation 1 (FMR1) gene located at Xq27.3 (see. e.g. Verkerk et al. (1991) Cell, 65, 905-914). This mutation causes a significant deficit of the FMR1 protein (FMRP) and a phenotype including cognitive impairment and other behavioral abnormalities that overlap with ASD. The prevalence of ASD among FXS cases has been estimated at 15-33% (see, e.g. Rogers et al. (2001) J. Dev. Behav. Pediatr., 22, 409-417; and Goodlin-Jones et al. (2004) J. Dev. Behav. Pediatr., 25, 392-398) and approximately 1% to 2% of those with autism and no obvious physical features of FXS are found to have FMR1-FM (see, e.g. Brown et al. (1986) Am. J. Med. Genet., 23, 341-352; and Bailey et al. (1996) J. Child. Psychol. Psychiatry, 37, 89-126).

Another disorder that causes ASD is a maternally inherited duplication of 15q11-q13 (dup(15q)) (see, e.g. Folstein et al., (2001) Nat. Rev. Genet., 2, 943-955; Belmonte et al., (2004) Mol. Psychiatry, 9, 646-663; Veenstra-Vanderweele et al., (2004) Annu Rev Genomics Hum Genet, 5, 379-405; Muhle et al., (2004) Pediatrics, 113, e472-486; and Sutcliffe et al. (2003) J. Am. Acad. Child. Adolesc. Psychiatry, 42, 253-256). Multiple repeat elements within the region mediate a variety of rearrangements, including interstitial duplications, interstitial triplications, and supernumerary isodicentric marker chromosomes (see, e.g. Wang et al. (2004) Am. J.

Hum. Genet., 75, 267-281). Dup(15q) occurs with an estimated frequency of 1:600 in children with developmental delay (see, e.g. Thomas et al. (2003) Am. J. Med. Genet. A, 120, 596-598) and is the most common copy number variation causing ASD (see, e.g. Veenstra-Vanderweele et al., (2004) Annu Rev Genomics Hum Genet, 5, 379-405; and Sutcliffe et al. (2003) J. Am. Acad. Child. Adolesc. Psychiatry, 42, 253-256). Over-expression of ubiquitin protein ligase E3A (UBE3A) and/or ATPase Class V type 10A (ATP10A) could represent a major underlying molecular factor for autism (see, e.g. Herzing et al. (2002) Hum. Mol. Genet., 11, 1707-1718; and Herzing et al. (2001) Am. J. Hum. Genet., 68, 1501-1505). However, autism is not a universal finding in maternal uniparental disomy of the 15q11-q13 region, a condition in which UBE3A and ATP10A are over-expressed (see, e.g. Sutcliffe et al. (2003) J. Am. Acad. Child. Adolesc. Psychiatry, 42, 253-256). These results suggest that dysregulation of non-imprinted genes in the duplicated region and/or throughout the whole genome may contribute to the autistic phenotype observed in dup(15q). Therefore, we reasoned that the identification of genes whose expression is dysregulated by both FMR1-FM and dup(15q) may provide genes relevant to ASD, since the two genetic abnormalities represent cases where single mutations, either a trinucleotide repeat or copy number variation (see, e.g. Sebat et al. (2004) Science, 305, 525-528), cause ASD. We also wanted to examine, as a proof of principle, whether lymphoblast gene expression profiles identified by microarrays can differentiate between these single mutation "simple" causes of autism and controls. If this were the case, this would provide a basis for further study using this technique in idiopathic autism, where more multigenic inheritance and environmental influences may be at play (see, e.g. Folstein et al., (2001) Nat. Rev. Genet., 2, 943-955; Belmonte et al., (2004) Mol. Psychiatry, 9, 646-663; Veenstra-Vanderweele et al., (2004) Annu Rev Genomics Hum Genet, 5, 379-405; Muhle et al., (2004) Pediatrics, 113, e472-486).

Recently, several studies have suggested that lymphoblastoid cells can be used to detect biologically plausible correlations between candidate genes and neuropsychiatric diseases, including Rett syndrome (see e.g. Horike et al. (2005) Nat. Genet., 37, 31-40), nonspecific X-linked mental retardation (see, e.g. Meloni et al. (2002) Nat. Genet., 30, 436-44), bipolar disorder (see, e.g. Iwamoto et al. (2004) Mol. Psychiatry, 9, 406-416), FXS (see e.g. Brown et al. (2001) Cell, 107, 477-87) and dup(15q) (see, e.g. Baron et al. (2006) Hum. Mol. Genet, 15, 853-869). In the present study, we investigated whether gene expression profiles of lymphoblastoid cells could be used (i) to differentiate autistic subjects who were ascertained and diagnosed as having ASD in the Autism Genetic Resource Exchange (AGRE) (see, e.g. Geschwind et al. (2001) Am. J. Hum. Genet., 69, 463-466) repository into etiological categories (FMR1-FM and dup(15q)) and (ii) to identify common genes and pathways that might be relevant to autism across these two distinct forms. Here, we demonstrate that the gene expression profile was able to clearly distinguish individuals based on their etiology. We also identified 68 genes commonly dysregulated in autism with FMR1-FM and dup(15q). Interestingly, we identified a molecular connection between FMR1-FM and dup(15q), CYFIP1, which was significantly induced in dup(15q) and is known to antagonize certain aspects of FMRP function (see, e.g. Schenck et al. (2003) Neuron, 38, 887-98). We further demonstrated that the expression of janus kinase and microtuble interacting protein 1 (JAKMIP1) and G protein-coupled receptor 155 (GPR155) were commonly dysregulated by either reduction of FMR1 or induction of CYFIP1 in vitro. The expression of JAKMIP1 was also dysregulated in the brain of the FMR1 knock-out mouse. Finally, we were able to show that JAKMIP1 and GPR155 were dysregulated in males with autism spectrum disorders (ASD), relative to their non-affected siblings, providing independent confirmation suggesting that these genes are associated with ASD.

Results

Hierarchical Clustering and Principal Component Analysis Distinguish Individuals Based on Genetic Etiology We analyzed the whole-genome mRNA expression profile in lymphoblastoid cells from 15 autistic males (8 autistic males with FMR1-FM and 7 autistic males with dup(15q)) and 15 non-autistic control males from AGRE (see supplemental table S1 in Nishimura et al., Human Molecular Genetics 2007 16(14): 1682-1698, the contents of which are incorporated herein by reference) using Agilent Whole Genome Human Microarrays. Overall, out of 41,000 probes analyzed, 31,044 probes, representing 23,822 genes, were expressed in the lymphoblastoid cells. To find genes that were differentially expressed across the three subject groups, the expression profile of the lymphoblastoid cells was subjected to Analysis of Variance (ANOVA) (see, e.g. Cui et al. (2003) Genome Biol., 4, 210). ANOVA identified 293 probes (277 genes) below a defined false discovery rate (FDR) threshold of 5% (see supplemental table S2 in Nishimura et al., Human Molecular Genetics 2007 16(14): 1682-1698, the contents of which are incorporated herein by reference). It has been shown that the expression of FMR1 is decreased in lymphoblastoid cells with FMR1-FM (see, e.g. Sutcliffe et al. (1992) Hum. Mol. Genet., 1, 397-400) and that the expression of UBE3A is increased in lymphoblastoid cells with dup(15q) (see, e.g. Herzing et al. (2002) Hum. Mol. Genet., 11, 1707-1718). Concordant with these reports, FMR1 and UBE3A were among the 293 differentially expressed probes, providing independent controls for the microarray analysis.

Figure 1A:
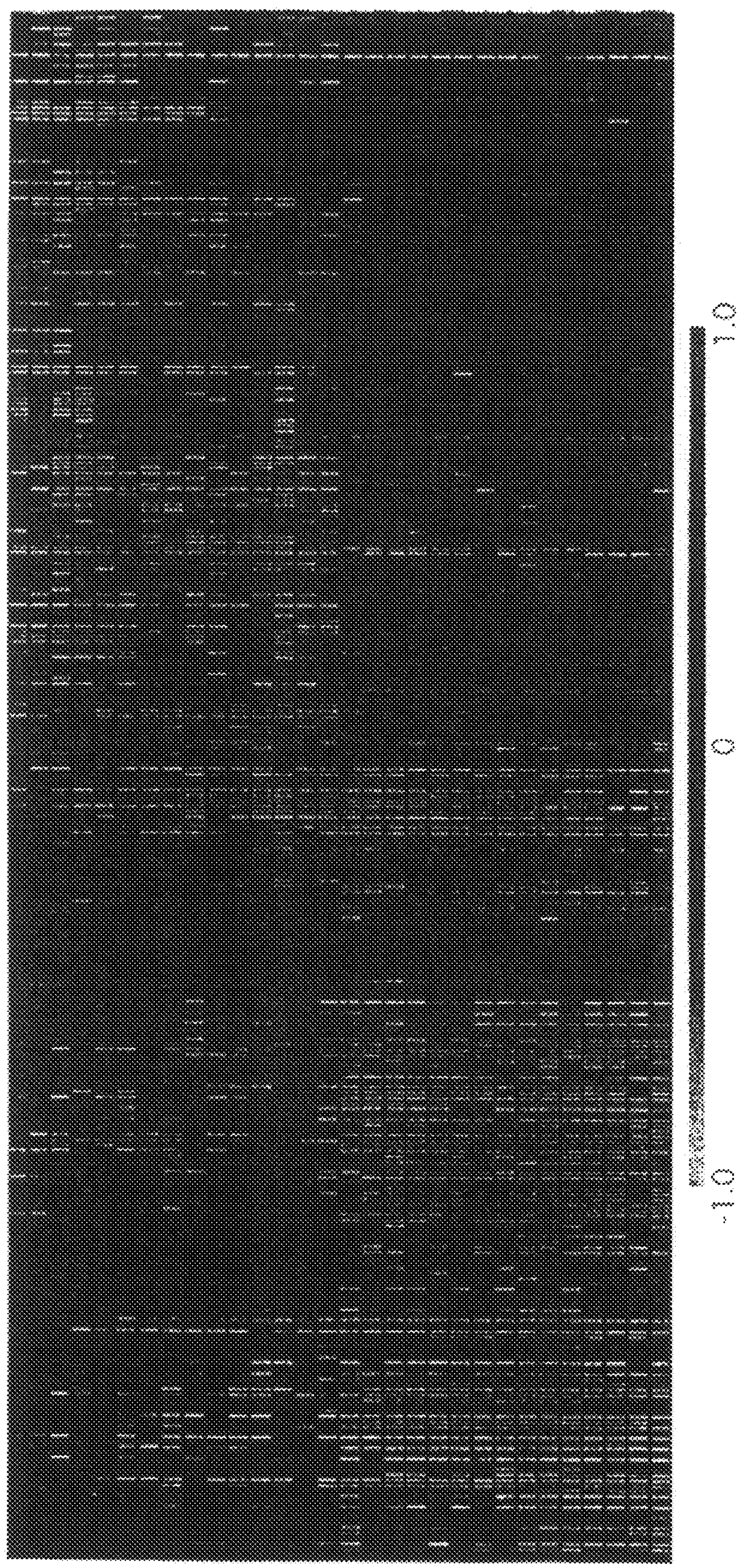
Figure 3:
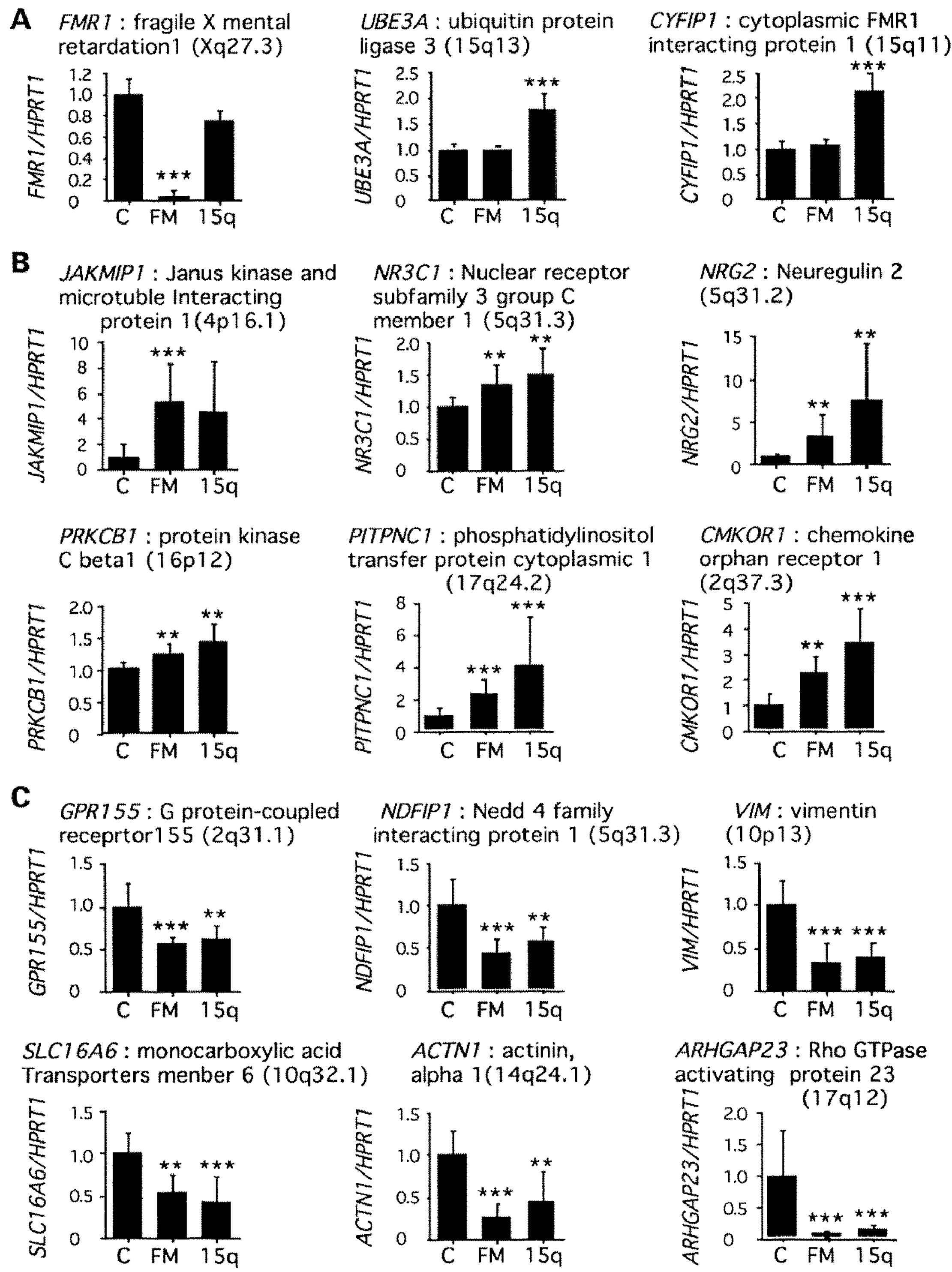
FIG. 3 shows a confirmation of the differential gene expression by qRTPCR. Total RNA was extracted from lymphoblastoid cells with FMR1-FM, dup(15q) or control and qRTPCR were performed to confirm the differential expression identified by microarray analysis. A) Genes specifically dysregulated in autism with FMR1-FM or dup(15q). B) Genes commonly up-regulated in autism with FMR1-FM and dup(15q). C) Genes commonly down-regulated in autism with FMR1-FM and dup(15q). Results represent means±S.D. of each group. The mean of the value of control subjects was set as 1. P-value was calculated by Mann-Whitney U test using control (N=15) vs. autism with FMR1-FM (N=8) or autism with dup(15q) (N=7). $*p<0.05$, $p<0.01$, $*p<0.001$.

As shown in FIGS. 1A and B, hierarchical clustering using the 293 probes clearly classified individuals based on their genotype. The 293 probes were also subjected to principal component analysis (PCA). As shown in FIG. 1C, 3 dominant PCA components that contained 70% of the variance in the data matrix clearly separated individuals based on genetic etiology. In this plot, the first principal component axis accounted for 56% of the variance in the data set and clearly separated autism with FMR1-FM and dup(15q) from controls, whereas the second principal component (PC2) accounted for 10% of the variance and segregated autism with FMR1-FM from autism with dup(15q). The top 10 genes contributing to PC2 include FMR1, UBE3A, CYFIP1, non-imprinted in Prader-Willi/Angelman syndrome 2 (NIPA2), and hect domain and RLD 2 (HERC2). The latter four genes are all located within the 15q11-q13 region. These results suggest that the selective reduction of FMR1 and the selective induction of the four genes located in 15q11-q13 differentiated autism with FMR1-FM from autism with dup(15q). These data provide a critical proof of principle that the gene expression profile of lymphoblastoid cells could be used to subgroup subjects with autism based on their genetic etiologies when the etiologies are due to a single mutation or copy number variation.

Microarray Analyses Revealed the Significant Overlap of FMR1-FM and dup(15q)

To identify the set of the most robustly differentially expressed genes in each group, we identified genes found using three different statistical methods, ANOVA, Significant Analysis of Microarray (SAM) (see, e.g. Tusher et al. (2001) Proc. Natl. Acad. Sci. USA, 98, 5116-5121) and Rank Product Analysis (RankProd) (see, e.g. Breitling et al. (2004)

Figure 2:
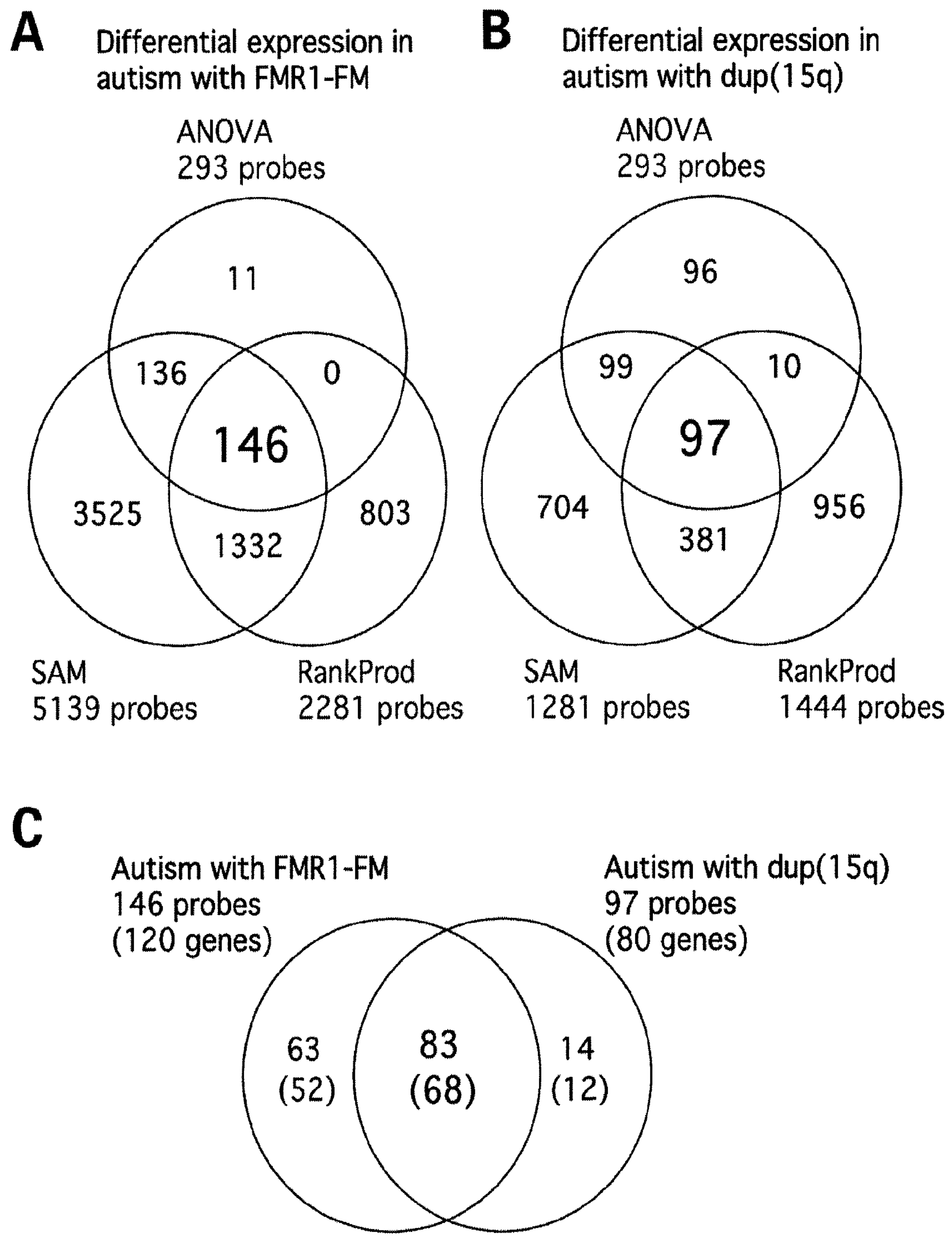
FIG. 2 shows differentially expressed probes identified by three different statistical methods, ANOVA, SAM and RankProd. Venn diagram showing the number of probes identified as differentially expressed between A) autism with FMR1-FM (n=8) and control (n=15) and B) autism with dup(15q) (n=7) and control (n=15). C) Overlap of the differentially expressed probes (genes) in autism with FMR1-FM and dup (15q).

FEBS Lett., 573, 83-92). SAM is a modified t-test statistic, whereas RankProd is a non-parametric statistic that detects items that are consistently highly ranked in a number of lists. SAM identified 5139 probes and 1281 probes as significant (FDR<5%) in autism with FMR1-FM and dup(15q), respectively (FIGS. 2A and B). RankProd identified 2281 probes and 1444 probes as significant (FDR<5%) in autism with FMR1-FM and dup(15q), respectively (FIGS. 2A and B). The combination of ANOVA, SAM and RankProd identified 146 probes (120 genes) in autism with FMR1-FM and 97 probes (80 genes) in autism with dup(15q) (FIG. 2C). Eighty-three probes representing 68 genes were dysregulated in both autism with FMR1-FM and dup(15q) (see Table 1 in Nishimura et al., Human Molecular Genetics 2007 16(14): 1682-1698, the contents of which are incorporated herein by reference). This degree of overlap was highly significant (hypergeometric probability, $P=1.2\times10^{-153}$). Fifty-two genes and 12 genes were selectively dysregulated in either autism with FMR1-FM and autism with dup(15q), respectively (see Table 2 in Nishimura et al., Human Molecular Genetics 2007 16(14): 1682-1698, the contents of which are incorporated herein by reference).

qRTPCR Confirmed the Differential Expression Identified by the Microarray Analysis To validate the differential expression identified by microarray analysis using independent methods, we performed quantitative real-time PCR analysis (qRTPCR) of 19 genes chosen as a cross section using the same samples used in the microarray analysis. qRTPCR confirmed that 17 of the 19 genes were differentially expressed as expected by the microarray analysis (FIG. 3, A-C). There was an overall highly significant correlation between microarray and qRT-PCR results (Pearson correlation, r=0.57, P<0.0001).

CYFIP1 was one of the genes selectively induced in autism with dup(15q). Because CYFIP1 is known to antagonize FMRP (see, e.g. Schenck et al. (2003) Neuron, 38, 887-98), we reasoned that the induction of CYFIP1 in dup(15q) might explain some of the significant overlap between autism with FMR1-FM and dup(15q). JAKMIP1, also known as Marlin-1, was significantly induced in autism with FMR1-FM and had a positive trend in autism with dup(15q) (P=0.062), suggesting that JAKMIP1 could represent a commonly dysregulated pathway. In fact, RankProd identified JAKMIP1 as a significantly up-regulated gene in dup(15q) by microarray analysis. This gene is a particularly biologically important candidate, given its putative role in GABAB receptor expression (see, e.g. Couve et al. (2004) J. Biol. Chem., 279, 13934-13943) and the microtubule network (see, e.g. Steindler et al. (2004) J. Biol. Chem., 279, 43168-43177).

Functional Annotation Revealed Pathway Dysregulation

In an attempt to uncover the common functional meanings among the differentially expressed genes, we classified genes into gene ontology groups using DAVID (see, e.g. Dennis et al. (2003) Genome Biol., 4, P3). Table 3 in Nishimura et al., Human Molecular Genetics 2007 16(14): 1682-1698, the contents of which are incorporated herein by reference, shows the top 3 clusters identified by DAVID using the 68 genes dysregulated in autism with FMR1-FM and dup(15q), or the 52 genes selectively dysregulated in autism with FMR1-FM. The number of genes selectively dysregulated in autism with dup(15q) was too small to analyze using the functional annotation clustering.

Genes related to cell communication ($P=7.6\times10^{-6}$) and signal transduction ($P=2.2\times10^{-5}$) were most significantly enriched in the 68 genes commonly dysregulated in autism with FMR1-FM and dup(15q). Genes related to immune response ($P=3.7\times10^{-3}$) and defense response ($P=7.3\times10^{-3}$) were also enriched in this gene set. Genes related to chaperone ($P=2.6\times10^{-2}$) and protein folding ($P=3.2\times10^{-2}$) were enriched in the 52 genes selectively dysregulated in autism with FMR1-FM. Genes related to RNA binding ($P=1.2\times10^{-2}$) and mRNA metabolism ($P=2.1\times10^{-2}$) were also enriched in this gene set, consistent with the FMRP protein's function as RNA binding protein important in regulatory translation (see, e.g. Bagni et al. (2005) Nat. Rev. Neurosci., 6, 376-387). Chaperones and folding proteins are commonly found to operate co-translationally, providing a potential link with FMRP function.

To provide a more refined functional classification of genes, we used Ingenuity Pathway Analysis (IPA) (see, e.g. Ingenuity Pathway Analysis. (http://www.ingenuity.com/)), a powerful tool for investigating the biological pathways represented by the genes commonly dysregulated in autism with FMR1-FM and dup(15q). IPA uses known protein-protein and gene-gene interactions that have been culled into a curated database and associates the list of differentially expressed genes with biological networks. IPA identified three statistically significant networks, each containing at least ten genes (see Table 4 and supplemental FIG. 1) in Nishimura et al., Human Molecular Genetics 2007 16(14): 1682-1698, the contents of which are incorporated herein by reference). Principal functions associated with these networks were cell cycle ($P=5.2\times10^{-8}$), cellular movement ($P=1.3\times10^{-8}$) and cell-to-cell signaling and interaction ($P=4.3\times10^{-8}$). The "cell-to-cell signaling and interaction" was consistent with "cell communication" and "signal transduction" categories identified by the DAVID. The identification of the "molecular transport" pathway containing JAKMIP1 was particularly salient, given this gene's known role in GABAR trafficking within neurons. There were also other important genes in this pathway, including PSCD3, an ADP-ribosylation factor of unknown CNS function and ACTN1, a cytoskeletal anchoring protein. Based on this analysis, it is plausible that JAKMIP1 may act along with these genes in the segregation of signaling complexes involved in neural transmission.

Figure 4:
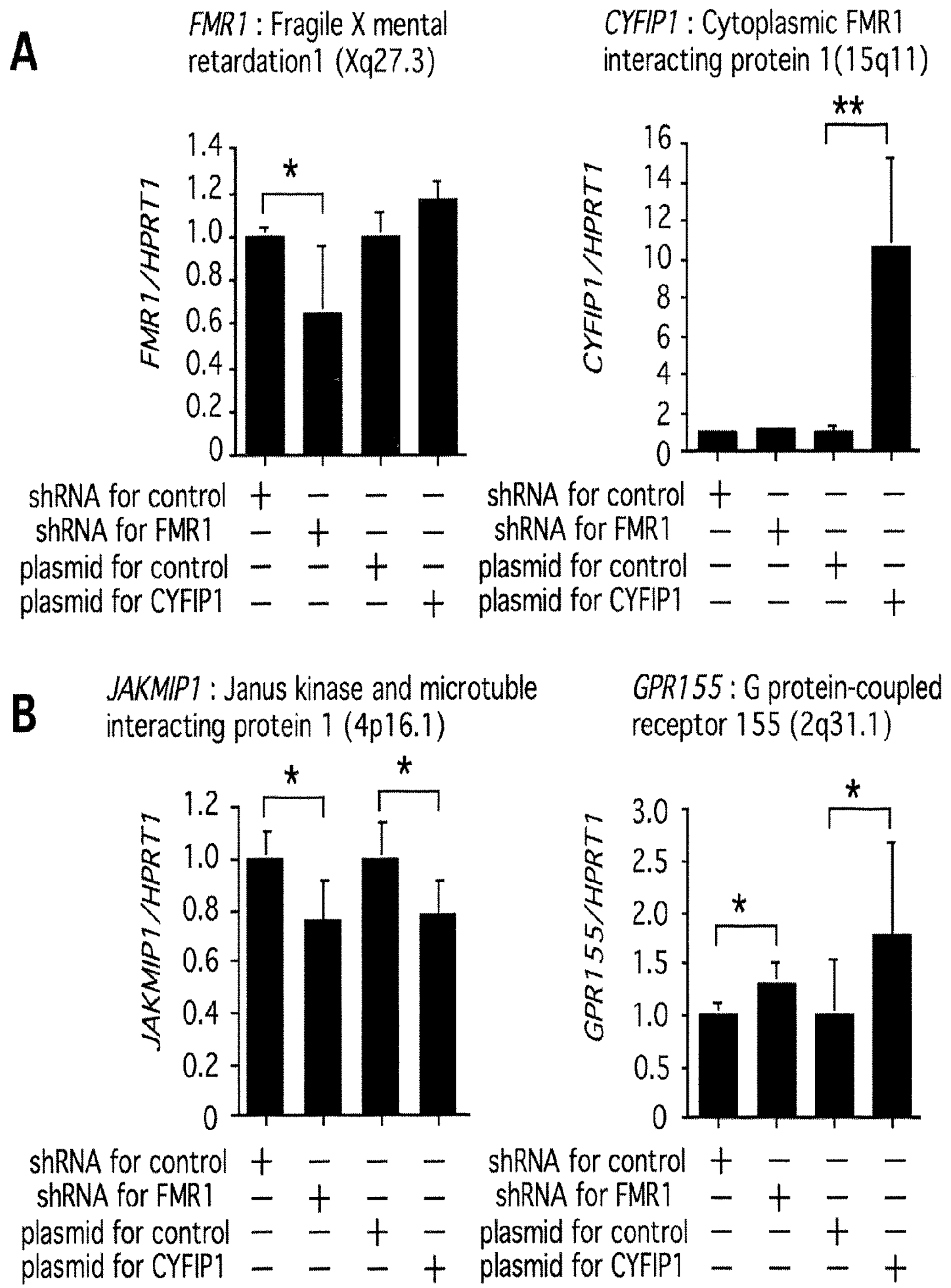
FIG. 4 shows that JAKMIP1 and GPR155 were commonly dysregulated by reduction of FMR1 and induction of CYFIP1. SH-SY5Y cells were stably transfected with i) vector expressing shRNA for control, ii) vector expressing shRNA for FMR1, iii) empty expression vector or iv) expression vector for CYFIP1. Total RNA was extracted from each and qRTPCR was performed to validate the effect of FMR1 and CYFIP1 on the expression of JAKMIP1 and GPR155. A) The expression of FMR1 was significantly reduced in SY5Y cells expressing shRNA for FMR1, whereas the expression of CYFIP1 was significantly induced in SY5Y cells over-expressing CYFIP1. B) The expression of JAKMIP1 was significantly reduced in SH-SY5Y cells expressing shRNA for FMR1 and over-expressing CYFIP1. The expression of GPR155 was significantly induced in SH-SY5Y cells expressing shRNA for FMR1 and over-expressing CYFIP1. Results represent means±S.D. of each group. The mean of the value of each control was set as 1. Significance was calculated by the Mann-Whitney U test using SH-SY5Y cells expressing shRNA for control (N=4) vs. shRNA for FMR1 (N=4) or empty expression vector (N=8) vs. expression vector for CYFIP1 (N=7). *P<0.05, **P<0.01.

Effect of Down-Regulation of FMR1 and Up-Regulation of CYFIP1 in a Neuronal Cell on the Expression of the Dysregulated Genes Identified in Lymphoblastoid Cells Although we identified dysregulated genes in autism with FMR1-FM and dup(15q) using lymphoblastoid cells, we were interested in whether the expression of these genes would also be dependent on FMR1 and CYFIP1 in neuronal cells. To examine the effect of FMR1 and CYFIP1 in neuronal cells, we used the well characterized human neuronal cell line SH-SY5Y (see, e.g. Millar et al. (2005) Science, 310, 1187-1191). FMR1 and CYFIP1 dependence in SH-SY5Y cells were assessed using short hairpin RNA (shRNA) to reduce the expression of FMR1 and a plasmid expression vector to induce the expression of CYFIP1, respectively. As shown in FIG. 4A, the expression of FMR1 was reduced to about 60% of its normal level in SH-SY5Y cells stably expressing FMR1 shRNAs, whereas the expression of CYFIP1 was significantly induced (11-fold) in SH-SY5Y cells stably transfected with the CYFIP1 plasmid.

We were able to further demonstrate the effect of down-regulation of FMR1 and up-regulation of CYFIP1 on the expression of two key downstream genes (FIG. 4B). In SH-SY5Y cells transfected with FMR1 shRNA, the expression of JAKMIP1 and GPR155 were significantly reduced and induced, respectively. In SH-SY5Y cells over-expressing CYFIP1, the expression of JAKMIP1 and GPR155 were also reduced and induced, respectively. These findings demonstrated that the expression of JAKMIP1 and GPR155 were also dependent on FMR1 and CYFIP1 in SH-SY5Y cells and that reduction of FMR1 and induction of CYFIP1 can share common downstream effects on the expression of JAKMIP1 and GPR155.

The Expression of JAKMIP1 Protein was Dependent on FMR1 and CYFIP1

Figure 5:
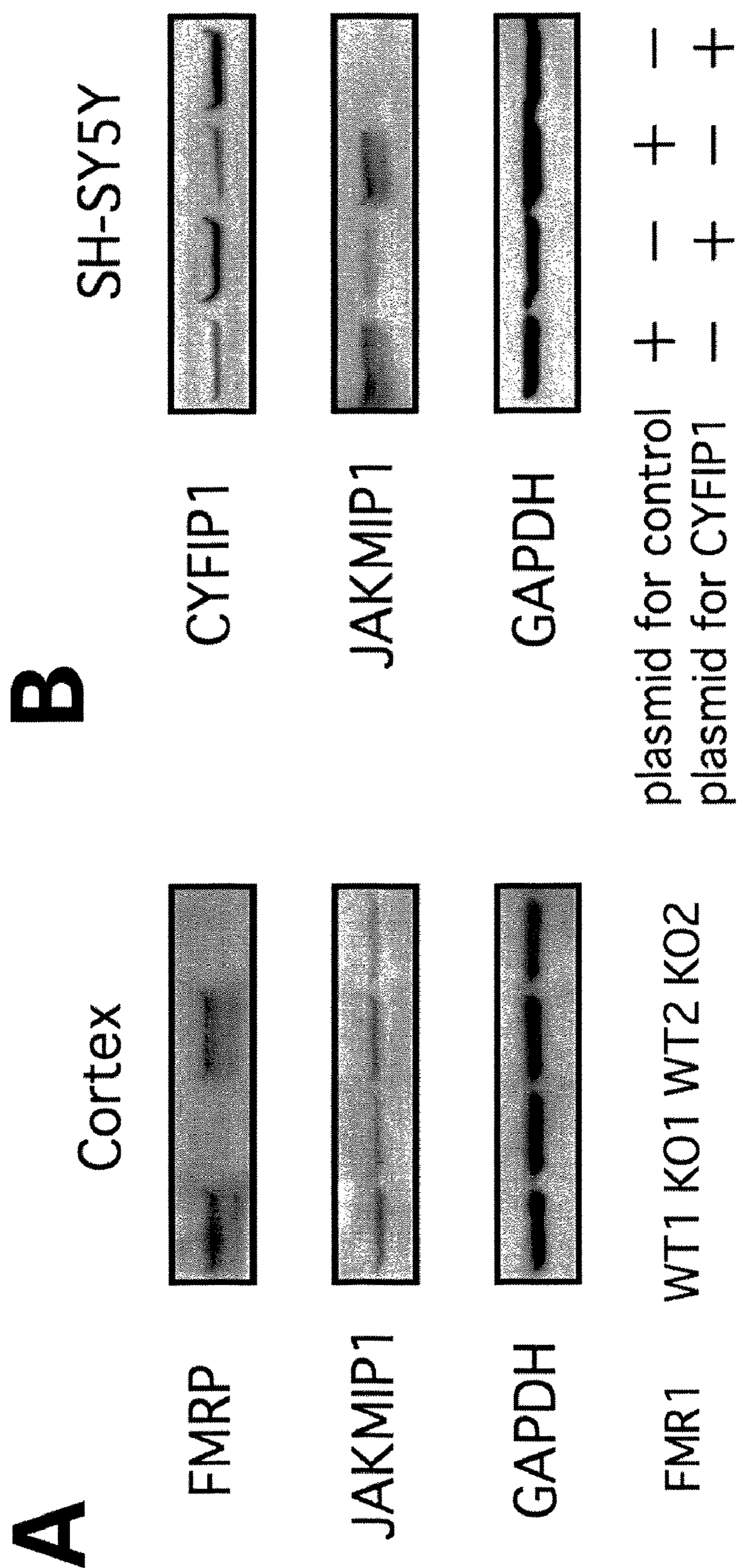
FIG. 5 shows that the expression of JAKMIP1 protein was dependent on FMR1 and CYFIP1 in mouse cortex and SH-SY5Y cells. Proteins were extracted from the cortex of FMR1 WT or KO mice (A), or SH-SY5Y cells transfected with empty vector or CYFIP1 cDNA (B). Western blotting was performed to validate the effect of the reduction of FMR1 or induction of CYFIP1 on the expression of JAKMIP1 protein. The protein expression of JAKMIP1 was reduced in cortex of FMR1-KO mice (A) as well as SH-SY5Y cells transfected with shRNA for FMR1 and SH-SY5Y over-expressing CYFIP1 (B). Data shown in (A) and (B) were the representative of two independent experiments.

Then, we validated the effect of FMR1 or CYFIP1 on the protein expression of JAKMIP1 in the central nervous system (CNS). We examined the expression of the JAKMIP1 protein in the cortex of FMR1 knock-out (KO) and wild-type (WT) mice and SH-SY5Y cells transfected with the CYFIP1 over-expression plasmid. The expression of JAKMIP1 protein was reduced in cortex of FMR1 KO mice (FIG. 5A) and SH-SY5Y cells over-expressing CYFIP1 (FIG. 5B). These findings confirmed the in vitro findings that the expression of JAKMIP1 was dependent on FMR1 in mouse brain, suggesting that at least some of the changes observed in lymphoblastoid cells reflect similar changes in the CNS.

Figure 6:
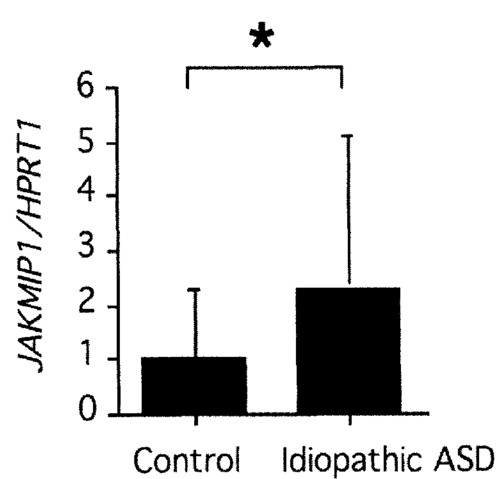
FIG. 6 shows that JAKMIP1 and GPR155 were dysregulated in the ASD proband in discordant male sib pairs. Total RNA was extracted from lymphoblastoid cells of 27 male sib pairs discordant for ASD and qRTPCR were performed to confirm the differential expression of JAKMIP1 and GPR155. Results represent means±S.D. of each group. The mean of the value of control subjects was set as 1. P-value was calculated by Wilcoxon rank-sum test using control (N=27) vs. ASD (N=27). *p<0.05]
Figure 6:
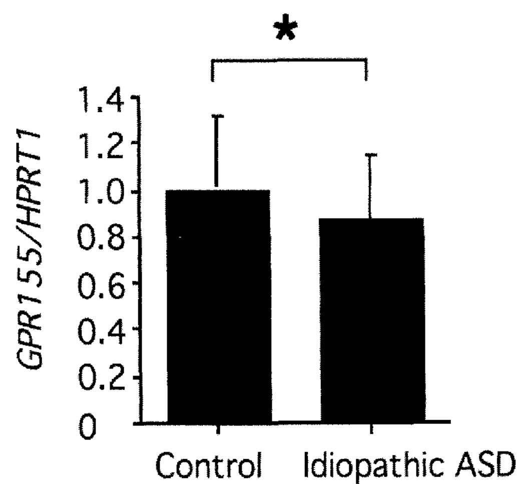
Figure 7:
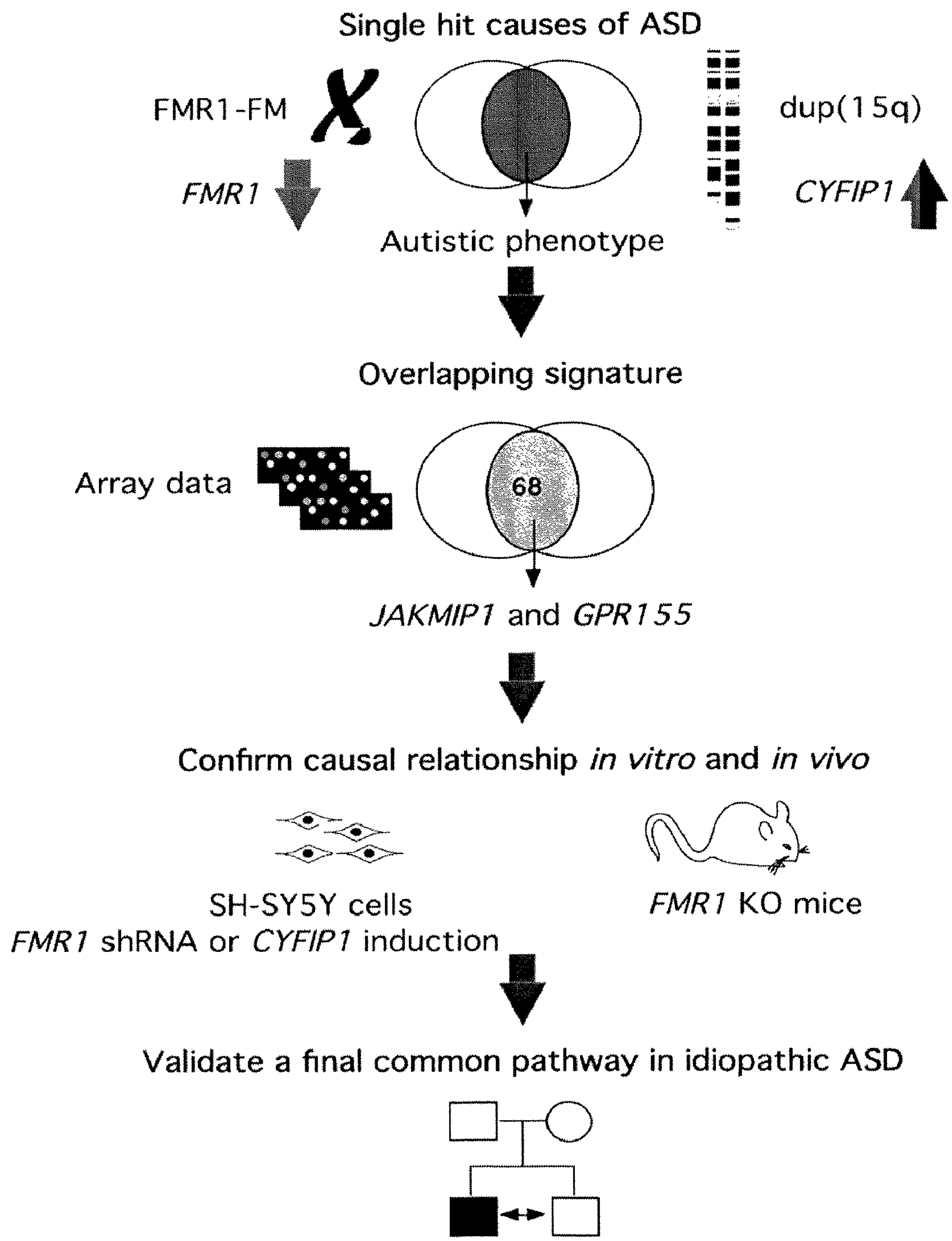
FIG. 7 shows the molecular convergence of FMR1-FM, dup(15q) and idiopathic ASD. The mRNA expression profile in lymphoblastoid cells from autism with FMR1-FM or dup (15q) and control were compared using microarray analysis. 68 genes were dysregulated in both autism with FMR1-FM and dup(15q). Induction of CYFIP1 in dup(15q) is a potential molecular link between FMR1-FM and dup(15q). Among the dysregulated genes, JAKMIP1 and GPR155 were further analyzed to confirm the causal relationship between CYFIP1 and FMR1 expression and their expression in neural cells or tissue and to validate the dysregulation of these genes in lymphoblastoid cells from subjects with idiopathic ASD.

The Expression of JAKMIP1 and GPR155 were Significantly Different Between 27 Male Sib Pairs Discordant for Idiopathic ASD To determine the potential generalizability of these findings to idiopathic autism, we examined whether the expression of JAKMIP1 and GPR155 were also dysregulated in lymphoblastoid cells from idiopathic ASD cases. We selected 27 male sib pairs discordant for ASD from AGRE (see supplemental table S1 in Nishimura et al., Human Molecular Genetics 2007 16(14): 1682-1698, the contents of which are incorporated herein by reference). The 27 males with ASD did not have FMR1-FM or dup(15q) and had surrogate IQ markers (Raven's progressive matrices) >70. As shown in FIG. 6, the expression of JAKMIP1 and GPR155 were significantly dysregulated in the 27 males with ASD compared to their sibs without ASD. These results show that the dysregulation of JAKMIP1 and GPR155 are associated with ASD. The lack of general intellectual disability in this ASD group also shows that these dysregulation are not simply due to a non-specific cognitive impairment or intellectual disability observed in FXS and dup(15q). However, both in vitro (SH-SY5Y cells) and in vivo (brain) CNS tissues, the direction of JAKMIP1 and GPR155 regulation were opposite to that observed in lymphoblastoid cells. The differences may reflect many facts, including immortalization or alternative regulatory signaling pathways in different tissues. However, these data are consistent between FMR1-FM and dup(15q) and indicate that expression of JAKMIP1 and GPR155 are regulated by both FMR1 and CYFIP1 levels, albeit differently between neural tissues and lymphoblastoid cells, providing potential common signaling pathways dysregulated in ASD.

In this study, we performed global mRNA expression profiling from males with autism carrying either FMR1-FM or dup(15q) and control males. We found that these autistic individuals can be differentiated based on their genetic etiologies by lymphoblast gene expression profiles. Interestingly, this analysis also revealed a common gene expression signature across these two distinct genetic conditions leading to ASD that was significantly different from control profiles. We used the intersection of three different statistical tests to identify the most robustly differentially expressed genes (see, e.g. Cui et al. (2003) Genome Biol., 4, 210; Tusher et al. (2001) Proc. Natl. Acad. Sci. USA, 98, 5116-5121; and Breitling et al. (2004) FEBS Lett., 573, 83-92). The qRTPCR data confirmed this gene selection strategy.

Gene Expression Profiles of Lymphoblastoid Cells Carrying the FMR1-FM

We identified 120 genes differentially expressed in FMR1-FM carriers compared with controls. Among these genes, NR3C1 and VIM were previously identified as target RNAs of FMRP (see, e.g. Miyashiro et al. (2003) Neuron, 37, 417-431), although the mRNA expression changes of these genes in FMR1-FM have not been reported.

Brown et al (see, e.g. Brown et al. (2001) Cell, 107, 477-87) previously identified 144 genes as differentially expressed in lymphoblasts with FMR1-FM using pooled fragile X lymphoblastoid cells and pooled normal lymphoblastoid cells. Because there was no overlap except for FMR1 between these 144 genes and the 120 genes identified here with our most stringent analyses using ANOVA, SAM and RankProd, we used the larger gene list identified by either SAM and/or RankProd to compare with the 144 genes identified by Brown et al. We found that 13 genes were shared in these gene lists, including iduronate 2-sulfatase (IDS), hairy and enhancer of split 1 (HES1) and immunoglobulin superfamily, member 3 (IGSF3) as up-regulated genes and CDK2-associated protein 2 (CDK2AP2), ubiquitin specific peptidase 8 (USP8), MAX-like protein X (MLX), ribosomal protein S5 (RPS5), C-terminal binding protein 1 (CTBP1), spleen tyrosine kinase (SYK), F-box protein 6 (FBXO6), mitogen-activated protein kinase kinase kinase 11 (MAP3K11), sorting nexin 15 (SNX15) and CD44 antigen (CD44) as down-regulated genes. Although these genes have not been reported as associated with FMR1 or autism, HES1 was associated with attention-deficit hyperactive disorder (ADHD) (see, e.g. Brookes et al. (2006) Mol. Psychiatry, 10, 934-953), which is a symptom frequently seen in FXS (50) and overlapping with ASD (see, e.g. Todd, R. D. (2001) Child Adolesc. Psychiatr. Clin. N. Am., 10, 209-24). The relatively low overlap between the two gene lists could be due to the difference of clinical features of individuals (autism vs. not specific for autism), experimental design (each individual vs. pooled), microarray platforms (Agilent vs. Affymetrix) and the statistical analysis used to find the differential expression between groups. The initial study (see, e.g. Brown et al. (2001) Cell, 107, 477-87) whose primary aim was to find FMRP ligand mRNPs was relatively underpowered to detect overall differences in gene expression and our study used very conservative statistical criteria. However, this core set of genes provides an interesting gene list for further investigation.

Gene Expression Profiles of Lymphoblastoid Cells with dup (15q)

We identified 80 genes differentially expressed in dup(15q) carriers compared with controls. Among these genes, 4 genes located in 15q11-q13 (the region of duplication) UBE3A, CYFIP1, NIPA2, and GOLGA8F were all induced. It is important to note that 5 other genes located in the duplicated region, tubulin gamma complex associated protein 5 (TUBGCP5), HERC2, HERC2 pseudogene 2 (HERC2P2), NIPA1, and ATP10A and were also identified as up-regulated genes by at least one of the three different statistical analyses (see supplemental table S3 in Nishimura et al., Human Molecular Genetics 2007 16(14): 1682-1698, the contents of which are incorporated herein by reference). Four other genes in the duplicated region, gamma-aminobutyric acid A receptor (GABR) beta 3 (GABRB3), GABR alpha 5 (GABRA5), GABR gamma 3 (GABRG3), oculocutaneous albinism II (OCA2) and necdin homolog (NDN), were not expressed at detectable levels in the lymphoblastoid cells. It is important to emphasize that the 15q11-q13 region is subject to paternal imprinting. Three paternally imprinted genes, makorin ring finger protein 3 (MKRN3), MAGE-like 2 (MAGEL2) and SNRPN upstream reading frame (SNURF)-small nuclear ribonucleoprotein polypeptide N (SNRPN) were expressed in the lymphoblasts, but showed no significant changes relative to controls. This data is consistent with the fact that the duplicated region was maternally derived in all 7 cases analyzed in this study. So, overall, these findings suggest that the genes located in the duplicated region were globally upregulated except for the paternally imprinted genes. Global upregulation due to gene-dosage has also been reported in Down syndrome (see, e.g. Tang et al. (2004) Ann. Neurol., 56, 808-814; and Mao et al. (2003) Genomics, 81, 457-467).

Baron et al (see, e.g. Baron et al. (2006) Hum. Mol. Genet, 15, 853-869) identified 81 known genes as differentially expressed in lymphoblastoid cells with dup(15q) (7 individuals) compared to controls (8 individuals) using the Affymetrix platform. They identified upregulation of UBE3A, NIPA1, NIPA2 and HERC2, consistent with our results. We used the gene list identified by SAM and/or RankProd to compare with the 81 genes identified by Baron et al and identified 11 other genes shared in the two gene lists, a significant overlap (the hypergeometric probability is 0.001). These genes were abhydrolase domain containing 6 (ABHD6), potassium channel, subfamily K, member 1 (KCNK1), hypothetical protein KIAA1147, and zinc finger, DHHC domain containing 14 (ZDHCC14) as up-regulated and Rho GTPase activating protein 25 (ARHGAP25), clone LOC387882, leukotriene B4 12-hydroxydehydrogenase (LTB4DH), clone MGC27165, PFTAIRE protein kinase 1 (PFTK1), zinc finger protein 43 (ZNF43) and ring finger protein 41 (RNF41) as down-regulated. The relationships between these genes and autism remain unknown. Again, as is the case of FMR1-FM, these genes represent a set of independently replicated genes between two studies.

Significant Overlap of Dysregulated Genes in Autism with FMR1-FM and dup(15q)

We identified 68 genes that were dysregulated in both autism with FMR1-FM and dup(15q), a very significant result (hypergeometric probability of this overlap is 1.2×10-153). However, we can not formally exclude the possibility that some of the 68 common dysregulated genes might be related to common pathways between FMR-FM and dup(15q) unrelated to ASD. Microarray analysis using lymphoblastoid cells with FMR1-FM or dup(15q), but without ASD is needed to exclude the possibility, as was done in Tuberous Sclerosis cases with and without autism (see, e.g. Tang et al. (2004) Ann. Neurol., 56, 808-814).

We found that the expression of CYFIP1 was significantly induced in autism with dup(15q). CYFIP1 protein has been shown to antagonize FMRP in the eye and nervous system of Drosophila (see, e.g. Schenck et al. (2003) Neuron, 38, 887-98). In FXS, the absence of FMRP, a binding partner to CYFIP1, results in excess free CYFIP1 protein. Similarly, excess free CYFIP1 protein may be the outcome of dup(15q). Thus, antagonization of FMRP by over-expression of CYFIP1 protein, and/or alternate actions of excess CYFIP1 protein may be common mechanistic links between FMR1-FM and dup(15q).

Effect of FMR1 and CYFIP1 on the Commonly Dysregulated Genes in SH-SY5Y and Mouse Brain We validated the effect of down-regulation of FMR1 in SH-SY5Y cells and mouse brain and up-regulation of CYFIP1 in SH-SY5Y cells on the expression of the commonly dysregulated genes identified in patient lymphoblastoid cells. We demonstrated that the expression of JAKIMIP1 and GPR155 were dysregulated by reduction of FMR1 and induction of CYFIP1 in SH-SY5Y cells. JAKMIP1 protein was also dysregulated by knock-out of FMR1 in mouse brain. Interestingly, the direction of changes observed in both of these genes is opposite in neural tissues (SH-SY5Y cells and brain) and lymphoblastoid cells. Such differences between brain and blood cells have been previously observed in other signaling pathways (see, e.g. Iwamoto et al. (2004) Mol. Psychiatry, 9, 406-416; and Middleton et al. (2005) Am. J. Med. Genet. B Neuropsychiatr. Genet., 136, 12-25). It is likely that it is not the precise direction observed in lymphoblastoid cells that is most important, but the common dysregulation of JAKMIP1 and GPR155, downstream of these single gene defects and which is observed in idiopathic ASD.

JAKMIP1 is associated with janus kinases (see, e.g. Steindler et al. (2004) J. Biol. Chem., 279, 43168-43177), microtubles (see, e.g. Steindler et al. (2004) J. Biol. Chem., 279, 43168-43177) and GABRB receptors (see, e.g. Couve et al. (2004) J. Biol. Chem., 279, 13934-13943). The expression levels of JAKMIP1 affect the intracellular levels of the GABRB receptor (see, e.g. Couve et al. (2004) J. Biol. Chem., 279, 13934-13943). Because the GABRB receptor could interact with the metabotropic glutamate receptor 1 (mGluR1) and increase the glutamate sensitivity of mGluR1 (see, e.g. Tabata et al. (2004) Proc. Natl. Acad. Sci. USA, 101, 16952-16957), JAKMIP1 might affect mGluR1 signaling through GABRB receptors. It is important to note that mGluR signaling is exaggerated in FMR1 knock-out mouse (see, e.g. Bear et al. (2004) Trends. Neurosci., 27, 370-377) and that glutamergic and GABAergic system have been reported to be abnormal in autism (see, e.g. Polleux et al. (2004) Ment. Retard. Dev. Disabil. Res. Rev., 10, 303-317). JAKMIP1 is highly expressed throughout the mouse brain, especially in hippocampus where GABRB receptors and mGluR1 are also highly expressed (see, e.g. Allen Brain Atlas. (http://www.brain-map.org/)). Although the function of GPR155 is unknown, it is highly expressed in the limbic system in mouse brain (see, e.g. Allen Brain Atlas. (http://www.brain-map.org/)), suggesting that GPR155 might have functions relevant to the limbic system.

It is also interesting to consider how the reduction of FMR1 and the induction of CYFIP1 might regulate the expression of JAKMIP1 and GPR155. G-quadruplex motifs in RNA have been shown to play significant roles in FMRP binding (see, e.g. Darnell et al. (2001) Cell, 107, 489-99). Using QGRS mapper (see, e.g. Kikin et al. (2006) Nucleic Acids Res., 34, W676-682), we found that human and mouse JAKMIP1 each had two of the G-quadruplex (G2N2-4G2N2-4G2N2-4G2) and that human and mouse GPR155 had five and one of the G-quadruplex, respectively. FMRP can also bind target RNAs through non-coding RNAs (see, e.g. Zalfa et al. (2003) Cell, 112, 317-327) or microRNAs (see, e.g. Jin et al. (2004) Nat. Cell. Biol., 6, 1048-1053). Using miRBase (see, e.g. Griffiths-Jones et al. (2006) Nucleic Acids Res., 34, D140-144), we found putative microRNA binding sites in human and mouse JAKIMIP1 and GPR155. Further studies are required to clarify the functional importance of JAKMIP1 and GPR155 in autism and the mechanism of regulation of these genes by FMR1 and CYFIP1. In this regard, the potential link with neuronal transmission is intriguing.

The Expression of JAKMIP1 and GPR155 were also Dysregulated in 27 Males with Idiopathic ASD The findings in autism with FMR1-FM and dup(15q) suggest that JAKMIP1 and GPR155 may be involved more generally in idiopathic ASD, since their dysregulation is observed in neural cells and brain. We tested whether dysregulation of these genes were more generalizable in an independent sample consisting of idiopathic ASD cases. To attempt to reduce the heterogeneity of idiopathic ASD and extend these findings beyond those with mental retardation or intellectual disability, we used an IQ surrogate based on Raven's Progressive Matrices, which is highly correlated with IQ defined by other measures (see, e.g. Mottron, L. (2004) J. Autism Dev. Disord., 34, 19-27). We selected 27

ASD males with an IQ score over 70. These data demonstrated that the expression of JAKMIP1 and GPR155 are significantly dysregulated in lymphoblastoid cells from idiopathic ASD compared to controls. These results based on independent data on lymphoblastoid cell gene expression from ASD subjects with FMR1-FM, or dup(15q), as well as idiopathic ASD suggest that JAKMIP1 and GPR155 may be useful as biomarkers for ASD.

The mechanism for the opposite regulation of JAKMIP1 and GPR155 in lymphobastoid cells and neural cells remain to be elucidated. There are several previous reports of genes showing the opposite expression between lymphoblastoid cells and brains in neuropsychiatric disease. One example is inositol monophosphatase 2 (IMPA2) that has been identified as a plausible locus for bipolar disorder (see, e.g. Yoshikawa et al. (1997) Mol. Psychiatry, 2, 393-397; Nothen et al. (1999) Mol. Psychiatry, 4, 76-84; and Lin et al. (2005) Am. J. Hum. Genet., 77, 545-555). The expression of IMPA2 was reduced and induced in lymphoblastoid cells and brains, respectively, in patients with patients with bipolar disorder (see, e.g. Yoon et al. (2001) Mol. Psychiatry, 6, 678-683). A genetic association between IMPA2 promoter polymorphism and bipolar disorder has been confirmed (see, e.g. Sjoholt et al. (2004) Mol. Psychiatry, 9, 621-629; and Ohnishi et al. (2007) Neuropsychopharmacology). In this regard, it is notable that GPR155 is located on 2q31.1, 300 kb from D2S2188, which has shown strong linkage to autism in studies by two independent groups (see, e.g. IMGSAC (2001) Am. J. Hum. Genet., 69, 570-581; and Romano et al. (2005) Psychiatr. Genet., 15, 149-150). Association analysis for GPR155 and JAKMIP1 are ongoing using the large AGRE cohort. These data provide the first identification and independent validation of the potential roles of JAKMIP1 and GPR155 dysregulation in ASD. Further work is needed to understand the functional consequences of these changes in the developing brain, and to assess the general utility of these and other genes as potential biomarkers.

Materials and Methods

Individuals and Lymphoblastoid Cells Analyzed in this Study

We have analyzed individuals diagnosed with ASD using standard validated measures, including the Autism Diagnostic Interview (ADI-R) (see, e.g. Lord et al. (1994) J. Autism Dev. Disord., 24, 659-685) and Autism Diagnostic Observation Schedule (ADOS) (see, e.g. Lord et al. (2001) Am. J. Med. Genet., 105, 36-38). Eight males with FMR1-FM and 3 males with dup(15q) were drawn from AGRE (see, e.g. Geschwind et al. (2001) Am. J. Hum. Genet., 69, 463-466) (http://www.agre.org/). An additional 4 males with dup(15q) were obtained from NIGMS Human Genetic Cell Repository. 27 males without autism, FMR1-FM and dup(15q) were drawn from the AGRE for controls. In addition, another 27 males with idiopathic ASD who had unaffected male siblings were chosen from AGRE for a comparison sample (see supplemental table S1 in Nishimura et al., Human Molecular Genetics 2007 16(14): 1682-1698, the contents of which are incorporated herein by reference). Surrogate IQ scores (using the Raven Progressive Matrices) were available. FMR1-FM and dup(15q) were examined by PCR and fluorescence in situ hybridization, respectively. The 15q11-q13 duplicated region in the 7 males analyzed in this study were all maternally derived. We also used 14 other individuals from AGRE for common reference (pool) in microarray analysis. Lymphoblastoid cell lines (human Epstein-Barr virus transformed lymphocytes) from these individuals were available from AGRE and NIGMS cell repositories.

The lymphoblastoid cells of the subjects were grown in RPMI 1640 medium with 2 mM L-glutamine and 25 mM HEPES (Invitrogen, Carlsbad, Calif., USA), 10% fetal bovine serum, 1× Antibiotic-Antimycotic solution (Invitrogen, Carlsbad, Calif., USA) at 37° C. in a humidified 5% CO2 Chamber. Cells were grown to a density of $6\times10^5$/ml. Special attention was given to maintain all the cell lines in the same conditions to minimize environmental variation.

Microarray Experiment

A total of $9\times10^6$ of lymphoblastoid cells were seeded out in a T-75 flask in 30 ml of fresh medium. After 24 hours, total RNA was extracted from the cells using RNeasy Mini Kit with DNase treatment (Qiagen, Valencia, Calif., USA) according to manufacturer's protocol. The RNA quantity and quality was measured by ND-100 (Nanodrop, Wilmington, Del., USA) and 2100 Bioanalyzer (Agilent, Santa Clara, Calif., USA), respectively.

Target preparation was performed using Low RNA Input Fluorescent Linear Amplification Kit (Agilent, Santa Clara, Calif., USA) according to the manufacturer's protocol. We extracted total RNA from lymphoblastoid cells from each individual and made target and labeled it with Cy5 fluorescence. We also made reference target by using pooled total RNA from the 14 individuals for reference and labeled it with Cy3 fluorescence. The generated targets were mixed and subjected to hybridization to the Whole Human Genome Array G4112A (Agilent, Santa Clara, Calif., USA) according to the manufacturer's protocol. Scanning of the microarrays were done by DNA microarray scanner (Agilent, Santa Clara, Calif., USA).

Scanner output image files were normalized and filtered by using Feature Extraction Software v8.5 (Agilent, Santa Clara, Calif., USA). Normalization was performed so that overall intensity ratio of Cy5 to Cy3 was equal to one. Probes with signal to noise ratio >2.7 in both Cy3 and Cy5 in at least 14 of 15 controls were used for further analysis.

Statistical Analysis of Microarray Data

ANOVA was performed by MeV3.1 (see, e.g. Saeed et al. (2003) Biotechniques, 34, 374-378). P value was calculated based on 1000 permutation. Hierarchical clustering using Spearman's rank correlation with average linkage clustering were performed by MeV3.1 Principal component analysis was performed by GeneSpring GX7.3 (Agilent, Santa Clara, Calif., USA). SAM (see, e.g. Tusher et al. (2001) Proc. Natl. Acad. Sci. USA, 98, 5116-5121) and RankProd (see, e.g. Breitling et al. (2004) FEBS Lett., 573, 83-92) were performed using Bioconductor (see, e.g. Gentleman et al. (2004) Genome Biol., 5, R80) packages Siggene and RankProd, respectively. 100 and 1000 permutation were performed for cross-validation in SAM and RankProd, respectively. We used three different statistical tests to conservatively identify the most robustly differentially expressed genes. Numerous feature selection methods have been applied to the identification of differentially expressed genes in microarray data (see, e.g. Jeffery et al. (2006) BMC Bioinformatics, 7, 359). The genes commonly identified by ANOVA, SAM and RankProd are likely to be differentially expressed, given the relative robustness of these statistical approaches (see, e.g. Cui et al. (2003) Genome Biol., 4, 210; Tusher et al. (2001) Proc. Natl. Acad. Sci. USA, 98, 5116-5121; Breitling et al. (2004) FEBS Lett., 573, 83-92; and Jeffery et al. (2006) BMC Bioinformatics, 7, 359). Functional Annotation Clustering was performed by DAVID (see, e.g. Dennis et al. (2003) Genome Biol., 4, P3) with medium classification stringency. The clustering algorithm is based on the hypothesis that similar annotations should have similar gene members. The Functional Annotation Clustering uses two different statistics to measure the degree of the common genes between two annotations and to classify the groups with similar annotations. The Group Enrichment Score is the geometric mean (in −log scale) of a member's p-values in a corresponding annotation cluster. IPA was used to find significant pathways related to the genes commonly dysregulated in autism with FMR1-FM and dup (15q). The Ingenuity Pathway Knowledge Base builds gene networks based upon known protein and gene interactions (see, e.g. Ingenuity Pathway Analysis, e.g. by searching "www.ingenuity.com"). IPA determines a statistical score for each network according to the probability of the network given the gene list. The Ingenuity Pathway Knowledge Base provides pathways with biological function based upon the scientific literature. The significance value associated with Functions and Pathways measures how likely it is that genes from the dataset file participate in that biological function. The significance was expressed as a p-value, which is calculated using the right-tailed Fisher's Exact Test.

Quantitative Real Time PCR Analysis (qRTPCR)

Total RNAs was used to make cDNA by SuperScript III First-Strand Synthesis SuperMix (Invitrogen, Carlsbad, Calif., USA). qRTPCR was done by ABI Prism 7900 using Platinum SYBR Green qPCR SuperMix UDG with ROX (Invitrogen, Carlsbad, Calif., USA). Thermal cycling consisted on an initial step at 50° C. for 2 min followed by another step at 95° C. for 2 min and 50 cycles of 95° C. for 15 sec and 60° C. for 30 sec. qRTPCR was performed for 16 genes. The primers used in this study are shown in Supplementary table S4 in Nishimura et al., Human Molecular Genetics 2007 16(14): 1682-1698, the contents of which are incorporated herein by reference. TaqMan probe (Hs00327005_m1, Applied Biosystems, Foster City, Calif., USA) was used to measure JAKMIP1 expression in lymphoblastoid cells. Data was normalized by the quantity of hypoxanthine phosphoribosyltransferase 1 (HPRT1). HPRT1 was selected rather than beta-actin, glyceraldehyde-3-phosphate dehydrogenase or other possible internal controls because it was shown to be most stable RNA species from the lymphoblastoid cell lines. This allowed us to account for the variability in the initial template concentration as well as the conversion efficiency of the reverse transcription reaction.

Transfection of shRNA

To construct retrovirus vectors expressing shRNAs, oligonucleotides encoding stem-loop shRNAs for FMR1 (see supplementary table S4 in Nishimura et al., Human Molecular Genetics 2007 16(14): 1682-1698, the contents of which are incorporated herein by reference) and negative control were ligated into the BamHI and EcoRI site of the pSIREN-RetroQ (BD Clontech, Mountain View, Calif., USA). PT67 cells (BD Clontech, Mountain View, Calif., USA) were transfected for retrovirus production. A total of 6×106 of SH-SY5Y cells were seeded out in a T-75 flask in 20 ml of fresh medium of DMEM (Invitrogen, Carlsbad, Calif., USA) with 10% FBS. After 1 day, SH-SY5Y cells were infected with retroviruses in the presence of 5 μg/ml of polybrene. After 2 days, the SH-SY5Y cells were treated with 10 μg/ml of puromycin (Sigma, St. Louis, Mo., USA). Cells that survived after 4 weeks were collected and this population of cells was used for further experiments. Total RNA were extracted from the cells using RNeasy Mini Kit with DNase treatment (Qiagen, Valencia, Calif., USA) according to the manufacturer's protocol. We compared SH-SY5Y cells expressing FMR1 shRNA (n=4) and SH-SY5Y cells expressing shRNAs for negative control (n=4) to examine the effect of reduction of FMR1 on the expression of JAKMIP1 and GPR155.

Transfection of CYFIP1

The human CYFIP1 coding region (aa 1-1254) obtained by PCR using IMAGE clone 10625411 (ATCC, Manassas, Va., USA) was subcloned into the EcoRV and NotI sites of the plasmid vector pIRES-neo3 (BD Clontech, Mountain View, Calif., USA). The sequence of the construct was confirmed by automated DNA sequencing.

A total of 6×106 of SH-SY5Y cells were seeded out in a T-75 flask in 20 ml of fresh medium of DMEM (Invitrogen, Carlsbad, Calif., USA) with 10% FBS. After 1 day, SH-SY5Y cells were transfected with 120 ul of lipofectamine 2000 (Invitrogen, Carlsbad, Calif., USA) diluted with 3 ml of OptiMEM (Invitrogen, Carlsbad, Calif., USA) and 24 g of plasmid (pIRES-CYFIP1 or pIRES) diluted with 3 ml of OptiMEM (Invitrogen, Carlsbad, Calif., USA). After 5 min at room temperature, they were combined and incubated for 20 min. The reaction mixture was added with 16 ml of DMEM with 10% FBS. The cell culture medium was replaced by this solution. After 2 days, the SH-SY5Y cells were treated with 500 μg/ml of G418 (Invitrogen, Carlsbad, Calif., USA). Cells that survived after 3 weeks were collected and this population of cells was used for further experiments. Total RNA was extracted from the cells using RNeasy Mini Kit with DNase treatment (Qiagen, Valencia, Calif., USA) according to the manufacturer's protocol. We compared SH-SY5Y cells stably transfected with expression vector for CYFIP1 (n=7) and SH-SY5Y cells transfected with empty expression vector (n=8) to examine the effect of induction of CYFIP1 on the expression of JAKMIP1 and GPR155. Protein was also extracted using Cellytic M (Sigma, St. Louis, Mo., USA) with proteinase inhibitors (Sigma, St. Louis, Mo., USA) according to the manufacturer's protocol.

Animals and Tissue Collection

Wild-type (WT) and FMR1 KO mice were raised at the Emory University animal facility and treated in accordance with National Institute of Health regulations and under approval of the Emory University Institutional Animal Care and Use Committee. WT and FMR1 KO littermates were produced by breeding heterozygous females with FMR1 KO males in congenic background of C57BL/6. The genotype of each animal was confirmed by PCR. For tissue collection, cortex were dissected, followed by protein isolation using Cellytic M (Sigma, St. Louis, Mo., USA) with proteinase inhibitors (Sigma, St. Louis, Mo., USA) according to the manufacturer's protocol.

Immunoblot Analysis

The proteins extracted from SH-SY5Y cells or cortex of FMR1 WT and KO mice were subjected to SDS-PAGE using NuPAGE Novex 4-20% Bis-Tris gel and MOPS buffer (Invitrogen, Carlsbad, Calif., USA) according to the manufacturer's protocol. After electrophoresis, gels were electroblotted onto PVDF membranes (Millipore, Bedford, Mass., USA). After electroblotting, membranes were blocked in SuperBlock blocking buffer (Pierce Biotechnology, Rockford, Ill., USA). Membranes were probed in the blocking solution at 4° C. overnight with the following antibodies: FMRP (Chemicon, Temecula, Calif., USA), CYFIP1 (Upstate, Temecula, Calif., USA), JAKMIP1 (see, e.g. Steindler et al. (2004) J. Biol. Chem., 279, 43168-43177) or GAPDH. Membranes were washed 3× in PBS supplemented with 0.05% Tween 20 (PBS-T) and incubated with the appropriate horseradish peroxidase-conjugated secondary antibody in the blocking solution for 1 hour at room temperature. Membranes were again washed 3× in PBS-T, developed with SuperSignal West Pico Chemiluminescent (Pierce Biotechnology, Rockford, Ill., USA). Membranes were stripped by Restore Western Blot Stripping Buffer (Pierce Biotechnology, Rockford, Ill., USA) and used for different antibodies.

Example 2

Genome-Wide Expression Profiling of Lymphoblastoid Cell Lines Reveals Genes Dysregulated in Autism Spectrum Disorder Autism spectrum disorder (ASD) is a heterogeneous condition and is likely to result from the combined effects of multiple, subtle genetic changes interacting with environmental factors. We hypothesize that there are genes whose expression are deregulated in ASD. We believe that a subset of these genes can be identified through the whole genome expression profiling in lymphoblastoid cells from individuals with autism and control. Although lymphoblastoid cells are not neuronal cells, recent studies suggest that lymphoblastoid cells can be useful to detect biologically plausible correlations between candidate genes and disease in various neuropsychiatric disorders. Our first study using lymphoblastoid cells from ASD subjects with known genetic disorders showed that genome-wide expression profiling of the lymphoblastoid cell lines distinguishes different forms of ASD and reveals shared pathways. Here, we analyzed genome-wide expression profiling of lymphoblastoid cell lines from 15 male sib pairs discordant for idiopathic ASD. We identified genes dysregulated in common among the idiopathic ASD and ASD with known genetic disorders. These results provide evidence that blood derived lymphoblastoid cell gene expression is likely to be useful for identifying susceptibility genes for ASD.

We previously reported that gene expression profiling of lymphoblastoid cell lines could identify different and shared pathways in cases of autism spectrum disorder (ASD) with known genetic causes (see, e.g. Nishimura et al. 2007. Hum Mol Genet 16(14):1682-98). The analysis revealed shared pathways between ASD with full mutation of FMR1 (FMR1-FM) or maternal duplication of 15q11-q13 (dup15q), each of which account for 1-2% of ASD cases in large series. Here, we analyzed genome-wide expression profiling of lymphoblastoid cell lines from 15 male sib pairs discordant for idiopathic ASD. We identified 95 genes dysregulated in common among the idiopathic ASD, ASD with FMR1-FM and ASD with dup15q. We also identified 19 genes whose expression levels were extremely different in one of the 15 affected males compared to the mean of the 15 male sib pairs. We were able to confirm the differential expression of JAKMIP1, STEAP1, SLC16A6 and VIM between 39 male sib pairs discordant for ASD by quantitative PCR analysis. These results provide evidence that blood derived lymphoblastoid cell gene expression is likely to be useful for identifying susceptibility genes for ASD.

In this study, we analyzed the genome-wide expression profiles of lymphoblastoid cells from 15 male sib pairs discordant for idiopathic ASD. ASD is heterogeneous condition that is likely to result from the combined effects of multiple genetic factors (see, e.g. Abrahams et al. 2008. Nat Rev Genet 9(5):341-55; Geschwind D H. 2008a. Nature 454(7206):838-9; Geschwind D H. 2008b. Cell 135(3):391-5; and Geschwind et al. 2007. Curr Opin Neurobiol 17(1):103-11). Recent technological developments, such as array-based comparative genomic hybridization (array-CGH), revealed strong association of de novo copy number variation (CNV) with ASD (see, e.g. Sebat et al. 2007. Science 316(5823):445-9). However, each de novo CNV was individually rare in the population of patients (see, e.g. Christian et al. 2008. Biol Psychiatry 63(12):1111-7; Glessner et al. 2009. Nature; Marshall et al. 2008. Am J Hum Genet 82(2):477-88; Sebat et al. 2007. Science 316(5823):445-9; and Szatmari et al. 20007. Nat Genet 39(3):319-28), suggesting that genes located within the CNV would be differentially expressed only in a subset of ASD. Although these genes may not be involved in ASD in the general population, it is highly likely that they can provide essential information with regard to biological pathways and genetic networks involved in the etiology of ASD. In this study, we focused our attention on (i) genes that were dysregulated in common among idiopathic ASD, ASD with FMR1-FM and ASD with dup15q and (ii) genes whose expression levels were extremely different in a subset of the 15 affected males compared to the mean of the 15 male sib pairs discordant for idiopathic ASD. Here, we demonstrate 92 genes dysregulated in common among the three different forms of ASD and 19 genes whose expression levels were extremely different (over 4 SD from the mean) in one of the 15 affected males. We were able to confirm the differential expression of janus kinase and microtubule interacting protein 1 (JAKMIP1), six transmembrane epithelial antigen of the prostate 1 (STEAP1), solute carrier family 16 member 6 (SLC16A6) and vimentin (VIM) between 39 male sib pairs discordant for idiopathic ASD by using quantitative PCR analysis (qPCR). These results suggest that genome-wide expression profiling of lymphoblastoid cells is an efficient strategy to identify susceptibility genes for ASD.

Materials and Methods

Individuals and Lymphoblastoid Cells Analyzed in this Study

We have analyzed individuals diagnosed with ASD using standard validated measures, including the Autism Diagnostic Interview (ADI-R) (see, e.g. Lord et al. 1994. J Autism Dev Disord 24(5):659-85) and Autism Diagnostic Observation Schedule (ADOS) (see, e.g. Lord et al. 2001. Am J Med Genet 105(1):36-8), and controls (Table 3). All individuals were drawn from AGRE (see, e.g. Geschwind et al. 2001. Am J Hum Genet 69(2):463-6) (http://www.agre.org/). Lymphoblastoid cell lines (human Epstein-Barr virus transformed lymphocytes) from these individuals were available from AGRE. The lymphoblastoid cells of the subjects were grown as described previously (see, e.g. Nishimura et al. 2007. Hum Mol Genet 16(14):1682-98).

Microarray Experiments

Microarray experiments were performed as described previously (see, e.g. Nishimura et al. 2007. Hum Mol Genet 16(14):1682-98). Scanner output image files from set 1 and 2 were normalized and filtered using Feature Extraction Software v8.5 (Agilent, Santa Clara, Calif., USA). Normalization was performed so that overall intensity ratio of Cy5 to Cy3 was equal to one.

Statistical Analysis of Microarray Data

To identify differentially expressed genes between groups, we analyzed the probes that met following criteria in both Cy3 and Cy5 in at least 13 of the 15 affected males. These criteria were i) signal was not saturated, ii) signal was uniform, iii) signal-to-noise ratio was over 2.6. The expression profile of these probes were subjected to EDGE (see, e.g. Leek et al. 2006. Bioinformatics 22(4):507-8) with 100 permutations for cross-validation. To identify differentially expressed genes (4 SD from the mean), we performed statistical analysis as described in (see, e.g. Coppola et al. 2008. Ann Neurol 64(1):92-6).

qPCR Analysis

One microgram of total RNA was used to make cDNA by iScript cDNA Synthesis Kit (BioRad, Hercules, Calif., USA). The qPCR was performed as described previously (see, e.g. Nishimura et al. 2007. Hum Mol Genet 16(14):1682-98). The primers used in this study were JAKMIP1F; 5'-GGGGAAGCATGTCGAAGAAA-3' (SEQ ID NO: 1), JAKMIP1R; 5'-GGCCTTGAGCTCCGAAATGT-3'3' (SEQ ID NO: 2), STEAP1F; 5'-3', STEAP1R; 5'-3', SLC16A6F; 5'-GGAGCCTTTGGGGGTTTATT-3'3' (SEQ ID NO: 3), SLC16A6R; 5'-CCATCCTCCATCAGGCACTT-3'3' (SEQ ID NO: 4), VIMF; 5'-AGCCGAAAACACCCTGCAATC-3'3' (SEQ ID NO: 5), and VIMR; 5'-CTGGATTTCCTCTTCGTGGAGTT-3'3' (SEQ ID NO: 6).

Identification of Loci Associated with ASD

We used SLEP (see, e.g. Konneker et al. 2008. Am J Med Genet B Neuropsychiatr Genet 147B(6):671-5) to identify loci associated with ASD. SLEP is a searchable archive of findings from psychiatric genetics. The database was queried by gene name in Table 1 using expansion of 5 Mb for genome-wide linkage studies and 5 Kb for genome-wide association studies. We also used Autism Chromosomal Rearrangement Database to identify de novo or overlapping CNVs involving genes identified in this study.

Results

Figure 8:
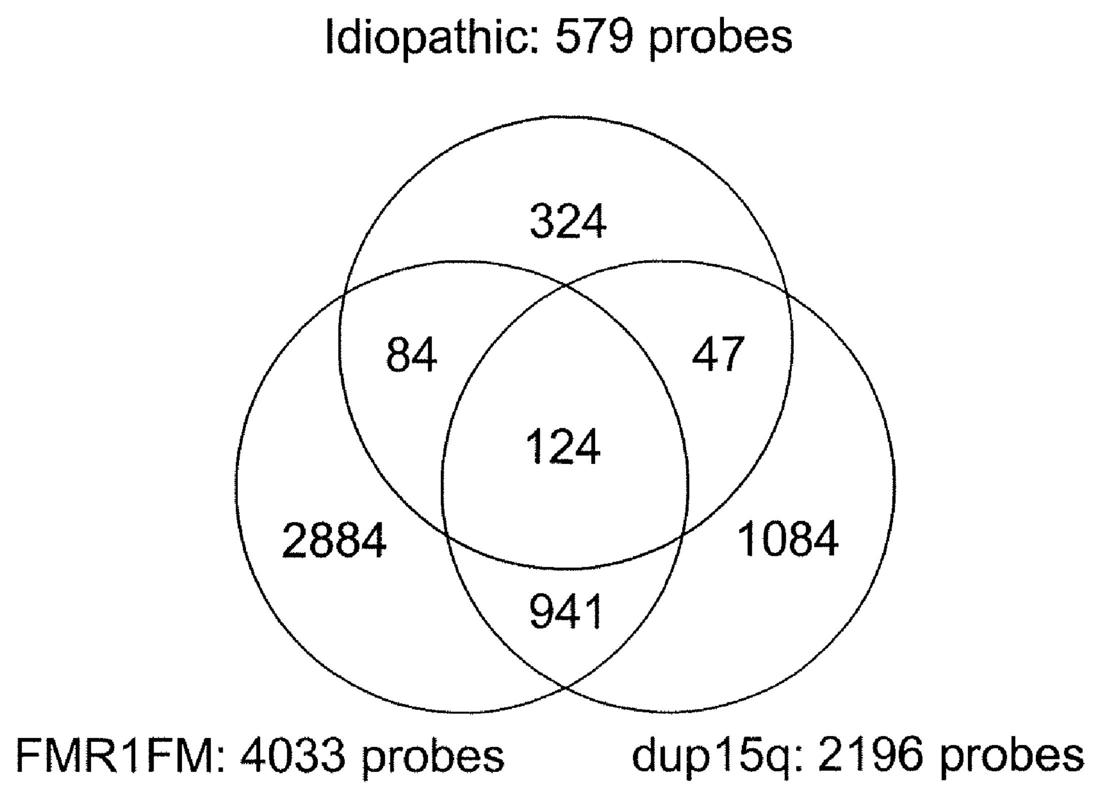
FIG. 8 shows gene networks associated with genes common to FMR1-FM and dup(15q). IPA was used to find significant networks related to the genes dysregulated in both autism with FMR1-FM and dup(15q). Three networks were identified that contained at least 10 genes. Principal functions associated with network A, B and C were cell cycle ($P=5.2\times10^{-8}$), cellular movement ($P=1.3\times10^{-8}$) and molecular transport ($P=1.6\times10^{-8}$), and cell-to-cell signaling and interaction ($P=4.3\times10^{-8}$), respectively. Genes shown in bold were among the genes commonly dysregulated in autism with FMR1-FM and dup(15q). The intensity of node color indicates the degree of up-(red) or down-(green) regulation.

Microarray Analysis Identified 95 Genes Dysregulated in Idiopathic ASD, ASD with FMR1-FM and ASD with dup15q We analyzed the whole-genome mRNA expression profiles in lymphoblastoid cells from 15 male sib pairs discordant for idiopathic ASD (Table 3) in the Autism Genetic Resource Exchange (AGRE) (see, e.g. Geschwind et al. 2001. Am J Hum Genet 69(2):463-6) using Agilent Whole Human Genome Array. Overall, of 41,000 probes analyzed, 25497 probes, representing 13893 genes, were expressed in the lymphoblastoid cells. To find the genes that were differentially expressed between the 15 male sib pairs discordant for idiopathic ASD, the expression profile was subjected to Extraction of Differential Gene Expression (EDGE) (see, e.g. Leek et al. 2006. Bioinformatics 22(4):507-8). EDGE uses newly developed statistical methodology including Optimal Discovery Procedure and shows substantial improvements over five leading methodologies (see, e.g. Leek et al. 2006. Bioinformatics 22(4):507-8). EDGE identified 579 probes below P-value of 5% (FIG. 8). However, none of the probes had false discovery rate (FDR) under 50%, suggesting genetic heterogeneity of these 15 male sib pairs. We previously analyzed genome-wide expression profile of lymphoblastoid cell lines from 6 males with ASD and FMR1-FM and 7 males with ASD and dup15q (see, e.g. Nishimura et al. 2007. Hum Mol Genet 16(14):1682-98). These males comprise two homogeneous subsets of ASD. We reanalyzed the expression profile using EDGE and identified 4033 and 2196 probes dysregulated (FDR <5%) in ASD with FMR1-FM and ASD with dup15q, respectively (FIG. 8). 1065 probes, representing 752 genes, were dysregulated in both ASD with FMR1-FM and dup15q. Consistent with the previous analysis (see, e.g. Nishimura et al. 2007. Hum Mol Genet 16(14):1682-98), this overlap was highly significant (hypergeometric probability, $P=1.8\times10^{-317}$). We compared the 579 probes dysregulated in idiopathic ASD with probes dysregulated in ASD with FMR1-FM and/or ASD with dup15q. As shown in FIG. 8, 208 and 171 probes were also dysregulated in ASD with FMR1-FM and ASD with dup15q, respectively. Hypergeometric probability for these overlap were $P=3.4\times10^{-33}$ (idiopathic ASD and ASD with FMR1-FM) and $P=3.0\times10^{-49}$ (idiopathic ASD and ASD with dup15q), suggesting these overlap were also significant. 124 probes representing 95 genes were dysregulated in common among the three different forms of all ASD (FIG. 8 and Table 1). Among the 95 genes, 32 genes were located within the autism loci previously identified by genetic analysis (Table 1) (see, e.g. Alarcon et al. 2002. Am J Hum Genet 70(1):60-71 Epub 2001 Dec. 6; Alarcon et al. 2005. Mol Psychiatry 10(8):747-57; Allen-Brady et al. 2008. Mol Psychiatry; Auranen et al. 2002. Am J Hum Genet 71(4):777-90 Epub 2002 Aug. 21; Barrett et al. 1999. Am J Med Genet 88(6):609-15; Buxbaum et al. 2001. Am J Hum Genet 68(6):1514-20; Cantor et al. 2005. Am J Hum Genet 76(6):1050-6; Duvall et al. 2007. Am J Psychiatry 164(4):656-62; IMGSAC. 2001. Am J Hum Genet 69(3):570-81; Liu et al. 2001. Am J Hum Genet 69(2):327-40 Epub 2001 Jul. 10; Marshall et al. 2008. Am J Hum Genet 82(2):477-88; Schellenberg et al. 2006. Mol Psychiatry 11(11):1049-60, 979; Sebat et al. 2007. Science 316(5823):445-9; Szatmari et al. 2007. Nat Genet 39(3):319-28; Trikalinos et al. 2006. Mol Psychiatry 11(1):29-36; and Yonan et al. 2003. Am J Hum Genet 73(4):886-97 Epub 2003 Sep. 17).

To provide functional classification of the 95 genes, we used Ingenuity Pathway Analysis (IPA). IPA identified four statistically significant networks, each containing at least 10 genes (Table 4 and FIG. 3). Principal functions associated with these networks were cellular development and cancer (Table 4).

Figure 9:
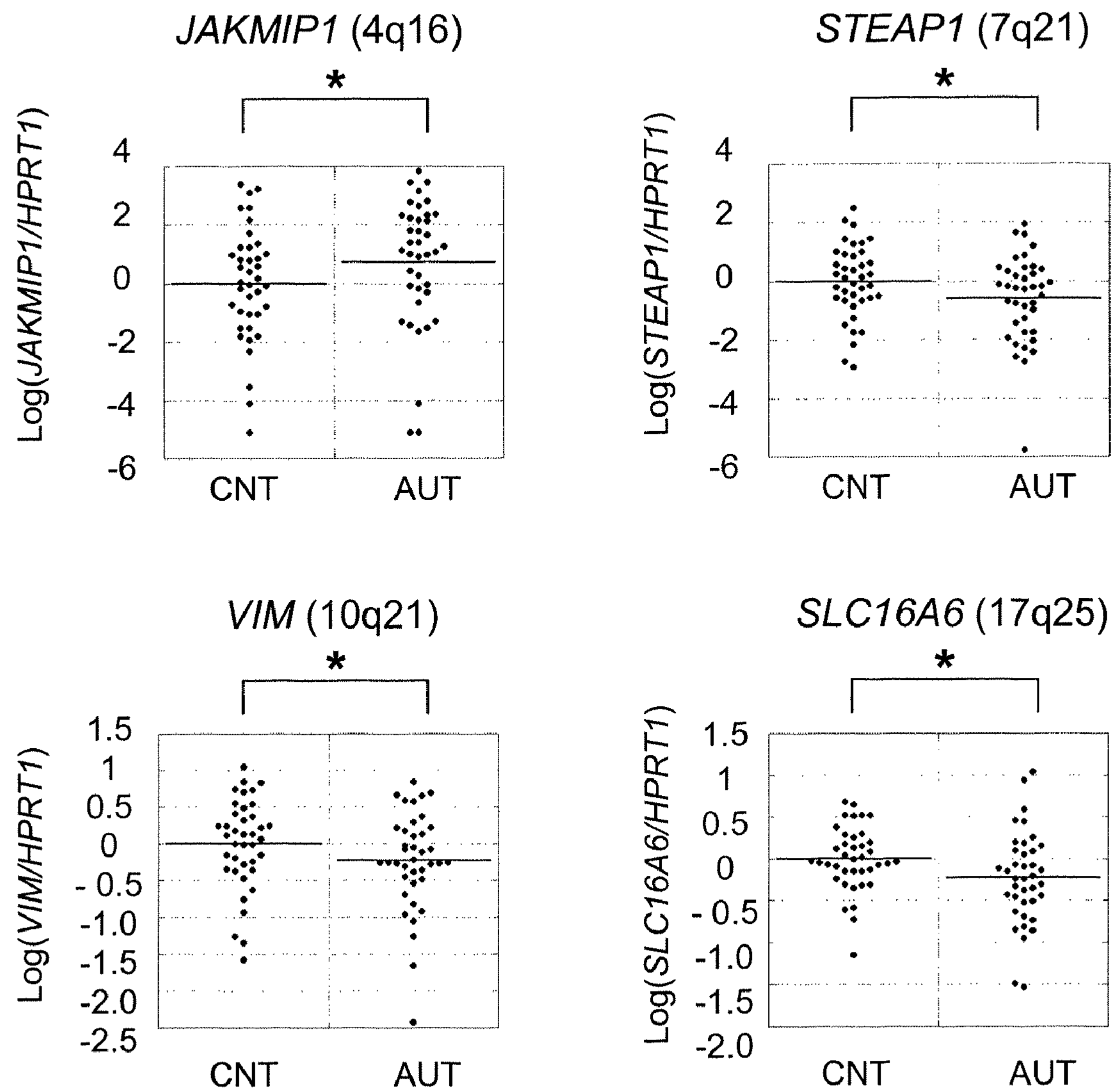
FIG. 9 shows a confirmation of the differential gene expression by qPCR. Total RNA was extracted from lymphoblastoid cells from 36 male sib pairs discordant for idiopathic ASD. qPCR was performed to confirm the differential expression identified by microarray analysis. Bars indicate the mean of the values of each group. The mean of the value of control subjects was set as 0. P-value was calculated by Wilcoxon rank-sum test using control (N=39) and ASD (N=39). *P<0.05.
Figure 10A:
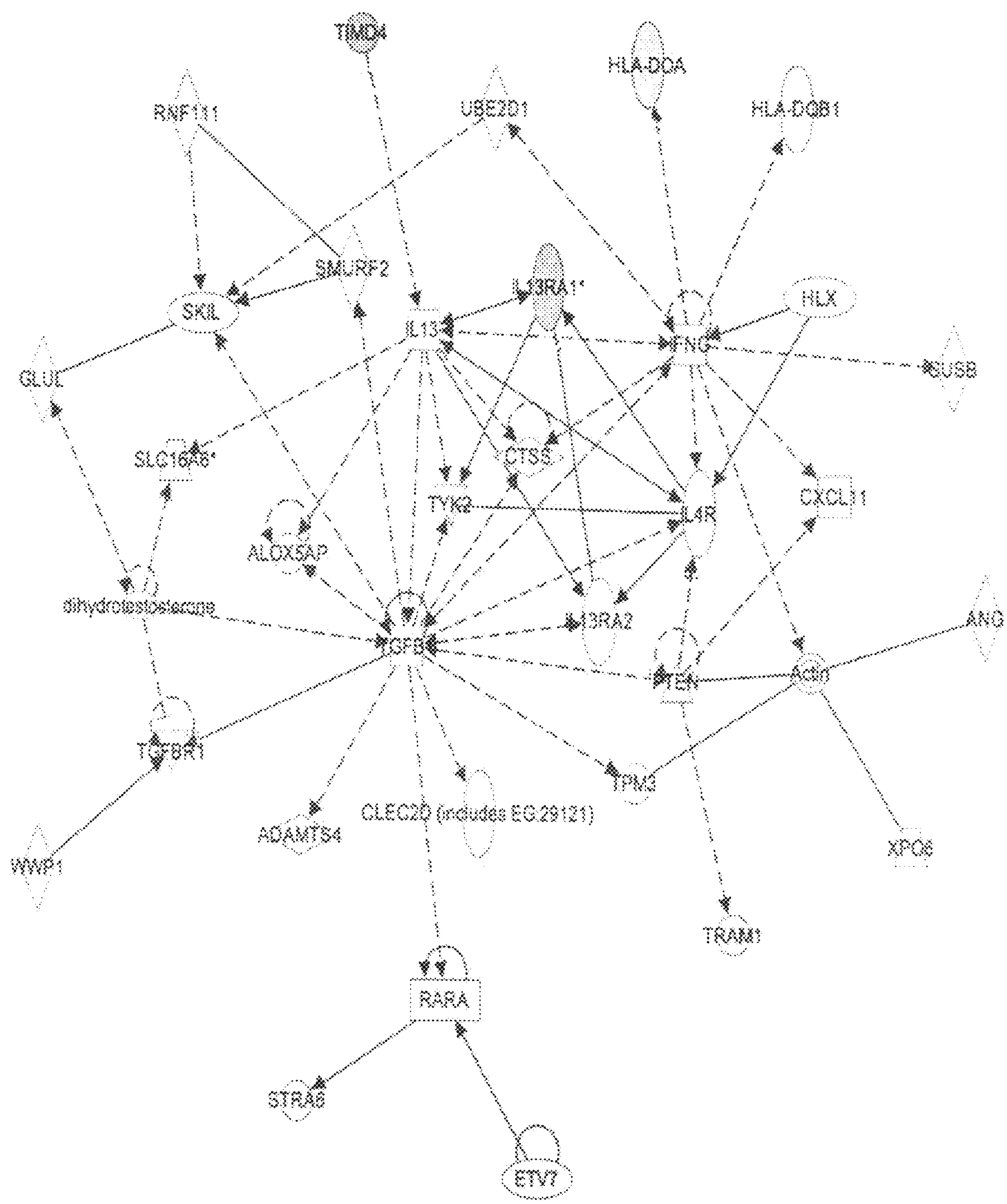
FIG. 10 shows gene networks associated with genes dysregulated in common among idiopathic ASD, ASD with FMR1-FM and ASD with dup15q. IPA was used to find significant networks related to the genes dysregulated in common among the three different forms of ASD. Four networks were identified that contained at least 10 genes. Principal functions associated with network A, B, C and D were cellular development, cancer, cellular development and cancer, respectively. Genes shown in bold were among the genes dysregulated in ASD.
Figure 10B:
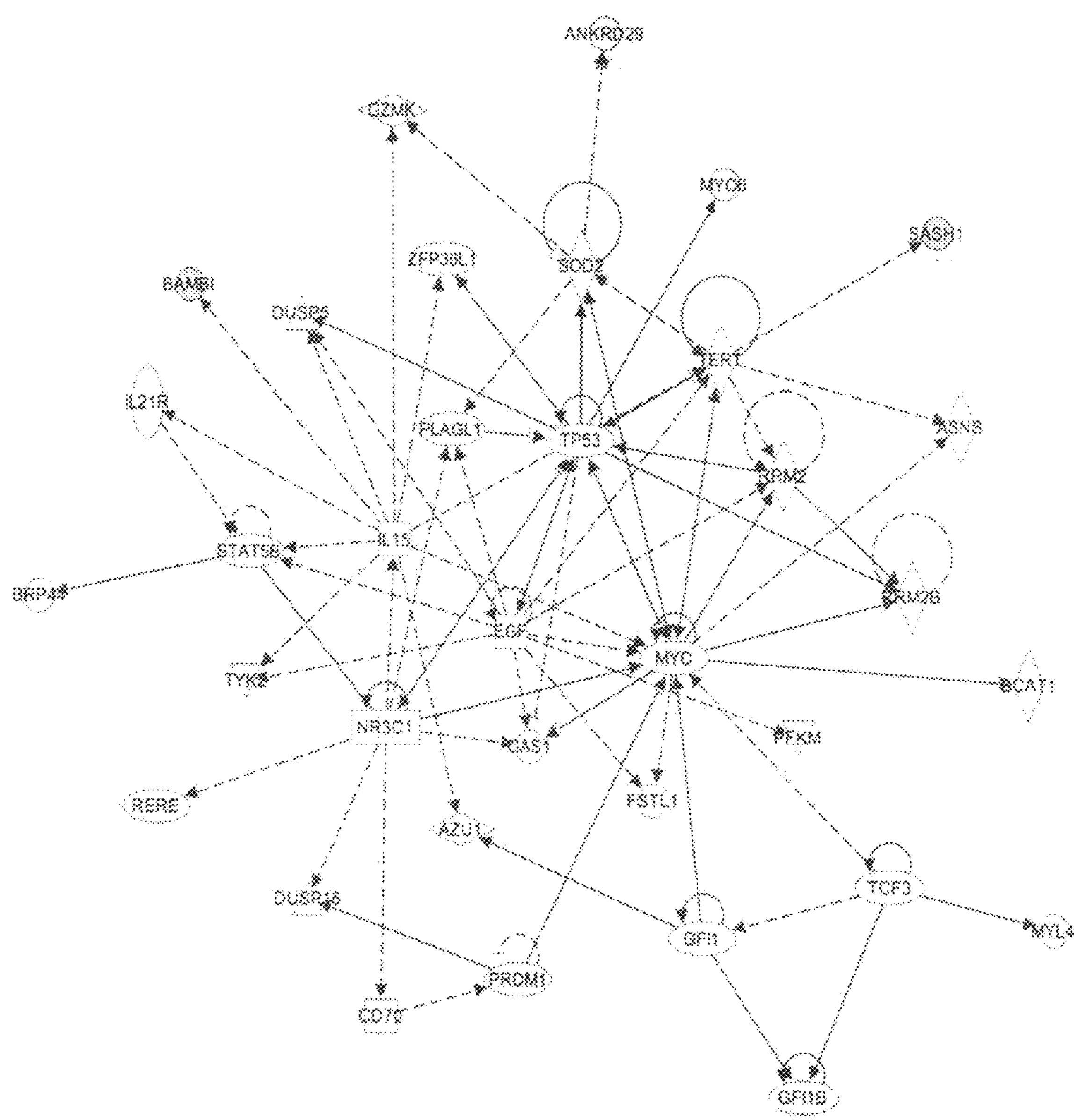
Figure 10C:
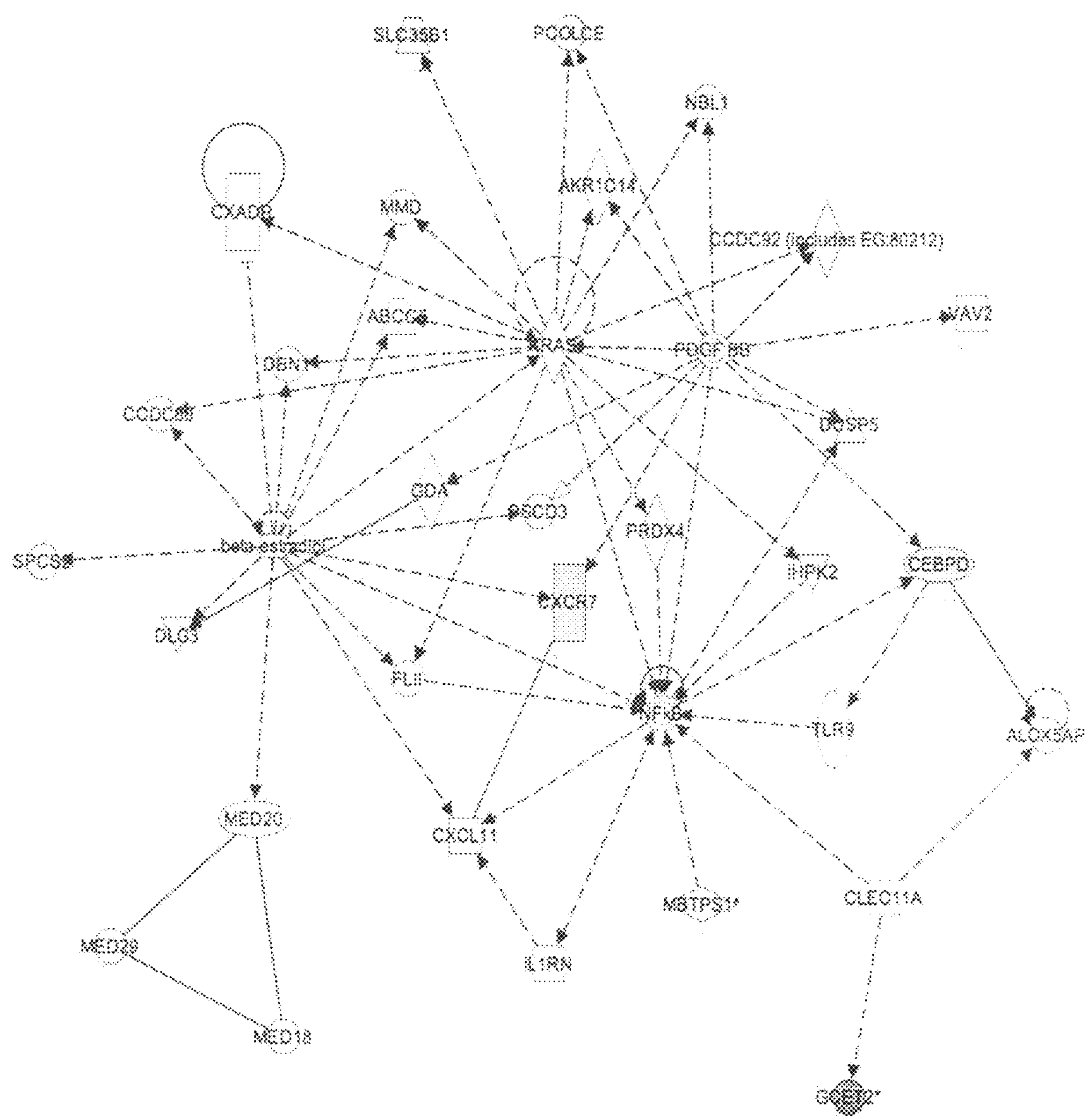
Figure 10D:
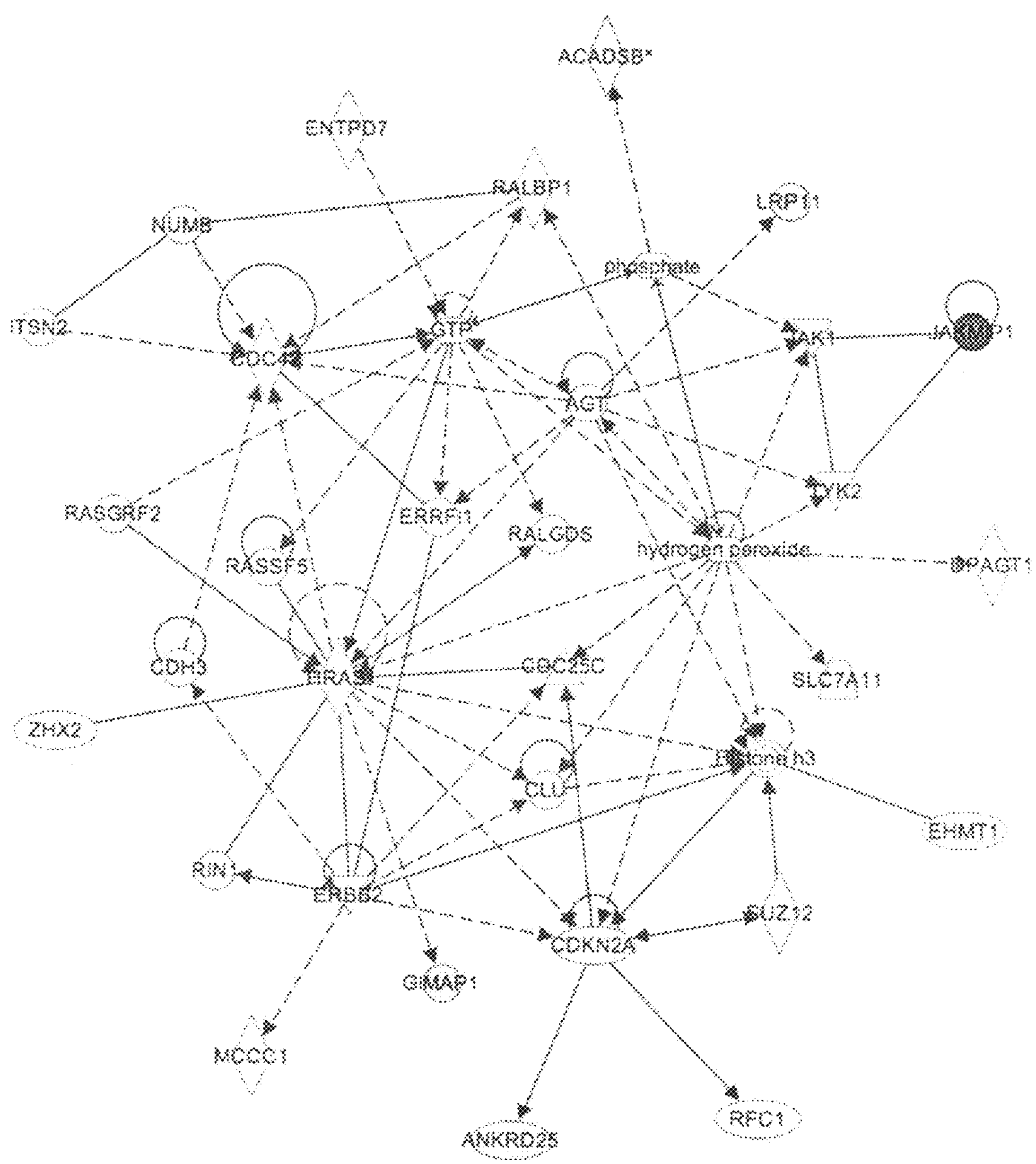

Microarray Analysis Also Identified 19 Genes Whose Expression Levels were Extremely Different in One of the 15 Affected Males We then focused our attention on genes that were differentially expressed (over 4 SD from the mean of 15 male sib pairs) in a subset of the 15 affected males. We identified 19 genes, each of which was differentially expressed (1.7-15 fold change) in only one of the 15 male sib pairs (Table 2). Interestingly, 2 of the 19 genes, GABA A receptor α4 (GABRA4) and oligodendrocyte myelin glycoprotein (OMG) have been reported to have significant association with ASD (see, e.g. Ma et al. 2005. Am J Hum Genet 77(3):377-88; and Martin et al. 2007b. Neurosci Res 59(4):426-30). GABRA4, nicotinate phosphoribosyltransferase domain containing 1 (NAPRT1) and vimentin (VIM) were also located within CNVs that occurred de novo or overlapped in ASD (see, e.g. Kakinuma et al. 2007. Am J Med Genet B Neuropsychiatr Genet; and Weidmer-Mikhail et al. 1998. J Intellect Disabil Res 42 (Pt 1):8-12).

qPCR Confirmed the Differential Expression of JAKMIP1, STEAP1, SLC16A6 and VIM Between 39 Male Sib Pairs Discordant for Idiopathic ASD To validate the differential expression identified by microarray analysis using independent methods, we performed quantitative PCR analysis (qPCR) of JAKMIP1, STEAP1, SLC16A6 and VIM using lymphoblastoid cell lines from 39 male sib pairs discordant for idiopathic ASD (Table 3). The 39 male sib pairs included the 15 male sib pairs analyzed in the microarray study. JAKMIP1 was selected because we previously demonstrated that the expression of JAKMIP1 was significantly different between 27 male sib pairs discordant for idiopathic ASD (see, e.g. Nishimura et al. 2007. Hum Mol Genet 16(14):1682-98). STEAP1, SLC16A6 and VIM were selected because the microarray analysis identified the dysregulation of these genes by multiple probes (Table 1 and 2). To attempt to reduce the heterogeneity of idiopathic ASD, we used an IQ surrogate based on Raven's Progressive Matrices. The 39 affected males had an IQ score of more than 70 (Table 3). As shown in FIG. 9, qPCR confirmed the dysregulation of JAKMIP1, STEAP1, and SLC16A6 as expected by the microarray analysis. qPCR also confirmed the reduction of VIM in one affected male as expected in the microarray analysis (6-fold reduction). The expression of VIM was significantly different between the 39 male sib pairs discordant for idiopathic ASD.

In this study, we performed global mRNA expression profiling of lymphoblastoid cell line from 15 male sib pairs discordant for idiopathic ASD. We focused our attention on (i) genes that were dysregulated in common among idiopathic ASD, ASD with FMR1-FM and ASD with dup15q and (ii)

genes whose expression were extremely different (4 standard deviation from the mean of the 15 male sib pairs) in a subset of the 15 affected males.

Genes Dysregulated in Idiopathic ASD, ASD with FMR1-FM and ASD with dup15q

We first tried to identify genes that were differentially expressed between the 15 male sib pairs discordant for idiopathic ASD. 579 probes were differentially expressed between the 15 male sib pairs. However, none of the 579 probes had FDR fewer than 50%, suggesting genetic heterogeneity of the 15 male sib pairs. It may also reflect that ASD can result from many different genetic defects. Given the complexity of ASD, the study of ASD associated with Mendelian single gene disorders or known chromosomal etiologies provides an important perspective (see, e.g. Belmonte et al 2006. Nat Neurosci 9(10):1221-5; and Geschwind et al. 2007. Curr Opin Neurobiol 17(1):103-11). Previously, we analyzed genome-wide expression profiles of lymphoblastoid cells from ASD with FMR1-FM or dup15q and identified shared pathways between these ASD (see, e.g. Nishimura et al. 2007. Hum Mol Genet 16(14):1682-98). We hypothesized that there might be genes dysregulated in common among idiopathic ASD, ASD with FMR1-FM and ASD with dup15q. Comparing the expression profiles, we identified 95 genes that were dysregulated in common among the idiopathic ASD, ASD with FMR1-FM and ASD with dup15q. qPCR analysis confirmed the differential expression of JAKMIP1, STEAP1 and SLC16A6 between 36 male sib pairs discordant for idiopathic ASD.

JAKMIP1 is associated with Janus kinases (see, e.g. Steindler et al. 2004. J Biol Chem 279(41):43168-77), microtubules (see, e.g. Steindler et al. 2004. J Biol Chem 279(41):43168-77) and GABRB receptors (see, e.g. Couve et al. 2004. J Biol Chem 279(14):13934-43). Because GABRB receptors could interact with the metabotropic receptor 1 (mGluR1) and increase the glutamate sensitivity of mGluR1 (Tabata, et al., 2004), JAKMIP1 might affect mGluR1 signaling through GABRB receptors. GABAergic and glutamergic signaling have been reported to be dysregulated in ASD (Belmonte and Bourgeron, 2006). Two individuals with ASD were reported to have CNVs containing JAKMIP1 (see, e.g. Sebat et al. 2007. Science 316(5823):445-9; and Szatmari et al. 2007. Nat Genet 39(3):319-28), suggesting dysregulation of JAKMIP1 may be involved in the etiology of ASD.

Although the function of STEAP1 is currently unknown, other members of STEAP family are not only ferrireductase but also cupric reductase that stimulate cellular uptake of both iron and copper (see, e.g. Ohgami et al. 2006. Blood 108(4):1388-94). Epitope-tagged STEAP1 expressed in HEK293-T cells partially colocalized with transferrin (Tf) and Tf receptor, suggesting STEAP1 might modulate iron-transport through Tf/Tf receptor (see, e.g. Ohgami et al. 2006. Blood 108(4):1388-94). It is important to note that levels of Tf and ceruloplamsin (copper-binding protein) in the serum were significantly reduced in children with ASD as compared to their developmentally normal siblings (see, e.g. Chauhan et al. 2004. Life Sci 75(21):2539-49). These findings suggest that STEAP1 may be related to the pathophysiology of ASD. It was shown that a SNP (rs4015735) could be a regulatory variant in expression of STEAP1 and optimal for investigations in case-control studies (see, e.g. Ge et al. 2005. Genome Res 15(11):1584-91). Genetic association studies between the STEAP1 polymorphism and high-functioning ASD might be worth doing.

SLC16A6 is a putative monocarboxylate transporter although the function has not been characterized. The expression of SLC16A6 was reduced by IL-13 in human monocyte (see, e.g. Scotton et al. 2005. J Immunol 174(2):834-45). Elevation of IL-13 levels was reported in children with ASD (see, e.g. Molloy et al. 2006. J Neuroimmunol 172(1-2):198-205). Interestingly, we identified IL-13 receptor $\alpha1$ (IL13RA1) as an up-regulated gene in idiopathic ASD, ASD with FMR1-FM, ASD with dup15q (Table 1). It is also important to note that SLC16A6 is located within regions that were identified as an autism locus by genetic analyses (see, e.g. Alarcon et al. 2005. Mol Psychiatry 10(8):747-57). These findings suggest that IL-13 signaling involving SLC16A6 might be dysregulated in ASD.

Genes Extremely Dysregulated in One of the 15 Affected Males

It has been shown that individuals with ASD carry chromosomal abnormality at a greater frequency than the general population (see, e.g. Christian et al. 2008. Biol Psychiatry 63(12):1111-7; Glessner et al. 2009. Nature; Jacquemont et al. 2006. J Med Genet 43(11):843-9; Marshall et al. 2008. Am J Hum Genet 82(2):477-88; Sebat et al. 2007. Science 316 (5823):445-9; Szatmari et al. 2007. Nat Genet 39(3):319-28; Veenstra-Vanderweele et al. 2004. Annu Rev Genomics Hum Genet 5:379-405; and Vorstman et al. 2006. Mol Psychiatry 11(1):1, 18-28). Many studies find rates of detected abnormalities in 5-10% of affected individuals (see, e.g. Veenstra-Vanderweele et al. 2004. Annu Rev Genomics Hum Genet 5:379-405; and Vorstman et al. 2006. Mol Psychiatry 11(1):1, 18-28). These abnormalities include unbalanced translocation, inversions, rings, and interstitial or terminal deletions and duplications (see, e.g. Vorstman et al. 2006. Mol Psychiatry 11(1):1, 18-28). The most frequent finding in ASD is dup15q (see, e.g. Szatmari et al. 2007. Nat Genet 39(3):319-28; Veenstra-Vanderweele et al. 2004. Annu Rev Genomics Hum Genet 5:379-405; and Vorstman et al. 2006. Mol Psychiatry 11(1):1, 18-28). Deletions of 2q37 and 22q13.3 have also been reported more than one occasion (see, e.g. Vorstman et al. 2006. Mol Psychiatry 11(1):1, 18-28). These chromosomal abnormalities can influence gene dosage and expression (see, e.g. Feuk et al. 2006. Hum Mol Genet 15 Spec No 1:R57-66). However, many chromosomal abnormalities are individually rare in the population with ASD. We hypothesized that genes whose expression levels were extremely different from the means of all individuals might be related to chromosomal abnormalities associated with ASD and that the differential expression might be detected in only one or a few affected males in the 15 male sib pairs. In this study, we identified 19 genes whose expression levels were extremely different in one of the 15 affected males. These genes included VIM, OMG, and GABRA4.

It has been reported that VIM is regulated by FMR1 (see, e.g. Miyashiro et al. 2003. Neuron 37(3):417-31; and Nishimura et al. 2007. Hum Mol Genet 16(14):1682-98) and TSC1/2 (see, e.g. Hengstschlager et al. 2004. Cancer Lett 210(2):219-26) that are causative genes for Fragile X syndrome and Tuberous sclerosis, respectively. Clinical phenotypes of these syndromes include ASD, suggesting VIM may be involved in the etiology of ASD. qPCR analysis confirmed the large reduction of VIM in one of the 15 affected male as expected in the microarray analysis. The mechanism of the 6-fold reduction of VIM is unknown. VIM has also been involved in CNVs that occurred in ASD (Sahoo et al. ASHG2006, #822). Interestingly, qPCR analysis also demonstrated that the expression of VIM was significantly different between the 39 male sib pairs discordant for idiopathic ASD.

Both OMG and GABRA4 have been reported to have significant association with ASD (see, e.g. Ma et al. 2005. Am J Hum Genet 77(3):377-88; and Martin et al. 2007b. Neurosci Res 59(4):426-30). An association between a subgroup of French patients with ASD and an allele of a non-synonymous SNP (rs11080149) in OMG were reported (see, e.g. Martin et al. 2007b. Neurosci Res 59(4):426-30). The SNP consisted in a G to A transition at position 62 from the start codon, changing a glycine to an aspartic acid. The amino acid change may modulate the precise localization or maturation of OMG (see, e.g. Martin et al. 2007b. Neurosci Res 59(4):426-30). The mechanism and meaning of the over-expression of OMG in ASD remain to be studied. rs1912960 in GABRA4 was also reported to have significant allelic and genotypic association with ASD (see, e.g. Ma et al. 2005. Am J Hum Genet 77(3): 377-88). Recently, an autism case with duplication of GABRA4 gene was reported (see, e.g. Kakinuma et al. 2007. Am J Med Genet B Neuropsychiatr Genet). Dysregulation of GABRA4 may be relevant to etiology of ASD.

Recently, Zhang et al surveyed expression profile of X-linked genes in lymphoblastoid cells from 43 males with X-linked mental retardation (XLMR) (see, e.g. Zhang et al. 2007. Genome Res 17(5):641-8). They identified 15 candidate genes including proteolipid protein 2 (PLP2). These genes were dysregulated only in one or two patients among the 47 males with XLMR. However, they identified a functional PLP2 promoter polymorphism enriched in patients with XLMR using large cohort (see, e.g. Zhang et al. 2007. Genome Res 17(5):641-8). These findings suggest that there might be regulatory polymorphisms in the 19 genes enriched in patients with ASD.

CNV may also be the cause of the dysregulation of these 19 genes identified in this study. It has been shown that CNV can alter mRNA expression (see, e.g. Durand et al. 2007. Nat Genet 39(1):25-7; Jeffries et al. 2005. Am J Med Genet A 137(2):139-47; Nishimura et al. 2007. Hum Mol Genet 16(14):1682-98; and Stranger et al. 2007. Science 315(5813): 848-53) and de novo CNV strongly associated with ASD (see, e.g. Sebat et al. 2007. Science 316(5823):445-9). Further study is needed to analyze CNV of the 19 genes in individuals identified in this study and in large cohort.

In conclusion, this study provides evidences that genome-wide expression profiling of lymphoblastoid cells is useful to identify susceptibility genes for ASD.

Tables

TABLE 1

Genes dysregulated in common among idiopathic ASD, ASD with FMR1-FM and ASD with dup15q

| Probe | Symbol | Gene Name | Gene Name | Locus | Idio/C | FM/C | Dup/C |
|---|---|---|---|---|---|---|---|
| A_24_P342591 | RERE | arginine-glutamic acid dipeptide (RE) repeats | arginine-glutamic acid dipeptide (RE) repeats | −0.06 | −0.16 | −0.14 | |
| A_23_P257365 | GFI1 | growth factor independent 1 | growth factor independent 1 | −0.12 | −0.17 | −0.22 | |
| A_32_P150300 | LOC100131646 | LOC100131646 | LOC100131646 | −0.06 | −0.16 | −0.16 | |
| A_24_P128163 | ADAMTS4 | ADAM metallopeptidase with thrombospondin type 1 motif, 4 | ADAM metallopeptidase with thrombospondin type 1 motif, 4 | −0.07 | −0.12 | −0.16 | |
| A_23_P114929 | BRP44 | brain protein 44 | brain protein 44 | −0.07 | −0.17 | −0.20 | |
| A_24_P234196 | RRM2 | ribonucleotide reductase M2 polypeptide | ribonucleotide reductase M2 polypeptide | −0.09 | −0.19 | −0.28 | |
| A_23_P120153 | RNF149 | ring finger protein 149 | ring finger protein 149 | −0.06 | −0.20 | −0.15 | |
| A_23_P209995 | IL1RN | interleukin 1 receptor antagonist | interleukin 1 receptor antagonist | 0.05 | 0.14 | 0.06 | |
| A_23_P360079 | NAP5 | Nck-associated protein 5 | Nck-associated protein 5 | −0.19 | −0.29 | −0.28 | |
| A_24_P484965 | LOC730124 | LOC730124 | LOC730124 | 0.04 | 0.09 | 0.07 | |
| A_24_P208452 | BBS5 | Bardet-Biedl syndrome 5 | Bardet-Biedl syndrome 5 | 0.07 | 0.19 | 0.21 | Buxbaum 2001 |
| A_23_P17130 | MGC13057 | | | −0.09 | −0.25 | −0.38 | |
| A_23_P131676 | CXCR7 | chemokine (C-X-C motif) receptor 7 | chemokine (C-X-C motif) receptor 7 | 0.16 | 0.43 | 0.66 | Sebat 2007 |
| A_23_P259362 | NPCDR1 | nasopharyngeal carcinoma, down-regulated 1 | nasopharyngeal carcinoma, down-regulated 1 | 0.02 | 0.06 | 0.06 | |
| A_23_P253250 | GCET2 | germinal center expressed transcript 2 | germinal center expressed transcript 2 | 0.13 | 0.61 | 0.51 | Allen-Brady 2008 |
| A_24_P182947 | GCET2 | germinal center expressed transcript 2 | germinal center expressed transcript 2 | 0.14 | 0.59 | 0.61 | Allen-Brady 2008 |
| A_23_P253317 | GPR171 | G protein-coupled receptor 171 | G protein-coupled receptor 171 | −0.13 | −0.24 | −0.35 | Alarcon 2005 |
| A_23_P351215 | SKIL | SKI-like | SKI-like | −0.10 | −0.24 | −0.15 | Alarcon 2005, Allen-Brady 2008 |
| A_23_P58036 | MCCC1 | methylcrotonoyl-Coenzyme A carboxylase 1 (alpha) | methylcrotonoyl-Coenzyme A carboxylase 1 (alpha) | 0.05 | 0.08 | 0.14 | Allen-Brady 2008 |

TABLE 1-continued

| Genes dysregulated in common among idiopathic ASD, ASD with FMR1-FM and ASD with dup15q | | | | | | | |
|---|---|---|---|---|---|---|---|
| Probe | Symbol | Gene Name | Gene Name | Locus | Idio/C | FM/C | Dup/C |
| A_23_P144274 | JAKMIP1 | janus kinase and microtubule interacting protein 1 | janus kinase and microtubule interacting protein 1 | 0.29 | 1.00 | 0.61 | |
| A_23_P18465 | RFC1 | replication factor C (activator 1) 1, 145 kDa | replication factor C (activator 1) 1, 145 kDa | −0.05 | −0.10 | −0.09 | |
| A_32_P165477 | SLC7A11 | solute carrier family 7 member 11 | solute carrier family 7 member 11 | −0.08 | −0.23 | −0.17 | Schellenberg 2006 |
| A_23_P121885 | ROPN1L | ropporin 1-like | ropporin 1-like | 0.07 | 0.12 | 0.10 | Marshall 2008 |
| A_32_P154342 | SLCO4C1 | solute carrier organic anion transporter family, member 4C1 | solute carrier organic anion transporter family, member 4C1 | −0.14 | −0.33 | −0.53 | |
| A_24_P409042 | CDC42SE2 | CDC42 small effector 2 | CDC42 small effector 2 | −0.07 | −0.13 | −0.09 | |
| A_23_P310972 | PCDHGB1 | protocadherin gamma subfamily B, 1 | protocadherin gamma subfamily B, 1 | 0.03 | 0.05 | 0.05 | |
| A_23_P7503 | TIMD4 | T-cell immunoglobulin and mucin domain containing 4 | T-cell immunoglobulin and mucin domain containing 4 | −0.29 | −0.53 | −0.57 | |
| A_32_P356316 | HLA-DOA | major histocompatibility complex, class II, DO alpha | major histocompatibility complex, class II, DO alpha | 0.10 | 0.28 | 0.25 | |
| A_24_P288836 | HLA-DPB2 | major histocompatibility complex, class II, DP beta 2 | major histocompatibility complex, class II, DP beta 2 | 0.09 | 0.24 | 0.21 | |
| A_23_P42353 | ETV7 | ets variant gene 7 | ets variant gene 7 | 0.10 | 0.26 | 0.39 | |
| A_24_P334640 | PAQR8 | progestin and adipoQ receptor family member VIII | progestin and adipoQ receptor family member VIII | 0.07 | 0.21 | 0.18 | |
| A_23_P255952 | MYO6 | myosin VI | myosin VI | −0.13 | −0.40 | −0.26 | |
| A_23_P350451 | PRDM1 | PR domain containing 1, with ZNF domain | PR domain containing 1, with ZNF domain | −0.15 | −0.34 | −0.17 | |
| A_23_P93442 | SASH1 | SAM and SH3 domain containing 1 | SAM and SH3 domain containing 1 | −0.17 | −0.62 | −0.73 | |
| A_24_P135841 | LRP11 | low density lipoprotein receptor-related protein 11 | low density lipoprotein receptor-related protein 11 | −0.13 | −0.36 | −0.30 | |
| A_23_P111593 | PSCD3 | pleckstrin homology, Sec7 and coiled-coil domains 3 | pleckstrin homology, Sec7 and coiled-coil domains 3 | 0.09 | 0.21 | 0.34 | |
| A_23_P252145 | C1GALT1 | core 1 synthase | core 1 synthase | −0.07 | −0.21 | −0.22 | |
| A_23_P31453 | STEAP1 | six transmembrane epithelial antigen of the prostate 1 | six transmembrane epithelial antigen of the prostate 1 | −0.26 | −0.73 | −0.46 | Barrett 1999 |
| A_24_P406334 | STEAP1 | six transmembrane epithelial antigen of the prostate 1 | six transmembrane epithelial antigen of the prostate 1 | −0.21 | −0.58 | −0.38 | Barrett 1999 |
| A_32_P69149 | STEAP1 | six transmembrane epithelial antigen of the prostate 1 | six transmembrane epithelial antigen of the prostate 1 | −0.24 | −0.65 | −0.46 | Barrett 1999 |
| A_23_P95130 | SLC37A3 | solute carrier family 37 member 3 | solute carrier family 37 member 3 | 0.08 | 0.17 | 0.12 | Alarcon 2002, Trikalinos 2005, Arkin 2008 |
| A_24_P274831 | GIMAP7 | GTPase, IMAP family member 7 | GTPase, IMAP family member 7 | 0.27 | 0.53 | 0.48 | Alarcon 2002, Trikalinos 2005, Arkin 2008 |
| A_23_P427023 | GIMAP1 | GTPase, IMAP family member 1 | GTPase, IMAP family member 1 | 0.20 | 0.42 | 0.43 | Alarcon 2002, Trikalinos |

TABLE 1-continued

| Genes dysregulated in common among idiopathic ASD, ASD with FMR1-FM and ASD with dup15q | | | | | | | |
|---|---|---|---|---|---|---|---|
| Probe | Symbol | Gene Name | Gene Name | Locus | Idio/C | FM/C | Dup/C |
| | | | | | | | 2005, Arkin 2008 |
| A_24_P92624 | GIMAP5 | GTPase, IMAP family member 5 | GTPase, IMAP family member 5 | 0.11 | 0.20 | 0.29 | Alarcon 2002, Trikalinos 2005, Arkin 2008 |
| A_23_P31810 | CEBPD | CCAAT/enhancer binding protein (C/EBP), delta | CCAAT/enhancer binding protein (C/EBP), delta | −0.17 | −0.38 | −0.39 | |
| A_23_P112135 | TRAM1 | translocation associated membrane protein 1 | translocation associated membrane protein 1 | −0.09 | −0.24 | −0.21 | |
| A_23_P146990 | WWP1 | WW domain containing E3 ubiquitin protein ligase 1 | WW domain containing E3 ubiquitin protein ligase 1 | −0.04 | −0.07 | −0.07 | |
| A_32_P176675 | FAM92A1 | family with sequence similarity 92, member A1 | family with sequence similarity 92, member A1 | 0.09 | 0.13 | 0.20 | |
| A_23_P168951 | ZHX2 | zinc fingers and homeoboxes 2 | zinc fingers and homeoboxes 2 | −0.08 | −0.15 | −0.10 | Yonan 2003 |
| A_23_P111978 | KCNK9 | potassium channel, subfamily K, member 9 | potassium channel, subfamily K, member 9 | −0.06 | −0.17 | −0.14 | |
| A_23_P94552 | TMEM2 | transmembrane protein 2 | transmembrane protein 2 | −0.20 | −0.59 | −0.56 | |
| A_24_P84419 | VAV2 | vav 2 oncogene | vav 2 oncogene | 0.04 | 0.08 | 0.09 | IMGSAC 2001, Auranen 2002 |
| A_23_P217120 | EHMT1 | euchromatic histone-lysine N-methyltransferase 1 | euchromatic histone-lysine N-methyltransferase 1 | −0.05 | −0.16 | −0.19 | IMGSAC 2001, Auranen 2002 |
| A_24_P374834 | OTUD1 | OTU domain containing 1 | OTU domain containing 1 | −0.13 | −0.23 | −0.30 | |
| A_32_P60459 | OTUD1 | OTU domain containing 1 | OTU domain containing 1 | −0.13 | −0.29 | −0.24 | |
| A_23_P52207 | BAMBI | BMP and activin membrane-bound inhibitor homolog | BMP and activin membrane-bound inhibitor homolog | −0.38 | −0.67 | −0.51 | |
| A_23_P86623 | ENTPD7 | ectonucleoside triphosphate diphosphohydrolase 7 | ectonucleoside triphosphate diphosphohydrolase 7 | −0.04 | −0.13 | −0.13 | |
| A_23_P158570 | ACADSB | acyl-Coenzyme A dehydrogenase, short/branched chain | acyl-Coenzyme A dehydrogenase, short/branched chain | 0.04 | 0.18 | 0.15 | |
| A_24_P189516 | ACADSB | acyl-Coenzyme A dehydrogenase, short/branched chain | acyl-Coenzyme A dehydrogenase, short/branched chain | 0.06 | 0.12 | 0.10 | |
| A_32_P215002 | CD44 | CD44 molecule | CD44 molecule | 0.09 | 0.11 | 0.19 | Trikalinos 2005, Szatmari 2007, Duvall 2007 |
| A_24_P13083 | TSPAN18 | tetraspanin 18 | tetraspanin 18 | 0.06 | 0.10 | 0.09 | Duvall 2007 |
| A_23_P2143 | SPCS2 | signal peptidase complex subunit 2 homolog | signal peptidase complex subunit 2 homolog | −0.06 | −0.14 | −0.09 | Duvall 2007 |
| A_23_P150768 | SLCO2B1 | solute carrier organic anion transporter family, member 2B1 | solute carrier organic anion transporter family, member 2B1 | −0.16 | −0.32 | −0.40 | Duvall 2007 |
| A_23_P1775 | DPAGT1 | dolichyl-phosphate N-acetylglucosamine-phosphotransferase 1 | dolichyl-phosphate N-acetylglucosamine phosphotransferase 1 | −0.03 | −0.06 | −0.08 | Duvall 2007 |
| A_24_P241183 | CLEC2D | C-type lectin domain family 2, member D | C-type lectin domain family 2, member D | −0.14 | −0.28 | −0.36 | |

TABLE 1-continued

Genes dysregulated in common among idiopathic ASD, ASD with FMR1-FM and ASD with dup15q

| Probe | Symbol | Gene Name | Gene Name | Locus | Idio/C | FM/C | Dup/C |
|---|---|---|---|---|---|---|---|
| A_24_P52921 | BCAT1 | branched chain aminotransferase 1, cytosolic | branched chain aminotransferase 1, cytosolic | 0.10 | 0.19 | 0.24 | |
| A_23_P306507 | KRAS | v-Ki-ras2 Kirsten rat sarcoma viral oncogene homolog | v-Ki-ras2 Kirsten rat sarcoma viral oncogene homolog | −0.13 | −0.22 | −0.20 | |
| A_32_P2452 | TMTC1 | transmembrane and tetratricopeptide repeat containing 1 | transmembrane and tetratricopeptide repeat containing 1 | −0.22 | −0.68 | −0.52 | |
| A_24_P98914 | PFKM | phosphofructokinase, muscle | phosphofructokinase, muscle | 0.03 | 0.10 | 0.08 | |
| A_24_P832426 | B3GALTL | beta 1,3-galactosyltransferase-like | beta 1,3-galactosyltransferase-like | −0.13 | −0.25 | −0.18 | Barrett 1999 |
| A_23_P428738 | ANG | angiogenin, ribonuclease, RNase A family, 5 | angiogenin, ribonuclease, RNase A family, 5 | −0.13 | −0.18 | −0.23 | |
| A_23_P151586 | TM9SF1 | transmembrane 9 superfamily member 1 | transmembrane 9 superfamily member 1 | −0.04 | −0.15 | −0.10 | |
| A_23_P65518 | DACT1 | dapper, antagonist of beta-catenin, homolog 1 | dapper, antagonist of beta-catenin, homolog 1 | −0.26 | −0.42 | −0.50 | |
| A_23_P348936 | CTAGE5 | CTAGE family, member 5 | CTAGE family, member 5 | −0.06 | −0.11 | −0.13 | |
| A_23_P88381 | NUMB | numb homolog | numb homolog | −0.07 | −0.12 | −0.10 | |
| A_23_P163306 | CGNL1 | cingulin-like 1 | cingulin-like 1 | −0.13 | −0.31 | −0.26 | |
| A_23_P65779 | STRA6 | stimulated by retinoic acid gene 6 homolog | stimulated by retinoic acid gene 6 homolog | 0.04 | 0.05 | 0.11 | Szatmari 2007, Marshall 2008 |
| A_23_P129128 | TARSL2 | threonyl-tRNA synthetase-like 2 | threonyl-tRNA synthetase-like 2 | −0.11 | −0.19 | −0.11 | |
| A_23_P129556 | IL4R | interleukin 4 receptor | interleukin 4 receptor | 0.10 | 0.19 | 0.20 | |
| A_24_P227927 | IL21R | interleukin 21 receptor | interleukin 21 receptor | 0.06 | 0.21 | 0.17 | |
| A_23_P206822 | XPO6 | exportin 6 | exportin 6 | 0.04 | 0.07 | 0.07 | |
| A_23_P3681 | NETO2 | neuropilin (NRP) and tolloid (TLL)-like 2 | neuropilin (NRP) and tolloid (TLL)-like 2 | −0.06 | −0.14 | −0.12 | |
| A_23_P14946 | MBTPS1 | membrane-bound transcription factor peptidase, site 1 | membrane-bound transcription factor peptidase, site 1 | −0.06 | −0.15 | −0.13 | |
| A_23_P14948 | MBTPS1 | membrane-bound transcription factor peptidase, site 1 | membrane-bound transcription factor peptidase, site 1 | −0.05 | −0.18 | −0.15 | |
| A_23_P4294 | ZNF232 | zinc finger protein 232 | zinc finger protein 232 | 0.05 | 0.14 | 0.08 | Duvall 2007 |
| A_24_P188218 | MYL4 | myosin, light chain 4, alkali; atrial, embryonic | myosin, light chain 4, alkali; atrial, embryonic | −0.13 | −0.26 | −0.23 | Cantor 2005, Duvall 2007 |
| A_23_P89455 | SLC35B1 | solute carrier family 35, member B1 | solute carrier family 35, member B1 | −0.04 | −0.10 | −0.10 | Cantor 2005, Duvall 2007 |
| A_32_P217346 | APPBP2 | amyloid beta precursor protein binding protein 2 | amyloid beta precursor protein binding protein 2 | 0.04 | 0.05 | 0.15 | Alarcon 2005, Cantor 2005, Duvall 2007 |
| A_23_P152791 | SLC16A6 | solute carrier family 16, member 6 | solute carrier family 16, member 6 | −0.06 | −0.22 | −0.26 | Alarcon 2005 |
| A_24_P731648 | SLC16A6 | solute carrier family 16, member 6 | solute carrier family 16, member 6 | −0.07 | −0.24 | −0.23 | Alarcon 2005 |
| A_23_P412577 | ANKRD29 | ankyrin repeat domain 29 | ankyrin repeat domain 29 | −0.12 | −0.25 | −0.32 | |
| A_23_P66948 | FAM59A | family with sequence similarity 59, member A | family with sequence similarity 59, member A | −0.20 | −0.49 | −0.43 | |
| A_23_P433063 | ATCAY | ataxia, cerebellar, Cayman type | ataxia, cerebellar, Cayman type | 0.03 | 0.05 | 0.06 | Schellenberg 2006 |

TABLE 1-continued

| Genes dysregulated in common among idiopathic ASD, ASD with FMR1-FM and ASD with dup15q | | | | | | | |
|---|---|---|---|---|---|---|---|
| Probe | Symbol | Gene Name | Gene Name | Locus | Idio/C | FM/C | Dup/C |
| A_23_P50426 | KANK2 | KN motif and ankyrin repeat domains 2 | KN motif and ankyrin repeat domains 2 | −0.09 | −0.23 | −0.21 | Liu 2001 |
| A_24_P93887 | MED29 | mediator complex subunit 29 | mediator complex subunit 29 | 0.03 | 0.09 | 0.07 | Liu 2001 |
| A_23_P166100 | TXNDC13 | thioredoxin domain containing 13 | thioredoxin domain containing 13 | −0.09 | −0.21 | −0.22 | |
| A_23_P17316 | NKAIN4 | Na+/K+ transporting ATPase interacting 4 | Na+/K+ transporting ATPase interacting 4 | 0.05 | 0.05 | 0.11 | Marshall 2008 |
| A_24_P339869 | ZNF295 | zinc finger protein 295 | zinc finger protein 295 | 0.05 | 0.11 | 0.09 | |
| A_24_P267686 | LOC729314 | LOC729314 | LOC729314 | 0.04 | 0.05 | 0.10 | |
| A_24_P387514 | LRP5L | low density lipoprotein receptor-related protein 5-like | low density lipoprotein receptor-related protein 5-like | 0.05 | 0.16 | 0.08 | |
| A_24_P945283 | DLG3 | discs, large homolog 3 | discs, large homolog 3 | −0.16 | −0.30 | −0.47 | |
| A_23_P137196 | IL13RA1 | interleukin 13 receptor, alpha 1 | interleukin 13 receptor, alpha 1 | 0.11 | 0.20 | 0.26 | |
| A_24_P280113 | IL13RA1 | interleukin 13 receptor, alpha 1 | interleukin 13 receptor, alpha 1 | 0.29 | 0.51 | 0.61 | |
| A_23_P213085 | unknown | | | −0.07 | −0.16 | −0.18 | |
| A_24_P152775 | unknown | | | 0.03 | 0.05 | 0.10 | |
| A_24_P221285 | unknown | | | −0.09 | −0.19 | −0.30 | |
| A_24_P238118 | unknown | | | 0.03 | 0.07 | 0.08 | |
| A_24_P384979 | unknown | | | 0.05 | 0.10 | 0.17 | |
| A_24_P479510 | unknown | | | −0.13 | −0.21 | −0.26 | |
| A_24_P493100 | unknown | | | −0.04 | −0.11 | −0.15 | |
| A_24_P521662 | unknown | | | 0.04 | 0.09 | 0.11 | |
| A_24_P63397 | unknown | | | 0.03 | 0.13 | 0.10 | |
| A_24_P68079 | unknown | | | −0.09 | −0.27 | −0.18 | |
| A_24_P925310 | unknown | | | 0.05 | 0.07 | 0.11 | |
| A_32_P102383 | unknown | | | 0.04 | 0.07 | 0.21 | |
| A_32_P103815 | unknown | | | −0.09 | −0.15 | −0.18 | |
| A_32_P137826 | unknown | | | −0.20 | −0.32 | −0.45 | |
| A_32_P163894 | unknown | | | 0.05 | 0.15 | 0.21 | |
| A_32_P232682 | unknown | | | −0.10 | −0.16 | −0.17 | |
| A_32_P34696 | unknown | | | 0.06 | 0.12 | 0.11 | |
| A_32_P45309 | unknown | | | 0.04 | 0.14 | 0.13 | |
| A_32_P69333 | unknown | | | −0.12 | −0.39 | −0.27 | |
| A_32_P72758 | unknown | | | −0.14 | −0.42 | −0.58 | |
| A_32_P9924 | unknown | | | 0.04 | 0.09 | 0.06 | |

[a]idio/CNT was $\log_2$ (mean value of control (N = 15)/mean value of idiopathic ASD (N = 15)).
[b]FM/CNT was $\log_2$ (mean value of ASD with FMR1FM (N = 6)/mean value of idiopathic ASD (N = 15)).
[c]dup/CNT was $\log_2$ (mean value of ASD with dup15q (N = 7)/mean value of idiopathic ASD (N = 15)).
[d]Autism loci identified by other genetic studies were shown with references.

TABLE 2

| Genes extremely dysregulated in one of the 15 affected males | | | | | | |
|---|---|---|---|---|---|---|
| Probe | Symbol | Gene Name | Locus | Change | Individual | Reference |
| A_23_P149529 | TACSTD2 | tumor-associated calcium signal transducer 2 | 1p32-p31 | 2.1 | AU1038302 | |
| A_24_P222147 | C1orf131 | chromosome 1 open reading frame 131 | 1q42.2 | 1.0 | AU055105 | |
| A_24_P169234 | ZAP70 | zeta-chain associated protein kinase 70 kDa | 2q12 | 1.2 | AU055105 | |
| A_23_P79518 | IL1B | interleukin 1, beta | 2q14 | 2.4 | AU0943301 | |
| A_32_P204137 | GABRA4 | GABA A receptor, alpha 4 | 4p12 | 2.2 | AU016803 | Kakinuma 2008 |
| A_23_P122443 | HIST1H1C | histone 1, H1c | 6p21.3 | −2.4 | AU0943301 | |
| A_24_P280628 | VPS13B | vacuolar protein sorting 13B | 8q22.2 | −1.1 | AU1215304 | |
| A_23_P258312 | NAPRT1 | nicotinate phosphoribosyltransferase domain containing 1 | 8q24.3 | −3.1 | AU0943301 | Weidmer-Mikhail 1998 |
| A_32_P395992 | DEC1 | deleted in esophageal cancer 1 | 9q32 | 2.3 | AU0943301 | |
| A_23_P161190 | VIM | vimentin | 10p13 | −2.6 | AU0943301 | Sahoo |

TABLE 2-continued

| Genes extremely dysregulated in one of the 15 affected males | | | | | | |
|---|---|---|---|---|---|---|
| Probe | Symbol | Gene Name | Locus | Change | Individual | Reference |
| | | | | | | et. al ASHG 2006 |
| A_23_P161194 | VIM | vimentin | 10p13 | −2.6 | AU0943301 | Newman et al ASHG 2006 |
| A_23_P151046 | KLRC1 | killer cell lectin-like receptor subfamily C, member 1 | 12p13 | 2.1 | AU081205 | |
| A_24_P409126 | FNDC3A | fibronectin type III domain containing 3A | 13q14.2 | 1.8 | AU055105 | |
| A_23_P48530 | INSM2 | insulinoma-associated 2 | 14q13.2 | 1.0 | AU055105 | |
| A_23_P65629 | KCNK10 | potassium channel, subfamily K, member 10 | 14q31 | 0.8 | AU055105 | |
| A_23_P55286 | OMG | oligodendrocyte myelin glycoprotein | 17q11.2 | 2.0 | AU016803 | |
| A_23_P119353 | RASIP1 | Ras interacting protein 1 | 19q13.33 | 3.9 | AU1165302 | |
| A_23_P21120 | MED14 | mediator complex subunit 14 | Xp11.4-p11.2 | 1.1 | AU016803 | |
| A_23_P432352 | CXorf61 | chromosome X open reading frame 61 | Xq23 | 1.7 | AU016803 | |
| A_23_P73677 | RHOXF2 | Rhox homeobox family, member 2 | Xq24 | 1.4 | AU1157301 | |
| A_23_P352494 | RHOXF2 | Rhox homeobox family, member 2 | Xq24 | 1.4 | AU1157301 | |

[a]Change was the value of $\log_2$ (intensity of the proband/mean value of the 15 male sib pairs).

REFERENCES CITED IN TABLES 1 AND 2

Alarcon et al. 2002. Am J Hum Genet 70(1):60-71 Epub 2001 Dec. 6.

Alarcon et al. 2005. Mol Psychiatry 10(8):747-57.

Allen-Brady et al. Feb. 19, 2008. Mol Psychiatry.

Auranen et al. 2002. Am J Hum Genet 71(4):777-90 Epub 2002 Aug. 21.

Barrett et al. 1999. Am J Med Genet 88(6):609-15.

Buxbaum et al. 2001. Am J Hum Genet 68(6):1514-20.

Cantor et al. 2005. Am J Hum Genet 76(6):1050-6.

Duvall et al. 2007. Am J Psychiatry 164(4):656-62.

Kakinuma et al. 2007. Am J Med Genet B Neuropsychiatr Genet.

Liu et al. 2001. Am J Hum Genet 69(2):327-40 Epub 2001 Jul. 10.

Marshall et al. 2008. Am J Hum Genet 82(2):477-88.

Schellenberg et al. 2006. Mol Psychiatry 11(11):1049-60, 979.

Sebat et al. 2007. Science 316(5823):445-9.

Szatmari et al. 2007. Nat Genet 39(3):319-28.

Trikalinos et al. 2006. Mol Psychiatry 11(1):29-36.

Weidmer-Mikhail et al. 1998. J Intellect Disabil Res 42 (Pt 1):8-12.

Yonan et al. 2003. Am J Hum Genet 73(4):886-97 Epub 2003 Sep. 17.

TABLE 3

| Individuals analyzed in this study | | | | | | |
|---|---|---|---|---|---|---|
| Individual Code | family ID | group | ADIR | ADOS | Raven IQ | analysis |
| AU016703 | AU0167 | CNT | | | | microarray, qPCR |
| AU016704 | AU0167 | idiopathic ASD | BroadSpectrum | Spectrum | 100 | microarray, qPCR |
| AU016803 | AU0168 | idiopathic ASD | Autism | Autism | 94 | microarray, qPCR |
| AU016804 | AU0168 | CNT | | | | microarray, qPCR |
| AU055103 | AU0551 | CNT | | | | microarray, qPCR |
| AU055105 | AU0551 | idiopathic ASD | NQA | Spectrum | 108 | microarray, qPCR |
| AU060003 | AU0600 | CNT | | | | microarray, qPCR |
| AU060004 | AU0600 | idiopathic ASD | Autism | | 100 | microarray, qPCR |
| AU081205 | AU0812 | idiopathic ASD | Autism | not Spectrum or Autism | 128 | microarray, qPCR |
| AU081206 | AU0812 | CNT | | | | microarray, qPCR |
| AU0943301 | AU0943 | idiopathic ASD | Autism | Spectrum | 110 | microarray, qPCR |

TABLE 3-continued

Individuals analyzed in this study

| Individual Code | family ID | group | ADIR | ADOS | Raven IQ | analysis |
|---|---|---|---|---|---|---|
| AU0943303 | AU0943 | CNT | | | | microarray, qPCR |
| AU0995302 | AU0995 | CNT | | | | microarray, qPCR |
| AU0995303 | AU0995 | idiopathic ASD | Autism | Spectrum | 105 | microarray, qPCR |
| AU1038302 | AU1038 | idiopathic ASD | Autism | Spectrum | 95 | microarray, qPCR |
| AU1038304 | AU1038 | CNT | | | | microarray, qPCR |
| AU1086301 | AU1086 | CNT | | | | microarray, qPCR |
| AU1086303 | AU1086 | idiopathic ASD | Autism | Autism | 110 | microarray, qPCR |
| AU1157301 | AU1157 | idiopathic ASD | Autism | Autism | 119 | microarray, qPCR |
| AU1157302 | AU1157 | CNT | | | | microarray, qPCR |
| AU1165302 | AU1165 | idiopathic ASD | Autism | Autism | 110 | microarray, qPCR |
| AU1165303 | AU1165 | CNT | | | | microarray, qPCR |
| AU1165304 | AU1165 | idiopathic ASD | Autism | Autism | 114 | microarray, qPCR |
| AU1165305 | AU1165 | CNT | | | | microarray, qPCR |
| AU1215303 | AU1215 | CNT | | | | microarray, qPCR |
| AU1215304 | AU1215 | idiopathic ASD | Autism | Spectrum | 119 | microarray, qPCR |
| AU1327302 | AU1327 | idiopathic ASD | Autism | Autism | 104 | microarray, qPCR |
| AU1327303 | AU1327 | CNT | | | | microarray, qPCR |
| AU1348302 | AU1348 | CNT | | | | microarray, qPCR |
| AU1348303 | AU1348 | idiopathic ASD | Autism | Autism | 107 | microarray, qPCR |
| AU0081302 | AU0081 | CNT | | | | qPCR |
| AU0081303 | AU0081 | idiopathic ASD | Autism | Autism | 85 | qPCR |
| AU008403 | AU0084 | idiopathic ASD | Autism | Autism | 94 | qPCR |
| AU008405 | AU0084 | CNT | | | | qPCR |
| AU016804 | AU0168 | CNT | | | | qPCR |
| AU016805 | AU0168 | idiopathic ASD | Autism | Autism | 100 | qPCR |
| AU028904 | AU0289 | CNT | | | | qPCR |
| AU028905 | AU0289 | idiopathic ASD | Autism | Autism | 110 | qPCR |
| AU065603 | AU0656 | CNT | | | | qPCR |
| AU065604 | AU0656 | idiopathic ASD | Autism | Autism | 94 | qPCR |
| AU0901301 | AU0901 | CNT | | | | qPCR |
| AU0901302 | AU0901 | idiopathic ASD | Autism | Autism | 125 | qPCR |
| AU1007301 | AU1007 | CNT | | | | qPCR |
| AU1007302 | AU1007 | idiopathic ASD | Autism | Autism | 119 | qPCR |
| AU1054301 | AU1054 | idiopathic ASD | Autism | Autism | 90 | qPCR |
| AU1054303 | AU1054 | CNT | | | | qPCR |
| AU1056301 | AU1056 | idiopathic ASD | Autism | Autism | 100 | qPCR |
| AU1056303 | AU1056 | CNT | | | | qPCR |
| AU1073301 | AU1073 | idiopathic ASD | Autism | Autism | 103 | qPCR |
| AU1073303 | AU1073 | CNT | | | | qPCR |
| AU1193301 | AU1193 | CNT | | | | qPCR |
| AU1193302 | AU1193 | idiopathic ASD | Autism | Autism | 100 | qPCR |
| AU1234301 | AU1234 | CNT | | | | qPCR |
| AU1234302 | AU1234 | idiopathic ASD | Autism | Autism | 93 | qPCR |
| AU1325301 | AU1325 | idiopathic ASD | Autism | Autism | 100 | qPCR |

TABLE 3-continued

| Individuals analyzed in this study | | | | | | |
|---|---|---|---|---|---|---|
| Individual Code | family ID | group | ADIR | ADOS | Raven IQ | analysis |
| AU1325302 | AU1325 | CNT | | | | qPCR |
| AU1327303 | AU1327 | CNT | | | | qPCR |
| AU1327304 | AU1327 | idiopathic ASD | Autism | Autism | 114 | qPCR |
| AU1338303 | AU1338 | CNT | | | | qPCR |
| AU1338304 | AU1338 | idiopathic ASD | Autism | Autism | 110 | qPCR |
| AU1344302 | AU1344 | Idiopathic ASD | Autism | Autism | 128 | qPCR |
| AU1344303 | AU1344 | CNT | | | | qPCR |
| AU1346302 | AU1346 | idiopathic ASD | Autism | Autism | 125 | qPCR |
| AU1346304 | AU1346 | CNT | | | | qPCR |
| AU1412301 | AU1412 | idiopathic ASD | Autism | Autism | 131 | qPCR |
| AU1412302 | AU1412 | CNT | | | | qPCR |
| AU1424303 | AU1424 | CNT | | | | qPCR |
| AU1424304 | AU1424 | idiopathic ASD | Autism | Autism | 103 | qPCR |
| AU1466301 | AU1466 | CNT | | | | qPCR |
| AU1466302 | AU1466 | idiopathic ASD | Autism | Autism | 94 | qPCR |
| AU1549303 | AU1549 | idiopathic ASD | Autism | Autism | 125 | qPCR |
| AU1549304 | AU1549 | CNT | | | | qPCR |
| AU1562301 | AU1562 | CNT | | | | qPCR |
| AU1562303 | AU1562 | idiopathic ASD | Autism | Autism | 122 | qPCR |
| AU1601302 | AU1601 | idiopathic ASD | Autism | Autism | 114 | qPCR |
| AU1601303 | AU1601 | CNT | | | | qPCR |
| AU1610304 | AU1610 | CNT | | | | qPCR |
| AU1610306 | AU1610 | idiopathic ASD | Autism | Autism | 90 | qPCR |
| AU039304 | AU0393 | ASD with FMR1FM | Autism | | | microarray |
| AU039305 | AU0393 | ASD with FMR1FM | Autism | | | microarray |
| AU046703 | AU0467 | ASD with FMR1FM | Autism | | | microarray |
| AU046706 | AU0467 | ASD with FMR1FM | Autism | | | microarray |
| AU066703 | AU0667 | ASD with FMR1FM | Autism | | | microarray |
| AU066704 | AU0667 | ASD with FMR1FM | Autism | | | microarray |
| 01-19- | | ASD with dup15q | not Autism | Autism | | microarray |
| 03-43- | | ASD with dup15q | Autism | Autism | | microarray |
| 02-7- | | ASD with dup15q | Autism | Autism | | microarray |
| 98-19- | | ASD with dup15q | Autism | | | microarray |
| AU006504 | AU0065 | ASD with dup15q | Autism | | | microarray |
| AU010603 | AU0106 | ASD with dup15q | Autism | Spectrum | | microarray |
| AU010604 | AU0106 | ASD with dup15q | Autism | Autism | | microarray |

TABLE 4

| Gene networks identified by IPA using the 92 genes dysregulated in ASD | |
|---|---|
| Genes in network | Top functions |
| Actin, ADAMTS4, ALOX5AP, ANG, CLEC2D, CTSS, CXCL11, dihydrotestosterone, ETV7, GLUL, GUSB, HLA-DOA, HLA-DQB1, HLX, IFNG, IL13, IL13RA1, IL13RA2, IL4R, PTEN, RARA, RNF111, SKIL, SLC16A6, | Cellular Development Inflammatory Disease Hematological |

TABLE 4-continued

| Gene networks identified by IPA using the 92 genes dysregulated in ASD | |
|---|---|
| Genes in network | Top functions |
| SMURF2, STRA6, TGFB1, TGFBR1, | System Development and Function |
| TIMD4, TPM3, TRAM1, TYK2, UBE2D1, WWP1, XPO6 | |

TABLE 4-continued

| Gene networks identified by IPA using the 92 genes dysregulated in ASD | |
|---|---|
| Genes in network | Top functions |
| ANKRD29, ASNS, AZU1, BAMBI, BCAT1, BRP44, CD70, DUSP5, DUSP16, EGF, | Cancer, |
| FSTL1, GAS1, GFI1, GFI1B, GZMK, IL15, IL21R, MYC, MYL4, MYO6, NR3C1, | Cell Death, |
| PFKM, PLAGL1, PRDM1, RERE, RRM2, RRM2B, SASH1, SOD2, STAT5B, TCF3, TERT, TP53, TYK2, ZFP36L1 | Cell Cycle |
| ABCC5, AKR1C14, ALOX5AP, beta-estradiol, CCDC80, CCDC92, CEBPD, CLEC11A, | Cell Cycle, |
| CXADR, CXCL11, CXCR7, DBN1, DLG3, DUSP5, FLII, GCET2, GDA, IHPK2, IL1RN, KRAS, MBTPS1, MED18, MED20, MED29, MMD, NBL1, NFkB, PCOLCE, PDGF BB, | Cellular Development, Hematological System Development and Function |
| PRDX4, PSCD3, SLC35B1, SPCS2, TLR9, VAV2 | |
| ACADSB, AGT, ANKRD25, CDC42, CDC25C, CDH3, CDKN2A, CLU, DPAGT1, EHMT1, | Cell Cycle, |
| ENTPD7, ERBB2, ERRFI1, GIMAP1, GTP, Histone h3, HRAS, hydrogen peroxide, | Cancer, |
| ITSN2, JAK1, JAKMIP1, LRP11, MCCC1, NUMB, phosphate, RALBP1, RALGDS, RASGRF2, RASSF5, RFC1, RIN1, SLC7A11, SUZ12, TYK2, ZHX2 | Cell Morphology |

TABLE 5

ILLUSTRATIVE HUMAN DASD POLYNUCLEOTIDE SEQUENCES RETREIVED FROM GENBANK LIBRARY DATABASE USING THE DISCLOSURE IN TABLES 1-4

JAKMIP (SEQ ID NO: 7)

GGGGGCTGCGCTCGCTACGTCCGCTGCTGCTGCCCGGCTCGGGCCTGAGC
GCCGAGCAGGATCCCAAGTGATGGTGGTTTCCTCGGAGGGCGAGCTGAGT
ACTGCGCGACTGGTTAGCACGGTGGAGCTGGTAGCCACGCCTGCTGGCTG
GCGTGCGTGAACAGGTGTGGACCGCAGGATCTCAGCACTCTGACCCAAGG
GGAAGCATGTCGAAGAAAGGCCGGAGCAAGGGCGAGAAGCCCGAGATGGA
GACGGACGCGGTGCAGATGGCCAACGAGGAGCTGCGGGCCAAGCTGACCA
GCATTCAGATCGAGTTCCAGCAGGAAAAAAGCAAGGTGGGCAAACTGCGC
GAGCGGCTGCAGGAGGCGAAGCTGGAGCGCGAGCAGGAGCAGCGACGGCA
CACGGCCTACATTTCGGAGCTCAAGGCCAAGCTGCATGAGGAGAAGACCA
AGGAGCTGCAGGCGCTGCGCGAGGGGCTCATCCGGCAGCACGAGCAGGAG
GCGGCGCGCACCGCCAAGATCAAGGAGGGCGAGCTGCAGCGGCTACAGGC
CACGCTGAACGTGCTGCGCGACGGCGCGGCCGACAAGGTCAAGACGGCGC
TGCTGACCGAGGCGCGCGAGGAGGCGCGCAGGGCCTTCGATGGAGAGCGC
CTGCGGCTGCAGCAGGAGATCCTGGAGCTCAAGGCAGCGCGCAATCAGGC
AGAGGAGGCGCTCAGTAACTGCATGCAGGCCGACAAGACCAAGGCAGCCG
ACCTGCGTGCCGCCTACCAGGCGCACCAAGACGAGGTGCACCGCATCAAG
CGCGAGTGCGAGCGCGACATCCGCAGGCTGATGGATGAGATCAAAGGGAA
AGACCGTGTGATTCTGGCCTTGGAGAAGGAACTTGGCGTGCAGGCTGGGC
AGACCCAGAAGCTGCTTCTGCAGAAAGAGGCTTTGGATGAGCAGCTGGTT
CAGGTCAAGGAGGCCGAGCGGCACCACAGTAGTCCAAAGAGAGAGCTCCC
GCCCGGGATCGGGGACATGGTGGAGCTCATGGGCGTCCAGGATCAACATA
TGGACGAGCGAGATGTGAGGCGATTTCAACTAAAAATTGCTGAACTGAAT
TCAGTGATACGGAAGCTGGAAGACAGAAATACGCTGTTGGCAGATGAGAG
GAATGAACTGCTGAAACGCTCACGAGAGACCGAGGTTCAGCTGAAGCCCC
TGGTGGAGAAGAACAAGCGGATGAACAAGAAGAATGAGGATCTGTTGCAG
AGTATCCAGAGGATGGAGGAGAAAATCAAGAACCTCACGCGGGAAAACGT
GGAAATGAAAGAAAAGCTGTCAGCGCAGGCGTCTCTGAAGCGGCATACCT
CCTTGAATGACCTCAGCCTGACGAGGGATGAGCAGGAGATCGAGTTCCTG
AGGCTGCAGGTGCTGGAGCAGCAGCACGTCATTGACGACCTCTCACTGGA
GAGAGAACGGCTGTTGCGCTCCAAAAGGCATCGAGGGAAAAGTCTGAAAC
CGCCCAAGAAGCATGTTGTGGAGACATTTTTTGGATTTGATGAGGAGTCT
GTGGACTCAGAAACGTTGTCCGAAACATCCTACAACACAGACAGGACAGA
CAGGACCCCAGCCACGCCCGAAGAAGACTTGGACGATGCCACAGCCCGAG
AGGAGGCTGACCTGCGCTTCTGCCAGCTGACCCGGGAGTACCAGGCCCTG
CAACGCGCCTACGCCCTGCTCCAGGAGCAGGTGGGAGGCACGCTGGACGC
TGAGAGGGAGGCCCGGACTCGGGAGCAGCTACAAGCTGATCTGCTGAGGT
GTCAGGCCAAAATCGAAGATTTGGAGAAGTTACTGGTTGAGAAGGGACAG
GATTCCAAGTGGGTTGAAGAGAAGCAGCTGCTCATCAGAACAAACCAAGA
CTTGCTGGAAAAGATTTACAGACTGGAAATGGAAGAGAACCAGCTGAAGA

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

ATGAAATGCAAGACGCCAAGGATCAGAACGAGCTGTTAGAATTCAGAGTG
CTAGAACTCGAAGTAAGAGACTCTATCTGTTGTAAACTCTCAAACGGAGC
AGACATTCTCTTTGAACCCAAACTGAAATTCATGTAAAGCTCTCAGATGT
TTTCAAGCATGTGTAAAGGGGACATGTTATAGTTTCTTTCTTTCTTTCTT
TCTTTTTTTTTTTAAATCTGTATGTTCAGAATAATTTCACTGCCTTAATG
TGTTCTGGAGAGCGTGCTCACCCAAGTCTATGGACATGTACCAGAGCTAA
TATATTTATTGCCTATGGCTTGTTTTGCACTTAATAAAATAATTTGTTTT
TACAAAAAAA

STEAP (SEQ ID NO: 8)

GCGGACGCGGGGCGCCAGCAGGTGGCGCTGGACGCGCAACGGACAAGGAG
GCGGGGCCTGCAGCTGGCTTGGAGGCTCCGCGCTCTGGAGGCTCAGGCGC
CGCGTGGGGCCCGCACCTCTGGGCAGCAGCGGCAGCCGAGACTCACGGTC
AAGCTAAGGCGAAGAGTGGGTGGCTGAAGCCATACTATTTTATAGAATTA
ATGGAAAGCAGAAAAGACATCACAAACCAAGAAGAACTTTGGAAAATGAA
GCCTAGGAGAAATTTAGAAGAAGACGATTATTTGCATAAGGACACGGGAG
AGACCAGCATGCTAAAAAGACCTGTGCTTTTGCATTTGCACCAAACAGCC
CATGCTGATGAATTTGACTGCCCTTCAGAACTTCAGCACACACAGGAACT
CTTTCCACAGTGGCACTTGCCAATTAAAATAGCTGCTATTATAGCATCTC
TGACTTTTCTTTACACTCTTCTGAGGGAAGTAATTCACCCTTTAGCAACT
TCCCATCAACAATATTTTTATAAAATTCCAATCCTGGTCATCAACAAAGT
CTTGCCAATGGTTTCCATCACTCTCTTGGCATTGGTTTACCTGCCAGGTG
TGATAGCAGCAATTGTCCAACTTCATAATGGAACCAAGTATAAGAAGTTT
CCACATTGGTTGGATAAGTGGATGTTAACAAGAAAGCAGTTTGGGCTTCT
CAGTTTCTTTTTTGCTGTACTGCATGCAATTTATAGTCTGTCTTACCCAA
TGAGGCGATCCTACAGATACAAGTTGCTAAACTGGGCATATCAACAGGTC
CAACAAAATAAAGAAGATGCCTGGATTGAGCATGATGTTTGGAGAATGGA
GATTTATGTGTCTCTGGGAATTGTGGGATTGGCAATACTGGCTCTGTTGG
CTGTGACATCTATTCCATCTGTGAGTGACTCTTTGACATGGAGAGAATTT
CACTATATTCAGAGCAAGCTAGGAATTGTTTCCCTTCTACTGGGCACAAT
ACACGCATTGATTTTTGCCTGGAATAAGTGGATAGATATAAAACAATTTG
TATGGTATACACCTCCAACTTTTATGATAGCTGTTTTCCTTCCAATTGTT
GTCCTGATATTTAAAAGCATACTATTCCTGCCATGCTTGAGGAAGAAGAT
ACTGAAGATTAGACATGGTTGGGAAGACGTCACCAAAATTAACAAAACTG
AGATATGTTCCCAGTTGTAGAATTACTGTTTACACACATTTTTGTTCAAT
ATTGATATATTTTATCACCAACATTTCAAGTTTGTATTTGTTAATAAAAT
GATTATTCAAGGAAAAAAAA

NAPRT (SEQ ID NO: 9)

GCGGAGTCCGGACGTCGGGAGCAGGATGGCGGCGGAGCAGGACCCCGAGG
CGCGCGCGGCGGCGCGGCCGCTGCTCACTGACCTCTACCAGGCCACCATG
GCGTTGGGCTATTGGCGCGGGCCGGGCGCGGGACGCCGCCGAGTTCGA
GCTCTTCTTCCGCCGCTGCCCGTTCGGCGGCGCCTTCGCCTTGGCCGCCG
GCTTGCGCGACTGTGTGCGCTTCCTGCGCGCCTTCCGCCTGCGGGACGCC
GACGTGCAGTTCCTGGCCTCGGTGCTGCCCCCAGACACGGATCCTGCGTT
CTTCGAGCACCTTCGGGCCCTCGACTGCTCCGAGGTGACGGTGCGAGCCC
TGCCCGAGGGCTCCCTCGCCTTCCCCGGAGTGCCGCTCCTGCAGGTGTCC
GGGCCGCTCCTGGTGGTGCAGCTGCTGGAGACACCGCTGCTCTGCCTGGT
CAGCTACGCCAGCCTGGTGGCCACCAACGCAGCGCGGCTTCGCTTGATCG
CAGGGCCAGAGAAGCGGCTGCTAGAGATGGGCCTGAGGCGGGCTCAGGGC
CCCGATGGGGGCCTGACAGCCTCCACCTACAGCTACCTGGGCGGCTTCGA
CAGCAGCAGCAACGTGCTAGCGGGCCAGCTGCGAGGTGTGCCGGTGGCCG
GGACCCTGGCCCACTCCTTCGTCACTTCCTTTTCAGGCAGCGAGGTGCCC
CCTGACCCGATGTTGGCGCCAGCAGCTGGTGAGGGCCCTGGGGTGGACCT
GGCGGCCAAAGCCCAGGTGTGGCTGGAGCAGGTGTGTGCCCACCTGGGGC
TGGGGGTGCAGGAGCCGCATCCAGGCGAGCGGGCAGCCTTTGTGGCCTAT
GCCTTGGCTTTTCCCCGGGCCTTCCAGGGCCTCCTGGACACCTACAGCGT
GTGGAGGAGTGGTCTCCCCAACTTCCTAGCAGTCGCCCTGGCCCTGGGAG
AGCTGGGCTACCGGGCAGTGGGCGTGAGGCTGGACAGTGGTGACCTGCTA
CAGCAGGCTCAGGAGATCCGCAAGGTCTTCCGAGCTGCTGCAGCCCAGTT
CCAGGTGCCCTGGCTGGAGTCAGTCCTCATCGTAGTCAGCAACAACATTG
ACGAGGAGGCGCTGGCCCGACTGGCCCAGGAGGGCAGTGAGGTGAATGTC
ATTGGCATTGGCACCAGTGTGGTCACCTGCCCCCAACAGCCTTCCCTGGG
TGGCGTCTATAAGCTGGTGGCCGTGGGGGGCCAGCCACGAATGAAGCTGA
CCGAGGACCCCGAGAAGCAGACGTTGCCTGGGAGCAAGGCTGCTTTCCGG
CTCCTGGGCTCTGACGGGTCTCCACTCATGGACATGCTGCAGTTAGCAGA
AGAGCCAGTGCCACAGGCTGGGCAGGAGCTGAGGGTGTGGCCTCCAGGGG
CCCAGGAGCCCTGCACCGTGAGGCCAGCCCAGGTGGAGCCACTACTGCGG
CTCTGCCTCCAGCAGGGACAGCTGTGTGAGCCGCTCCCATCCCTGGCAGA
GTCTAGAGCCTTGGCCCAGCTGTCCCTGAGCCGACTCAGCCCTGAGCACA
GGCGGCTGCGGAGCCCTGCACAGTACCAGGTGGTGCTGTCCGAGAGGCTG
CAGGCCCTGGTGAACAGTCTGTGTGCGGGGCAGTCCCCCTGAGACTCGGA
GCGGGGCTGACTGGAAACAACACGAATCACTCACTTTTCCCCACAAAAAA

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

GABRA (SEQ ID NO: 10)

GGGCTGGCTGAGCGCGGGCGAGTGTGAGCGCGAGTGTGCGCACGCCGCGG
GAGCCTCTCTGCCCTCTCCTCGCACCCTGCTCAGGGCATCTGAAGAGCCT
GGAAACGTGAACAGGCTTGAAGTATGGCATGTTGCAAAGATGGTTTCTGC
CAAGAAGGTACCCGCGATCGCTCTGTCCGCCGGGGTCAGTTTCGCCCTCC
TGCGCTTCCTGTGCCTGGCGGTTTGTTTAAACGAATCCCCAGGACAGAAC
CAAAAGGAGGAGAAATTGTGCACAGAAAATTTCACCCGCATCCTGGACAG
TTTGCTCGATGGTTATGACAACAGGCTGCGTCCTGGATTTGGGGGTCCTG
TTACAGAAGTGAAAACTGACATATATGTCACCAGCTTTGGACCTGTTTCT
GATGTTGAAATGGAATACACAATGGATGTGTTCTTCAGGCAGACATGGAT
TGACAAAAGATTAAAATATGACGGCCCCATTGAAATTTTGAGATTGAACA
ATATGATGGTAACGAAAGTGTGGACCCCTGATACTTTCTTCAGGAATGGA
AAGAAATCTGTCTCACATAATATGACAGCTCCAAATAAGCTTTTTAGAAT
TATGAGAAATGGTACTATTTTATACACAATGAGACTCACCATAAGTGCGG
AGTGTCCCATGAGATTGGTGGATTTTCCCATGGATGGTCATGCATGCCCT
TTGAAATTCGGGAGTTATGCCTATCCAAAGAGTGAGATGATCTATACCTG
GACAAAAGGTCCTGAGAAATCAGTTGAAGTTCCGAAGGAGTCTTCCAGCT
TAGTTCAATATGATTTGATTGGGCAAACCGTATCAAGTGAAACCATCAAA
TCAATTACGGGTGAATATATTGTTATGACGGTTTACTTCCACCTCAGACG
GAAGATGGGTTATTTTATGATTCAGACCTATATTCCGTGCATTATGACAG
TGATTCTTTCTCAAGTTTCATTTGGATAAATAAAGAATCAGTTCCCGCT
AGGACTGTATTTGGAATAACAACTGTCCTCACCATGACCACACTAAGCAT
CAGTGCACGACATTCTTTGCCCAAAGTGTCCTATGCTACCGCCATGGACT
GGTTCATAGCTGTCTGCTTTGCTTTTGTATTTTCGGCCCTTATCGAGTTT
GCTGCTGTCAACTATTTCACCAATATTCAAATGGAAAAAGCCAAAAGGAA
GACATCAAAGCCCCCTCAGGAAGTTCCCGCTGCTCCAGTGCAGAGAGAGA
AGCATCCTGAAGCCCCTCTGCAGAATACAAATGCCAATTTGAACATGAGA
AAAAGAACAAATGCTTTGGTTCACTCTGAATCTGATGTTGGCAACAGAAC
TGAGGTGGGAAACCATTCAAGCAAATCTTCCACAGTTGTTCAAGAATCTT
CTAAAGGCACACCTCGGTCTTACTTAGCTTCCAGTCCAAACCCATTCAGC
CGTGCAAATGCAGCTGAAACCATATCTGCAGCAAGAGCACTTCCATCTGC
TTCTCCTACTTCTATCCGAACTGGATATATGCCTCGAAAGGCTTCAGTTG
GATCTGCTTCTACTCGTCACGTGTTTGGATCAAGACTGCAGAGGATAAAG
ACCACAGTTAATACCATAGGGGCTACTGGGAAGTTGTCAGCTACTCCTCC
TCCATCGGCTCCACCACCTTCTGGATCTGGCACAAGTAAAATAGACAAAT
ATGCCCGTATTCTCTTTCCAGTCACATTTGGGGCATTTAACATGGTTTAT
TGGGTTGTTTATTTATCTAAGGACACTATGGAGAAATCAGAAAGTCTAAT
GTAATTTCGTTGCTATAGTAGTTTGCTAAAAGATGATGAAAATGCAGAAT
GTCTTTTTAAATGTTTTTAAATATAAACAAATATTCTTTACTAAAATAAA
AACTCTGTGTAATTTTTCCATTTAAAGATATAAGCCAGTTATTGGGAGAG
TTAATTAATTCCTGAGTGAAAAAGTGAACTATGTTTTTTTCAGAAAAAT
TATTTTAAAAGAACTCAGCATTCAGTTAGATAGAATACACACCATCCTGG
AAAGTTGGGATAAGAGAAATAGAGCTATTAGAGACAAGTGGCGCATATTT
TTTCATTGATATTTGAAAACAGACTATGACATTTTAAAAATCTGCCCTAT
GAGTATCAACCTGCCACCCTAAATTTCCCAGTGGCACTACCCTTAACCAG
AATTGTTTATTAGATGTCATATGCAGTGACCTTTGGTGATCTTCTTAGGA
ACTTCAAGAAAAGGAATTTTCCTGTTAAATTAAACATTGGCAAAAGGAAA
TGGAATAGTATAAACACTGATCAATAGAGTAAAATATCTGCTGCATAAAA
AACTAAGACAAAGACCAGAGGAAATATCTTCCCTTTCTTATGTTGGCTAA
ACAGTACTTAACAGTTGACTTGAAATTTTGTTCTCTGAGCCAAAGTTTAA
CTCATTGTATGAATTCTTTTTCATGGTAGTTCATTCAGTTATGTGTTTAT
TTACTACATAGTTATTCAGAGCCTACTGTGTTCCAGGAACTATGCTAGAA
ACTGTCTCTCTAGGAAAGCTCTTGCACCTTTATCTACAATATTACTTAAA
AAGTAGAACAGTCAATGCATGCCAAAGAACCATAAACTAGCAGAGGACAT
TGCATTCTTTAGTGAAGGACATTTATTTAGAGTCTGACAACATATTCAAA
ATATTTTTCAGCCTCTACTGATAGTGGATAACAAATATATTTGTTCACAT
AACCACTTTGATGTCAGTACAACTTCAGCAATTGGTTTTCAAAATAGATG
AGAATATGGTACAGATTGTTCTATAAGTGAAAAGCATTATGTACTTGAAA
GTAAAAATCAGGGCAATATAAGACTTAATAGATTAACTGTCGCAAATTTG
ATCAGAGTCACAGAGTAGAATTTGATCAGAATCACAGAATCATCAGACAT
AGGAACTGAGCACAGGCTTTTTCAGGTGCTTTCCCCAAGATAGATCTAGA
TATTAGCTAGTGAAATGCTAAATTTGAAGAGTTTTGTGTCCGTAGTTCT
GTAATTCTGGGCAGTCATCATGTTGGTTTTTTTGGGAGTTTTTTTAAGGT
TTAATAACTAAGGGGAATATTTTAAAATTAAGAGAGCAGCAAATGAAAGG
AGTAAAGAAAAAAATAGCTGTCGGGTAGGATGCCACTGACTCTGCTATGT
GATTTATCAGGGTTTTCATCTACTGACTTCTTTCTCATTAGGTAGGCTTA
ACAACTTACTTGAGAATTTTGCAACTGTCTATGCAGCTGAATCTAAGTAT
GGTTTTTTGTCATATTGCCTCTAGATTTTCTTCTGTGCTTCTCTCTATCT
GCTCTGGAATGGATGAGTGAATGTGTTCTGGGTGTTTTAGGGAACATATT
GATAGAAATGACCACCTTGCAGACAAAATCTCTCTCTCTCTTTTTGTTTT
TATAGAAAAGAAGTGATAGTAGTTAATTGGCATCGATTTTTCAGATATTG
CACTACCTTATAATGGTTGTTTTTGATACCTGAAAATTGTGCAAATGCCA
AATATTAATTGTAAGTCATATCTGAGAAATCATTCTTGGCTGTCTTTCTA
GGTATTCCATAGAATCAACACATTTTAAGGCTGAAAGATACTGTCGAAAT
CACCCAGTCCCAACCCCCCAATTTAAAATTGATTCTAGTAAAATTAGGTC

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

CAGTAACACCTGTATATATGTATATATTTAATAAAGAGTACTTGTACAAA
AAAGCTTATCATAAATTATTTCATGAATGTGAATAGATTTCTGGCCTTGA
GGACGATGTTTGGAAATATGGTTGGAAGCACAATTCATTCGCTACTAGTT
ATTCAGAGCGTACTTTGTTCCAGGAACTATGCTGGAAACTGATAGTTCAC
TATTCTGATGAAAAGGCTGGTTTTGTTGTTGTTGTTGTTGTTGTTGTTGT
TGTTTTTGGTGAGGAACTCTTACTCTTTGCTAATCTATTGGCCTATCTTA
AGAAATAATTATTTGGTTATTCATTGGCTTCCTTTAAAAAAAAGTGTTCT
TCTACAAATCTTACAGAGTGTAAAGAGATAAAAAGAAATGATTTTTTTTC
TTACCTTTACATATGAAGGTTTAAAAATACATCATGTGGCCAAAGAATGA
GAAAGGACAGAATTAACCAAGGATTCTTAATTGTTAATTTGAAGAACACA
TTAACCAGAAAGCTTAAACATTATTATTAAAATAAATTATTTCATTTGCA
CACAATGATAATAATGATGATAATAATAATAATAATAATAATAATAATAA
TAATAATAATAATATGTTGTTTGCTTTCCTTAACTGAATTTCATCAAATT
CATTCAGTGATTTTTATTTTGGTCATTATTTCTATCTTCCCAATAACCCA
GAGGTACATCAAGTAAAAACACTTTTGCAAAGAGCCAGTCACTTTTCCCT
CTTAGAAAATCTCAGAGAATGATTAGGGGCACCCAAAGTTCTGGTTATC
TATGAATAATAATGAATAATTTTGGCTGAGAATGGTACCTTTATATAACT
CTTTTAAAGATGAAATTCAGAATAATTTTATTCAGGACCTAGTATCTGCA
GTCCATGTTGGCCACTAACTGCTACATAATTACTTTCAATTTCCTCCAGG
CATGACTAGGTATAAACATATATTTACATGATTAATCCACATTTTAAAAT
GACTTGCACTTGTGCATATACATAGTACTTTGAATAATGTATATTTTAAA
TTGGACCTCACAAATCTTGTATTAAAGTAGGTAGAGAGTAGAGTCACACT
TTTTTTGATGAAATGAGTCACAGAGAAGTTACATGACAAAGATAAAATCA
CAGGGTTGGAAAGAACTTTGAAAGGTCATTTTTCAATAATCTCACCTTAA
AAGTGACCCCTTTTCAAACAAAGCATAAACAATTTATTTGTGGCTTATTT
TACCCATGAGCTGGCCAATACTTCCTGGCCTAGAAAAATATCTCCACTCT
CCCCATTCCTGTTCTTAATGGTCTTCTCTTCTCAATTTGTAAATATTCTC
CAGTAAAAGACACCAGGTGTGGAGATGGGTCACTTAATTTCAAGTTCTGA
GTGTCTTGTGGTTTTAAACAAGTCTCTTAACCTCTCTAAGACTGATTCCT
CATTTATAACAGGGAGGAGGTGGATTATGTAATATCTAAGAGCTTTTCAG
TTTTAATACTCTCTGATTCTCATAGTAAATACAAGCATACTCTTGTAAGA
AAAACACTGAATACTTTGAACCACAAATAAGTGTTTATGGACAAAAATTT
AGTTCTACTGCTTGATTACTTTAAGTTCATTGCTTGCTTCAAACTAAGGT
TTCCCTACCTTCAAAAATATATATAACATCTCTCCATTTAGATAAAGTAT
ATTCTTCCCCAGGGAAGACTGATATTCTTTAAAGACAGTAGAATATTGGCT
ATTTCTCTTTTCTGGGATTTCCTGGGCTTTTATTCACTAAATGGGCTCCT
GCCCAGTTTGGGTACTGTGCTGATTTTTAGATATACAGAGATAAAAATAG
CCCCTTTCCTTGCAGGTAGTCACAGTCCGGAAGAGATGATAGATGCATAG
ACAAAAAATTATGGGATGTAACTAATGCTTCAGTAGAATACAGCAGGGCC
AAAACTAGAGTGATACTCATCTCAGGCACAAATATATATGGGGACATCAA
AACTTCAATAATCAAGATACCTAATATTTAAGTGAATATTTTTAAAACTC
AAAATTAATGCAAAAGATTTATGATGAACAGAATATACAAATTTTAAATA
AATTAATAGAATCAGTAGTAATAATATTTTCTTCTGCCTCAGGCTCCAAA
ATTGCTCAGCATAGCACTGATCTAGATAGAGGTGGATAAAAGATCCACAT
AACTTAATTACATTGTTGAAGGAGAGGAACAAGAGTGATAGCAGAGAAGG
TTTCACAGATATAATCTTAAGCTAAATTTTATAGAATGATTTGGAGTTCT
TATAGCCTCCATTCCCACTTCCACAAACAAACAAAAAAATGAAAGCGCAA
TTTTATCAGCACCTGAGGCAGGAGAAGAGATGAGGATGTGGAAAGTCAAG
GGGAACTCTTACTACAAATTCTTAGTTCTGTGTTTGGAGGTAAGGGTGAA
TGCAGGGAAGTGAGAGTTGTTGATGTTGGAAAGACCTAAAGAGCCTGGAT
TAGGAAGAGTTTTGTGTAAATTACTGAAGGAATGGAATTTGATCAGGATT
AGTGGCAATTTATTAAAAATCTTGAAGAATAATACGATGAAAACTAACAT
CCTTATTTTTCTGTTTTAGAGAAAGCACCTGATTATTGTGTGAACTATGG
TTTGGAGGGCCACAAATCTAGAGGTAGTGGAACAGTTGAGATCTCTTATT
TTTTCTTTCCTGTCTTAAACTTTGCCTTCTATTCCTTTTTTCTTTTTTTG
ACCGCAATGACTTCATTGTCATTTGTAAAAGTGATACATGACTGTTAAAG
ATAGACATTGTAGAAACTTAAAAACAATCTCAAAATTCTACCACCCAGAA
ATCAGAAATATTTTGTATTTGGATATGTTTGTCTAGAAGAGTAGATTGCT
TGATTAAAAGACAGAGTTTTATAAATGTAGAAGCCAATATGACATACATG
CTGCCATTAAATAATAAAAAATTAAATTGACTTTTATCTCAAGATAAGAT
TAAAATTGGAGGGTAAAACTGAAGAAATTGTTGAAATTTGGATGGTGCTT
CTTTAAAGCAAGAGATTTAGAGAGTCAGAGCTTTTTATCCCAGGTTTCAA
TCTTTATTTCAGGAAAATTTTCTGCAATTTTGTCTAAGTTAATTTTTTTT
TTTTAAGAAATGCCAATTATGTCAAATCCCTTTTGTCTCTATACAATAGT
CCCCAACTGTTTGGCAACAGGCACGGGTGAGGGTGGGGAATGGTTTTC
AGATGAAATTGTTCCATCTCAGATCATCAGGCATTAGTCGATTCTCATAA
GGAGCGGACAACCTTGCATGCCCTCCTATGAGAATCTAATGCCGCCGCTA
ATCTGACAGGAGGCAGAGCTCAGGCGATAATGCTCAATGGGTGCCACTCA
CCTCCTGTTGTGCTGCCCAATTCCTAACAGGTCATGGATAAGTACTGGTC
AGTGGCCCAGGGGTTGGGGACCACTGCTCTGTAACTATTTACAGTATTCT
TTGTAACTACTTTGGTATCTTTAAAATTTTCTTTAACTTTTGTCAACCAT
AACCCTAGTGAGTTTTCAGTTGTGATTATTCTATTTTGTAACTTCCAATG
TACTTTTCAACTTCATAATGGTTAATTTTGTTTTCCATTGCTTTCTTGGT
CACTGTCATTTCATTTTTCTTCTCTTTCTCTATTTTTACCATTGCTTTAT
TGAAATATCTTCTTTGAGCTTCTCATGTTTCTCTATTAATGAGATCATGT
CTATAATATTTTTTGAGACTACAGAGACCTATTTATATAAACTCTTCCTC

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

TATTTCTTGAAAAAGTTTTTATCTGGCGTGAGCTTCATCTGCTTTTTCAT
TGAGGTTTTATCTCCCTTGCCTATTTTTGGGGCTGGTTTCTTTCTATTAA
TCACTGAGCAGAGCCAGCTATTTACTGAACTACAGTGTGGGAAGTGGTGG
GAGGGTGAGTCAGATCAGCCCACAGAAGCTATTTAAATTTCAGGTTTCAA
GCCCACCTCCCCAAAACCGTTTTATGTGTTTTTCTTCTGCCCAGGCACC
ATATTTTTATATCTATTTTTGACATTTGGGCGGCCTATGTAGTTCACAGT
GTAAAACTCTCTGTTTTACTTTCTTTATGTTATTGCTAGTGATTATTGCT
TGTAGTCCCACCCCCTTCCCCACATTAGCCTTAGTATTCTATATTATTCA
GCAAGCTTGTTCACAACTCTCAAATATAGTCTATCAGAATTTTTATCTTT
ACCTCTACATTCCACTATTCGGAAGTATATAGTAAAATCGTATGAAGACA
GATTTTGTCTTTTTCTTGCCTGTTTACACTCTATCTTACAGAGGTTTCAA
ACAAACCATCTTTGTTTGAAACATCGCAGGATAATGATACTTATTGAAAT
CTACATCCTGCCCAAGATATATGCCAGTCAATTTCCTTTCTCCTATTAGT
GCAAATGGCTACCTACTTAAAAGCTGCTGACTATAGTTTGTCATCAATTA
CTTGTTAATTACAGATATGGTTTTCATTTTTTTTTCTCAATTTTTCATTA
TGTTATTTTTGGAGACTGTCTTAGGTGGGGAGTGAATTATAAATATTTTT
ATTTCACCACCTTTAACTGAGTCACCATATGTTATTTGCACTTCCAATAG
ACCAGGGATTGACCAGAGTATCTTTTACTGATATGACCACCAGAGCTACA
TGGCTTTTACCTTCTGTATATCAGATGTCACTGGAATCAAGCATTAAACC
TAGATTAAATCTGGATTAAACCAGCTGTATGGCACCTTAGAAAATTGAGA
AGGACTAGGAAGCTGATAGAAAGAACTCCTGTATAAAAAATAAATTCTTT
TTACATTTTCCTTGGTAGTATTTCTGCAAGCTTCTTTAGTTTCTATAGGG
GAATCCCAGAGTTTTCCTCTGAGATTGCTTCCCTTTCCTTTGTATTTTCA
TTTTTCCCTCTTGGGCTTTACTTTTCAGTCGTGTATTTCTATCCCAATGT
TAATTTATTACACTGTTTATATTTTCCTGTCCTTCAATTCATCAGTAGAT
TAGTGAAGTACTTATTCCTTTAATTATAAGTATAAACGTTTTTAATTTCT
TTTTGGATAACGATACATTTAATGGAAAATTTTTAAATGCTATGGTTTCT
TAATAGCTTTTCTCTACCACTAATTACTTCCGTTAAAAAAAAAAAGAAAT
ACCCATGCGTAATATAAAAGAAATTTTGAATAAAATGTTATCCTTTCCTT
TTACTAGAGACAAACATCTCCACTTCAAAATGGAAAAATGGAACTATGCA
AAGGAAATTTACGATATTCAAGAGTATGATATTATCACTGAACCGATTAA
TTTAATTGAAAATACTAACCTGCAAAAAAGAATTACACAAATGTATTTGA
AATGTCATCAGATACCTCAAGCTATGACAGAGTTGATTATGTTACACAAG
TAGTAAAGGATAAATTAAATATATTCTATATTAACACTAAGATTTAAAAC
TAATTATAGTCTTCTTTAATTTTTCTACTGTATACATTTCATCTAGTTTT
CAGTAAAACAAACTTTTCATTACTTTTACTTATCCCATGCAAATCTAGTT
GCTATAAGATATAACCTAATTTGGAAATACCTCCCTGTAATACATTGGAA
TTTTGGTGTGAGTGTGTGTGATCAGAGAGGATAAACAAATGGTGTCAGCA
AAATAGAATGTAAAATATGGAGATAATGTGGATTTACACAATTTGATAAA
AATTCTCCCTTGAATTTTGCAGATCATATATGAATATCATCATGTGAAGT
GCAATTAGGATTTTTTCATATATTAATACATATACATCATCTCTTTAATA
AAATATTTTGCTGAACTCGTTTAATATTTCTCATGTCTCATATTTCATAT
TTTCTCATATGTCTCATATTTTATATTTTCTCATATGTGTCTCATTTTTA
TTATTACTATAGTATCCATTAAAGGAGACTGGCAAATACCTGAACAAAGT
TATGTTGTTGGCAATATAAGATATTACCAATTGCATAATATTATTTCCAA
AGGCAAATTAATATGCAAACTATAGATTTCCATGGGTATCTATACAAATT
ATTACTTGAAGTCCATAGAAAACAGCTTCCTTAGAGGGAAGTAAAAGAAG
CTCTGATAACAGACAATGTATAGCATTTCAGTTAAAGTTTGATTGACATA
TTTTTTTCTCAGTCTTTTATACTTGTGAATTATAGTCTACATTTTGTCTT
TACAGATGTTGCTAACACAGTGCAGCATGTTGGCTTGTCATTTTACTGAT
TATGTATATTGTCTCCTAGTTCAAGTATACAGTAAATCAGAGCTTTCATT
TTTCAAGGGGCAGAAAAATAATTGTTGGTTGATAAGGTAAGGTTATATGA
TTTTGAGGGAGCTTCATTGTAAATTGAATGAGAATCCGGTTTTCATGCAA
AGGTGTATCTATGCGATAATACTTTGAATGTCTGTAGTTTGAAATAGAAG
GTTAATTTTTTCCACTGGCTTATCCTTAATGAAGGAAATCCCCTGATAAT
TACTTTGATTCTGAAAATGTTGAAAACTCCAGAAGAAATAAAGCTTTTCT
TTGATTTCTCAGCTGAAGTGTTGTACAAACTGAGGAATATGAAGTCCATT
CCCTTCTTTCTTCTCTTGAATAATTTTAAAATTGTTTGTTTAGTTGTACA
ATTGAAAATATTCCTTATTATAGAAGTAAAAAAACAATAATGCATATTTC
CTCATATCATAAAAACTAAATTTGTTATCATCTGAGCTTCAATATTCTTG
CTCAATTAGAATAGTAAATATAAAGTGTGATATTTATAACAGTTCAAGGT
TTGATAGGAGATAGAGGTGTTTTGATTTTATGGGAAAATTACTTCCTCAA
GAACACATTTCTTGAGGTTTTAGTAATCACATTTGACTCCCTGAAATTGG
CAATTTTATTCAATGTAGGAATATTATCATGGTATATTATAGTGAGGAGC
ACATAGTCATTATTATTTTGTTTTTGCAAATTTATTTTGAAAAAAAGGAG
CATTATCAAATATTGGTTTACTATTTTAAAGTAATTCATCAGGAAATGAT
TTTTTAAACACTGTCCCTTTAAGTAAATGTCCCTTGCTTTTCAAAGCTCA
ACTTATTACTTATGGTAATAGAGTTACTTTGCTTCTTAAAACAAAGTTTA
TACTAGAGCATAGCATTGTAGAATATTATTCAGGTCTCAATTTCTCACTGGA
AAATGAGTCTTTAAAATAGTAAGGATTTAAATTTCTATAAAATTTAATCA
CAGATACTTATATTTTAAGATAAATGTGTTGGAGCTAAACTCTGGAATTA
TTAAAATATAAAACATTATATCCCTCTAATGTATTTTTTCTATTTAAATT
TAAACAATAAACATAAATATCTTTGGAAA

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

GCET (SEQ ID NO: 11)

CCACGCGTCCGGTGGTAAAGGGACGGAGGGGAAGCCCTGAGAGGACTGAG
AGGATGGGAAATTCTCTGCTGAGAGAAAACAGGCGGCAGCAGAACACTCA
AGAGATGCCTTGGAATGTGAGAATGCAAAGCCCCAAACAGAGAACATCCA
GATGCTGGGATCACCATATCGCTGAAGGGTGTTTCTGCCTTCCATGGAAA
AAAATACTCATTTTTGAAAAGAGGCAAGATTCCCAAAACGAAAATGAAAG
AATGTCATCTACTCCCATCCAGGACAATGTTGACCAGACCTACTCAGAGG
AGCTGTGCTATACCCTCATCAATCATCGGGTTCTCTGTACAAGGCCATCA
GGGAACTCTGCTGAAGAGTACTATGAGAATGTTCCCTGCAAAGCTGAGAG
ACCCAGAGAGTCCTTGGGGAGGAACTGAGACTGAGTATTCACTTCTACATA
TGCCTTCTACAGACCCCAGGCATGCCCGATCCCCAGAAGATGAATATGAA
CTTCTCATGCCTCACAGAATCTCCTCTCACTTTCTGCAACAGCCACGTCC
ACTTATGGCCCCTTCTGAGACTCAGTTTTCCCATTTATAGTGAAGTGGCT
GGACTAGCATTGTTTAGCACCAACAAATAAAAGGTGGGATGGGGGATCT
GCCTGAAGCAGGGATGGGACACAAAGTCCCTCCAGCTTATCTCCCACAAC
AACCCTTTCCCTGCAGAGCATGGTTTGTATACCACAAGCCCTCTTAGCAC
GCAAAAGCCAAAATCTAAAGATCAACCATATCCTGAACAACACCATTTGA
GAAAGAGGTAACCATCTTTGGTTCTACATGGTTTGGAGAGTATAGTGGTA
GGAGGGGCTCCCTGATTCCCCTAAAGCTATGCACACCACAAGGGGCTCTG
CTCTTCTGTCTGGGATCTTCTTATAAAGTGTTCCCATGATCATTCTCTAA
AGTCACGAGGAAGCTTTACTCATCATACTAAGTGTGCCCAAGGGGGAGTT
CACTCATTACTGTGACCTTCCAGCTCAGTCCCCACCCATGGGAGCCTGTG
TTGCTCCTCTCACTCCATGTGTCTAAGTCATGTCTTTTACATAGTGTCCT
TTGACCTGTTGGCCCCCATGGTCTGGTTAGTTATGTGAGTTGAATCAAGA
GGCTCTAGGCCAGATGTTTACATAATTTTAACCTATATGATTTTATTTTT
AACTTTGTATTTCTCCCTAGAAATCTTAATAAGACAATTATGCCATCAGA
CAATGTTAAGAAGAACGATCCTTGGAGATCCCGTAATCCCACTACCCTTC
TTTGGCTCAGAGAGGATAATTTGCCTAATGATACATTAAAGTTAGTGGCA
AAACTTAATTTGGAGCCTGATTTCCTACTGACTTCCAATTTAGTGCTCCC
CCAGTATGCTAAATAGAAAGCCCTCTGCAATATATTAAATGTATACTAAA
TGTATATATTTAATAATGTCATGTATAAAATATGAATAAAATGTCCACAT
AGGAAATTAACACATAAA

TIMD (SEQ ID NO: 12)

ATAAGAGGTTGGGCTTTGGATAGATAGACAGACTCCTGGGTCCGGTCAAC
CGTCAAAATGTCCAAAGAACCTCTCATTCTCTGGCTGATGATTGAGTTTT
GGTGGCTTTACCTGACACCAGTCACTTCAGAGACTGTTGTGACGGAGGTT
TTGGGTCACCGGGTGACTTTGCCCTGTCTGTACTCATCCTGGTCTCACAA
CAGCAACAGCATGTGCTGGGGGAAAGACCAGTGCCCCTACTCCGGTTGCA
AGGAGGCGCTCATCCGCACTGATGGAATGAGGGTGACCTCAAGAAAGTCA
GCAAAATATAGACTTCAGGGGACTATCCCGAGAGGTGATGTCTCCTTGAC
CATCTTAAACCCCAGTGAAAGTGACAGCGGTGTGTACTGCTGCCGCATAG
AAGTGCCTGGCTGGTTCAACGATGTAAAGATAAACGTGCGCCTGAATCTA
CAGAGAGCCTCAACAACCACGCACAGAACAGCAACCACCACCACACGCAG
AACAACAACAACAAGCCCCACCACCACCCGACAAATGACAACAACCCCAG
CTGCACTTCCAACAACAGTCGTGACCACACCCGATCTCACAACCGGAACA
CCACTCCAGATGACAACCATTGCCGTCTTCACAACAGCAAACACGTGCCT
TTCACTAACCCCAAGCACCCTTCCGGAGGAAGCCACAGGTCTTCTGACTC
CCGAGCCTTCTAAGGAAGGGCCCATCCTCACTGCAGAATCAGAAACTGTC
CTCCCCAGTGATTCCTGGAGTAGTGCTGAGTCTACTTCTGCTGACACTGT
CCTGCTGACATCCAAAGAGTCCAAAGTTTGGGATCTCCCATCAACATCCC
ACGTGTCAATGTGGAAAACGAGTGATTCTGTGTCTTCTCCTCAGCCTGGA
GCATCTGATACAGCAGTTCCTGAGCAGAACAAAACAACAAAAACAGGACA
GATGGATGGAATACCCATGTCAATGAAGAATGAAATGCCCATCTCCCAAC
TACTGATGATCATCGCCCCCTCCTTGGGATTTGTGCTCTTCGCATTGTTT
GTGGCGTTTCTCCTGAGAGGGAAACTCATGGAAACCTATTGTTCGCAGAA
ACACACAAGGCTAGACTACATTGGAGATAGTAAAAATGTCCTCAATGACG
TGCAGCATGGAAGGGAAGACGAAGACGGCCTTTTTACCCTCTAACAACGC
AGTAGCATGTTAGATTGAGGATGGGGGCATGACACTCCAGTGTCAAAATA
AGTCTTAGTAGATTTCCTTGTTTCATAAAAAAGACTCACTTAAAAAAAAA

BAMBI (SEQ ID NO: 13)

TTTACGGCGCGGAGCCGGAGAGACCTGGGCTGGCGCGGGCGGGAGCTGCG
GCGGATACCCTTGCGTGCTGTGGAGACCCTACTCTCTTCGCTGAGAACGG
CCGCTAGCGGGGACTGAAGGCCGGGAGCCCACTCCCGACCCGGGGCTAGC
GTGCGTCCCTAGAGTCGAGCGGGGCAAGGGAGCCAGTGGCCGCCGACGGG
GGACCGGGAAACTTTTCTGGGCTCCTGGGCGCGCCCTGTAGCCGCGCTCC
ATGCTCCGGCAGCGGCCCGAAACCCAGCCCCGCCGCTGACGGCGCCCGCC
GCTCCGGGCAGGGCCCATGCCCTGCGCGCTCCGGGGGTCGTAGGCTGCCG
CCGAGCCGGGGCTCCGGAAGCCGGCGGGGGCGCCGCGGCCGTGCGGGGCG
TCAATGGATCGCCACTCCAGCTACATCTTCATCTGGCTGCAGCTGGAGCT
CTGCGCCATGGCCGTGCTGCTCACCAAAGGTGAAATTCGATGCTACTGTG

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

ATGCTGCCCACTGTGTAGCCACTGGTTATATGTGTAAATCTGAGCTCAGC
GCCTGCTTCTCTAGACTTCTTGATCCTCAGAACTCAAATTCCCCACTCAC
CCATGGCTGCCTGGACTCTCTTGCAAGCACGACAGACATCTGCCAAGCCA
AACAGGCCCGAAACCACTCTGGCACCACCATACCCACATTGGAATGCTGT
CATGAAGACATGTGCAATTACAGAGGGCTGCACGATGTTCTCTCTCCTCC
CAGGGGTGAGGCCTCAGGACAAGGAAACAGGTATCAGCATGATGGTAGCA
GAAACCTTATCACCAAGGTGCAGGAGCTGACTTCTTCCAAAGAGTTGTGG
TTCCGGGCAGCGGTCATTGCCGTGCCCATTGCTGGAGGGCTGATTTTAGT
GTTGCTTATTATGTTGGCCCTGAGGATGCTTCGAAGTGAAAATAAGAGGC
TGCAGGATCAGCGGCAACAGATGCTCTCCCGTTTGCACTACAGCTTTCAC
GGACACCATTCCAAAAAGGGGCAGGTTGCAAAGTTAGACTTGGAATGCAT
GGTGCCGGTCAGTGGGCACGAGAACTGCTGTCTGACCTGTGATAAAATGA
GACAAGCAGACCTCAGCAACGATAAGATCCTCTCGCTTGTTCACTGGGGC
ATGTACAGTGGGCACGGGAAGCTGGAATTCGTATGACGGAGTCTTATCTG
AACTACACTTACTGAACAGCTTGAAGGCCTTTTGAGTTCTGCTGGACAGG
AGCACTTTATCTGAAGACAAACTCATTTAATCATCTTTGAGAGACAAAAT
GACCTCTGCAAACAGAATCTTGGATATTTCTGAAGGATTATTTGCAC
AGACTTAAATACAGTTAAATGTGTTATTTGCTTTTAAAATTATAAAAAGC
AAAGAGAAGACTTTGTACACACTGTCACCAGGGTTATTTGCATCCAAGGG
AGCTGGAATTGAGTACCTAAATAAACAAAAATGTGCCCTATGTAAGCTTC
TACATCTTGATTTATTGTAAAGATTTAAAAGAAATATATATATATTTGTCT
GAAATTTAATAGTGTCTTTCATAAATTTAACTGGGAAACGTGAGACAGTA
CATGTTAATTATACAAATGGCCATTTGCTGTTAATAATTTGTTCTCAACT
CTAGGATGTGGCTTGGTTTTTTTTTTTCTCTTTTCTTTTTTAAACAAGAC
CAAGATCTTGCTTATTCTTCCATGAAAAAA

SASH (SEQ ID NO: 14)

ACGGCCATGGAGGACGCGGGAGCAGCTGGCCCGGGGCCGGAGCCTGAGCC
CGAGCCCGAGCCGGAGCCCGAGCCCGCGCCGGAGCCGGAACCGGAGCCCA
AGCCGGGTGCTGGCACATCCGAGGCGTTCTCCCGACTCTGGACCGACGTG
ATGGGTATCCTGGACGGTTCACTGGGAAACATCGATGACCTGGCGCAGCA
GTATGCAGATTATTACAACACCTGTTTCTCCGACGTGTGCGAGAGGATGG
AGGAGCTGCGGAAACGGCGGGTTTCCCAGGACCTGGAAGTGGAGAAACCC
GATGCTAGCCCCACGTCACTTCAGCTGCGGTCCCAGATCGAAGAGTCGCT
TGGCTTCTGTAGCGCCGTGTCAACCCCAGAAGTGGAAAGAAAGAACCCTC
TTCATAAATCAAACTCAGAAGACAGCTCTGTAGGAAAAGGAGACTGGAAG
AAGAAAAATAAGTATTTCTGGCAGAACTTCCGAAAGAACCAGAAAGGAAT
AATGAGACAGACTTCAAAAGGAGAAGACGTTGGTTATGTTGCCAGTGAAA
TAACGATGAGCGATGAGGAGCGGATTCAGCTAATGATGATGGTCAAAGAA
AAGATGATCACAATTGAGGAAGCACTTGCTAGGCTCAAGGAATACGAGGC
CCAGCACCGGCAGTCGGCTGCCCTGGACCCTGCTGACTGGCCAGATGGTT
CTTACCCAACGTTTGATGGCTCATCAAACTGCAATTCAAGAGAACAATCG
GATGATGAGACTGAGGAGTCGGTGAAGTTTAAGAGGTTACACAAGCTGGT
AAACTCCACTCGCAGAGTCAGAAAGAAACTAATTAGGGTGGAAGAAATGA
AAAAACCCAGCACTGAAGGTGGGGAGGAGCACGTGTTTGAGAATTCGCCG
GTCCTGGATGAACGGTCCGCCCTCTACTCTGGCGTGCACAAGAAGCCCCT
TTTCTTTGATGGCTCTCCTGAGAAACCTCCCGAAGATGACTCAGACTCTC
TCACCACGTCTCCATCCTCCAGCAGCCTGGACACCTGGGGGGCTGGCCGG
AAGTTGGTCAAAACCTTCAGCAAAGGAGAGAGCCGGGGCCTGATTAAGCC
CCCCAAGAAGATGGGGACATTCTTCTCCTACCCAGAAGAAGAAAAGGCCC
AGAAAGTGTCCCGCTCCCTCACCGAGGGGGAGATGAAGAAGGGTCTCGGG
TCCCTAAGCCACGGGAGAACCTGCAGTTTTGGAGGATTTGACTTGACGAA
TCGCTCTCTGCACGTTGGCAGTAATAATTCTGACCCAATGGGTAAAGAAG
GAGACTTTGTGTACAAAGAAGTCATCAAATCACCTACTGCCTCTCGCATC
TCTCTTGGGAAAAAGGTGAAATCAGTGAAAGAGACGATGAGAAAGAGAAT
GTCTAAAAAATACAGCAGCTCTGTCTCTGAGCAGGACTCGGGCCTTGATG
GAATGCCTGGCTCCCCTCCGCCTTCACAGCCCGACCCCGAACACTTGGAC
AAGCCCAAGCTCAAGGCCGGGGGTTCTGTAGAAAGTCTTCGCAGTTCTCT
CAGTGGGCAGAGCTCCATGAGCGGTCAAACAGTGAGCACCACTGATTCCT
CAACCAGCAACCGGGAAAGCGTCAAGTCGGAAGATGGGGATGACGAAGAG
CCGCCTTACCGAGGCCCGTTCTGCGGGCGTGCCAGGGTGCACACCGACTT
CACCCCCAGTCCCTATGACACAGACTCACTCAAGCTCAAGAAGGGAGATA
TCATCGATATAATCAGCAAGCCACCCATGGGGACCTGGATGGGCCTGCTG
AACAACAAAGTCGGCACGTTCAAGTTCATCTACGTGGACGTGCTCAGTGA
AGACGAGGAGAAACCCAAACGCCCCACCAGGAGGCGTCGGAAAGGACGAC
CACCCCAGCCCAAGTCTGTGGAGGATCTCCTGGATCGGATTAACCTAAAA
GAGCACATGCCCACTTTCCTGTTCAATGGATATGAAGATTTGGACACCTT
TAAGCTGCTGGAGGAGGAAGACTTGGATGAGTTAAATATCAGGGACCCGG
AACACAGAGCTGTTCTCTTGACAGCAGTGGAGCTGTTACAAGAGTATGAC
AGTAACAGCGACCAGTCAGGATCCCAGGAGAAGCTGCTCGTTGACAGCCA
GGGCCTGAGTGGATGCTCACCCCGAGACTCAGGATGCTACGAAAGCAGTG
AGAACCTGGAAAACGGCAAGACTCGGAAAGCTAGCCTCCTATCTGCCAAG
TCATCCACCGAGCCCAGCTTGAAGTCTTTTAGCAGAAACCAGTTGGGCAA
TTACCCAACATTGCCTTTAATGAAATCAGGGGATGCACTGAAGCAGGGAC
AGGAGGAGGGCAGGCTGGGTGGTGGCCTTGCCCCAGACACGTCCAAGAGC

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

TGTGACCCACCTGGTGTGACTGGTTTGAATAAAAACCGAAGAAGCCTCCC
AGTTTCCATCTGCCGGAGCTGTGAGACCCTGGAGGGCCCCCAGACTGTGG
ACACTTGGCCCCGATCCCATTCCCTGGATGACCTTCAAGTGGAGCCTGGT
GCTGAGCAAGACGTGCCTACCGAGGTGACAGAACCGCCCCCTCAGATTGT
ACCTGAAGTGCCACAGAAGACGACCGCCTCTTCCACGAAGGCCCAGCCCC
TGGAGCGAGACTCTGCTGTCGACAATGCATTGCTACTGACCCAAAGCAAG
AGATTTTCTGAACCTCAGAAATTGACAACTAAGAAACTGGAGGGCTCAAT
CGCAGCCTCTGGTCGCGGCCTGTCACCCCCTCAGTGTTTGCCCAGAAACT
ATGATGCTCAGCCTCCTGGAGCTAAACACGGTTTAGCAAGGACGCCTCTG
GAGGGCCACAGAAAAGGACACGAGTTTGAAGGAACACACCATCCCCTGGG
CACCAAAGAAGGGGTAGATGCTGAGCAGAGAATGCAGCCCAAAATTCCAT
CACAGCCTCCACCTGTTCCTGCCAAAAGAGCAGAGAACGCCTTGCTAAC
GGACTCCACCCTGTTCCCATGGGCCCCAGTGGGGCCCTCCCCAGTCCCGA
TGCGCCATGCCTGCCAGTGAAAAGGGGCAGCCCCGCCAGCCCCACCAGCC
CTAGCGACTGTCCCCCAGCACTGGCTCCCAGGCCTCTCTCAGGGCAGGCG
CCTGGCAGCCCACCAAGCACAAGGCCGCCCCCCTGGCTCTCAGAGCTCCC
CGAGAACACAAGCCTCCAGGAGCACGGTGTGAAGCTGGGCCCGGCTTTGA
CCAGGAAGGTCTCCTGTGCCCGGGGAGTGGATCTAGAAACGCTCACTGAA
AACAAGCTGCACGCTGAAGGCATCGATCTCACGGAGGAGCCGTATTCTGA
TAAGCATGGCCGCTGTGGGATTCCTGAAGCCCTGGTGCAGAGATACGCAG
AGGACTTGGATCAGCCCGAGCGGGACGTCGCCGCCAACATGGACCAGATC
CGGGTGAAGCAGCTTCGGAAGCAGCACCGCATGGCGATTCCAAGTGGTGG
ACTCACGGAAATCTGCCGAAAGCCCGTCTCTCCTGGGTGCATTTCGTCTG
TGTCAGATTGGCTCATTTCCATCGGTCTGCCCATGTACGCCGGCACCCTC
TCCACCGCGGGCTTCAGCACACTGAGCCAAGTGCCTTCTCTGTCTCACAC
TTGCCTTCAGGAGGCCGGCATCACAGAGGAGAGACACATAAGAAAGCTCC
TATCTGCAGCCAGACTCTTCAAACTGCCGCCAGGCCCTGAGGCCATGTAG
CCAGGCCCGGAATGGGCCTCTCTGGACAAGAGCCACCCTTTCACTGTGCA
TATGATGCTGATGCAATTCCTCCATCATCTCTGGACGTGCAGACCAGATC
CAGAAGAAAGGCCTGGCGTGTGGCCAAACAGCGTGAAACCTTGGCACAGG
ACTGAGGATCCTCTCCTCCAGAAAAGCCCCCTCGAGGAAATAAATTAGTG
CGGTTCTCTTTGACCTCCAAAGACAAGACAAGCACTTATTTTTATTTTCA
GAAGACAAAAGAACCAAGATGCCAACTGGCTGCGAATGCTCTATCTCCAG
TCTGTCTCTGTGTACTGGTAGAGGCTGGGAGGAGTAGGGGGCAGCCTGTT
CCATTTCTGATAGTGCCCTTGCTCTTCTGTCTGTCATCTTGCAGGATGCC
CGAGGGCCAGATGGGCTTAGCTAGGCCAAAGTAACAGACTCAAGAGTTAT
TGTACATTACTGACCACGCTCATTTGTTCAAAAGTTAGAACATCTGGCTG
CACCAGGAAAAAAAAAAAAAAAAAAGTCCTGTTCTTCTTTAGATAAACAAG
AGACATTTTCATAATTGCTTTCTAGCAATCAGCTTTTATTTGCCTTAATA
TAAGCTTTTAAGCAGTTATCTAACTAGTGTCCACAACCCTGTAACCATAC
TTCCACATCTTCAGCTTAGGCAGACATCGAACCTCTCTGGGATGTTTCCA
GCAAAAGTGAGCTTTTCTAATCGTCTCATTGTAACATGGCTTATTTTGTA
GAGGTATTCATCAGCCACACACTTCATGTTGGTTTTTGGTTTTTAAGCTA
ACTACAAATCTAGTAAAAGCTATCTGAAATTCACAAATATCATGTGTGT
GCGTGCGTGCGTGCGCGTGTGTGTCTGTATTCATAGTGACTGCTTTTGGT
TTTAACCAGTTTAGTATCGTTACTGTGTGGATCGTCGCGCTGCAGTATTG
ACTTGGAATCCTGACCATGTCCATCCCAAAATTCAGTCCTCAGTTAACGG
ATCATGTTTGCAAAAGGTCACTGTGAGGCTGCATATTTCAGAAAGATGTC
CTTAATAAGGGAAGTCATGTATAAGATGTTTTCTAAAAGACTTTTCAGTA
TTACAACTAATACTATTATTATCCTTCTTTTTTTATTTAGATAATTCTTT
TAATTTAAACAAGGTTCACTATGGAACCAGACAAATCTCATTAGCCATG
TGTTAAGTATTTGCTACTTTAAATTGTTTTACAACTGATTTCAGCACATT
CTATCCTTTTTTTTTTTTGAAATGGAGTTTCGCTCTTGTCACCCAGGCTG
GAGTGCAATGGCACGATCTTGGCTCACTGCAACCTCAGTCTCCCAGGTTC
AAGTGATTCTCCTGCCTTAGCCTCCCGAGTAGCTGGGATTATAGGCACCC
ACCACCACGCCCAGCTAATTTTTGTATTATTAGTAGAGACAGGGTTTCAC
CATGTTGGCCAGGCTGGTCTCAAACTCAACTCCTGACCTCAGGTGGTCCA
CCCGCCTCAGCCTCCCAAAGTGCTGGGATTACAGGTGTGAGCCACCGCAC
CTGGCCTCTGTCCTCTTTTAGTCTAGTGTCTGGTTTTCTAGCAAACAGTA
AATTTAAACAAGTAAACTATTATGGTTTCCATTGCTTACAAAATGATTTT
CCTTTACATTCTTATCATGAACACTATTTTAAGCATCAAATGCAATCATC
TAAAATATAAAGGTCAATCATTTATAATAGAAACACCTTGACCACAAGCC
CTTGATTGAACATTTATAATATTTCATCTACTTATTAAAACAAATAATT
TCCCTTGGGTTGGAGGGGAAGTGATTTCATAAATTAATTAGAAAGCCATC
TTTAGCATATTGCTTATGTCTGGATCCATGTTTCTGAGGAAAAAGACATT
CTCAGGTGATGTATTTTTTTCATGCATTAGTATGCATTTTTAAAAAATAA
TGCATGTTTCTTTAATAATTAATTTTCATCTTCTATAAGATGCCATGTGA
AGAAGTTGTGGAAATGTAGAATAAAAAGCTAAAGCTGCCAAATTTCTGTT
GAACTCTTAAAAACAGCTCATGTTTGTTTGTCCTCTCGGGTTGTGGCCTA
GCCTATTTGCAATGTAATGAAGCTGCAGGGTTCTTGTATAGCTAAAGCGT
TCAATGCATTTCACGTGCTGTGGTGGATGTGGGTGCTGTAGACAGGCTTC
TTCTCTTCCTGCTCTCAAAATACCTCGGCTTGACATTTGGACAGATCCTG
TCATTGTTTAAGCTGAGCAAAAAACCACACAAAAGTTGTGTAAGAGATGA
GATAACAAAGGAGCGAGAGAAATCTCATGTGAATTTCCAAGTTTTAATTC
GTTCTCCATGAAGGATTTTCATTTCAGTGAAAGTCGCAGCAGAAGAGGGA
ACTTTCTGGAGTTTTTGAGAATGCCAAACCACATTTTTATCACACTTCTT

TABLE 5-continued

ILLUSTRATIVE HUMAN DASD POLYNUCLEOTIDE SEQUENCES RETREIVED FROM GENBANK LIBRARY DATABASE USING THE DISCLOSURE IN TABLES 1-4

TGGAAATCAATGCCTTTGCATAGAAAATCAAATTCAGGGACCACAAAGAA
TTTTCAGTGGGAATGTCTAGTCTGAGGGGTCTGAGGTTTGTTTTACTTTA
TTGTGTTGTTTAAATATTTTAAAAATATCTTTAGCGTTTGGTCTTTTTTT
TTTCTGTAAACATTTAATTTGGTCTGAGAAAAGCTGAATGTTTGGGTGTG
ACGTTTGACTGAGGTGGATTGGGGCTGCCTGTGGACATTAGTGAACAGGT
GGTAGGCTTCAGGAATATCCAGTTTTAATCAGTTGCATTTGGTACAGAAT
TTTGAGTAATGGTGAAAATTGTTGTCTTTGGAAAGCACAAAAGAAACCTG
GAAAGGCAGTTCGGCTCAGGTAGCTACACATAACATTGTGTATGATTTTC
ACTTCAAAGCTGTCTGGAAGGAAATGCAGTCAGCTCCAGCTAGTACTATT
TATGTACCCAGATAACTAAGATATTGTTTCATGGCCTTGCCTTAGTCAGA
GGCCCTTTTCTCTGTCCTGAACCCCCAGGTATGGGTGAAATTGGAAATTA
CTAATCTATTGGAAATCAGTTCCTGACATAGTAAAGTTTGCTTTCATAAC
TGCAGCAAAAAAGGTCAACTTGCCAAGTCACTGCTGCCATGTGTGTACTG
TATTATTTTCAGAAAAAAATATAATAGTCTGAGTCCAAGTTATCTTGATT
TAAAATTGATAGAGAAAAGAAACTGTCGAGCAAGTTATATAACAACTAAC
AACATTGCACTTTCTGTATATGAAATCAATATTTAAATAACTTATTTTTC
TCCATTGCTGTTCTTAAAAACATTGTAAGTAGCTGTAATATACCAGTACC
AATATGTTCTTGCAATTGCTTCAGCCCAAGAAAGCTGTGTATTGTTTTAA
AAATTGTAAAAATTATTGTGATGATTCATTTAGCATAAAGAGAGGTGGAC
GGAAGGGTTTTCCTATGTATCAAAACTTGTCTATAATTATGTCATCTATG
TACCTAGAAAAAAGTAAATAAATTTCTTCAGTTGAATATG

DACT (SEQ ID NO: 15)

GGCGGTCGCGCGCAGGACTCGAGGGCTTCTAGCCACCGTCCCCGCCAGCG
CCGCGCCCCGCCACAGGGCGGCATGAGCCCACCCGCGGCCGCAGCCCTAG
CGCCCTGCTCCTCCGCCTGGGCGGCCCGGCTGCGGTGACGGCTCTCGCTG
CCCGACTGGGGGCCATGAAGCCGAGTCCGGCCGGGACGGCGAAGGAGCTG
GAGCCTCCGGCGCCGGCCCGAGGCGAGCAGCGCACGGCGGAGCCCGAGGG
GCGCTGGCGGGAGAAGGGCGAGGCAGACACCGAGCGGCAGCGCACCCGGG
AGCGGCAGGAGGCCACGCTGGCCGGGCTGGCGGAGCTGGAGTACCTGCGC
CAGCGCCAAGAGCTGCTGGTCAGGGGCGCCCTGCGCGGCGCCGGGGGTGC
GGGAGCCGCTGCGCCCCGCGCTGGGGAGCTACTGGGGGAGGCGGCGCAGC
GCAGTCGCCTGGAGGAGAAGTTCTTGGAGGAGAACATCTTGCTGCTAAGA
AAGCAATTGAACTGTTTGAGGCGAGAGATGCTGGTTTGTTGAATCAGTT
GCAAGAGCTTGACAAGCAGATAAGTGACCTGAGACTGGATGTAGAAAAGA
CATCTGAAGAGCACCTGGAGACAGACAGTCGGCCTAGCTCAGGGTTTTAT
GAGCTGAGTGATGGGGCTTCAGGATCCCTTTCCAATTCCTCTAACTCGGT
GTTCAGTGAGTGTTTATCCAGTTGTCATTCCAGCACCTGCTTTTGCAGCC
CCTTGGAGGCGACCTTGAGTCTCTCAGATGGTTGCCCCAAATCTGCAGAT
CTCATAGGATTGTTGGAATATAAAGAAGGCCACTGTGAAGACCAGGCCTC
AGGGGCAGTTTGCCGTTCCCTCTCCACACCACAATTTAATTCCCTTGATG
TCATTGCAGATGTGAATCCCAAGTACCAGTGTGATCTGGTGTCTAAAAAC
GGGAATGATGTATATCGCTATCCCAGTCCACTTCATGCTGTGGCTGTGCA
GAGCCCAATGTTTCTCCCTTTGTCTGACGGGCAACCCTCTGAGGGAAGAGG
ACAGGCTTGGAAACCATGCCAGTGACATTTGCGGTGGATCTGAGCTAGAT
GCCGTCAAAACAGACAGTTCCTTACCGTCCCCAAGCAGTCTGTGGTCTGC
TTCCCATCCTTCATCCAGCAAGAAAATGGATGGCTACATTCTGAGCCTGG
TCCAGAAAAAAACACACCCTGTAAGGACCAACAAACCAAGAACCAGCGTG
AACGCTGACCCCACGAAAGGGCTTCTGAGGAACGGGAGCGTTTGTGTCAG
AGCCCCGGGCGGTGTCTCACAGGGCAACAGTGTGAACCTTAAGAATTCGA
AACAGGCGTGTCTGCCCTCTGGCGGGATACCTTCTCTGAACAATGGGACA
TTCTCCCCACCGAAGCAGTGGTCGAAAGAATCAAAGGCCGAACAAGCCGA
AAGCAAGAGGGTGCCCCTGCCAGAGGGCTGCCCCTCAGGCGCTGCCTCCG
ACCTTCAGAGTAAGCACCTGCCAAAAACGGCCAAGCCAGCCTCGCAAGAA
CATGCTCGGTGTTCCGCCATTGGGACAGGGGAGTCCCCTAAGGAAAGCGC
TCAGCTCTCAGGGGCCTCTCCAAAAGAGAGTCCTAGCAGAGGCCCTGCCC
CGCCGCAGGAGAACAAGTTGTACAGCCCCTGAAAAAGATGTCACAGAAA
AACAGCCTGCAGGGCGTCCCCCCGGCCACTCCTCCCCTGCTGTCTACAGC
TTTCCCCGTGGAAGAGAGGCCTGCCTTGGATTTCAAGAGCGAGGGCTCTT
CCCAAAGCCTGGAGGAAGCGCACCTGGTCAAGGCCCAGTTTATCCCGGGG
CAGCAGCCCAGTGTCAGGCTCCACCGGGGCCACAGGAACATGGGCGTCGT
GAAGAACTCCAGCCTGAAGCACCGCGGCCCAGCCCTCCAGGGGCTGGAGA
ACGGCTTGCCCACCGTCAGGGAGAAAACGCGGGCCGGGAGCAAGAAGTGT
CGCTTCCCAGATGACTTGGATACAAATAAGAAACTCAAGAAAGCCTCCTC
CAAGGGGAGGAAGAGTGGGGGCGGGCCCGAGGCTGGTGTTCCCGGCAGGC
CCGCGGGCGGGGGCCACAGGGCGGGGAGCAGGGCGCATGGCCACGGACGG
GAGGCGGTGGTGGCCAAACCTAAGCACAAGCGAACTGACTACCGGCGGTG
GAAGTCCTCGGCCGAGATTTCCTACGAAGAGGCCCTGAGGAGGGCCCGGC
GCGGTCGCCGGGAGAATGTGGGGCTGTACCCCGCGCCTGTGCCTCTGCCC
TACGCCAGCCCCTACGCCTACGTGGCTAGCGACTCCGAGTACTCGGCCGA
GTGCGAGTCCCTGTTCCACTCCACCGTGGTGGACACCAGTGAGGACGAGC
AGAGCAATTACACCACCAACTGCTTCGGGGACAGCGAGTCGAGTGTGAGC
GAGGGCGAGTTCGTGGGGGAGAGCACAACCACCAGCGACTCTGAAGAAAG
CGGGGGCTTAATTTGGTCCCAGTTTGTCCAGACTCTGCCCATTCAAACGG
TAACGGCCCCAGACCTTCACAACCACCCCGCAAAAACCTTTGTCAAAATT
AAGGCCTCACATAACCTCAAGAAGAAGATCCTCCGCTTTCGGTCTGGCTC
TTTGAAACTGATGACGACGGTTTGAGTGACATCATTGGTGTAGAAAGTTT
GTGTGTTTTTTTTTCTTCTCCCTAGTTGCCAAAATTAAAAAGGTGGTGTT
TTCATTTTTGTATAATACTTTAATGGAATGCTTTTTAAAAAAATATAAAA
CCAAGGTAAATTATTGTTTCATCTTCACGTATGGATGCTAGTGCCTTTAA
TGGAAGGTAAAGAATGTTTTGCTAGTTAGAAGTACATATTGAGGTTTTAA
TGGTGGTGATAGTGAGTTTTGTGGCACCAGCTGTTTTTTATTTTAAACTT
TCTGAGCATCCGGCAAGGTACAGGTTTTGATGTTCAAGTTTTATTGGGAT
AAGATCTTTTGATCCCAAGGTCAGGTGGATGGAATTTTTGGATTTATATT
TGTTCCTTGAGTCTTCAGGGCAGTGTCTCCATGAGGGTTTTCCTGTTGAG
GGGCACCACATACAATAGTGTGAAGTAGGTATGAGGGGCAGTCATTGTAT
TCTATAGTTTTTTTATGTAGTCTACATTTCTCAGATGTATCCCCATTCGG
TTTTATTCTCAGAACTGTTACTAGACTCATGACTTGGAGGCCAAACCTTA
AATCCAGAGATAGCAGCCTCGATAGGGACCTTAAAAGGATTCACAAAAAC
TTTTGCCACACTTGGTGCCTAGGCCCTGTTCCTAATAACCCCTTCTAGGG
CCGTTTATCCAACATTTAGATGCCTTCTTTTCCCTCCCTAATTTGTAGCC
AGTCCAACCTTTCATTCCTTGGAGGATTTAGTTTTGGGATAAAATTTTGG
TCCTTGGGCACAGAGACATTCACTATTAATGAAGTAACCCTTGGGCATGA
CTCCAATCCCAGAATTGCTCACTGAGCGCTATGCCACCGAAGCGTTGACC
TGAACATATTAGTGCAATCCAGTCCAGATTGGACCTTTGATCCTATGTGG
AAGGGCTGTTTTTTAAGAAAAAATTTTTGGTAAACAGTATTGTGTAAAAT
TGCTTTTTGTATACCAATATATGCATGTTTTGTGCATGAGTAGTACTTGT
GTTGATACTCCTGTTGATGTTAAATTACTATATAATATAAACAGTATGTG
TTTTTATATATCATTGTGTAAATTTAATATAACATATGCAGTAATAAACC
ATTTGTTTTACTGCTGTTAAGTTTGTTATTTGGGTATAAAACCAGATGTT
TACACCTGTAAAAAAAAAAAAAAAAAA

DLG (SEQ ID NO: 16)

GTGGAATCCGGCGTGGGCTGGGGGGTCCGAGCCGCGGGGGGCAGTGCCAT
GCACAAGCACCAGCACTGCTGTAAGTGCCCTGAGTGCTATGAGGTGACCC
GCCTGGCCGCCCTGCGGCGCCTCGAGCCTCCGGGCTACGGCGACTGGCAA
GTCCCCGACCCTTACGGGCCAGGTGGGGGCAACGGCGCCAGCGCGGGTTA
TGGGGGCTACAGCTCGCAGACCTTGCCCTCGCAGGCGGGGGCCACCCCCA
CCCCTCGCACCAAGGCCAAGCTCATCCCCACCGGCCGGGATGTGGGGCCG
GTGCCTCCTAAGCCAGTCCCGGGCAAGAGCACCCCCAAACTCAACGGCAG
CGGCCCCAGCTGGTGGCCAGAGTGCACCTGTACCAACCGGGACTGGTATG
AGCAGGTGAATGGCAGTGATGGCATGTTCAAATATGAGGAAATCGTACTT
GAGAGGGGCAACTCTGGCCTGGGCTTCAGTATCGCAGGTGGCATCGACAA
TCCCCATGTCCCTGATGACCCTGGCATCTTTATTACCAAGATTATCCCTG
GTGGAGCAGCTGCCATGGATGGGAGGCTGGGGGTGAATGACTGTGTGCTG
CGGGTGAATGAGGTGGACGTGTCGGAGGTGGTACACAGCCGGGCGGTGGA
GGCGCTGAAGGAGGCAGGCCCTGTGGTGCGATTGGTGGTGCGGAGGCGAC
AGCCTCCACCCGAGACCATCATGGAGGTCAACCTGCTCAAAGGGCCCAAA
GGCCTGGGTTTCAGCATTGCTGGGGGTATTGGCAACCAGCACATCCCAGG
AGACAACAGCATCTACATCACCAAGATCATTGAGGGGGGTGCTGCTCAGA
AGGATGGACGCCTACAGATTGGGGACCGGCTGCTGGCGGTGAACAACACC
AATCTGCAGGATGTGAGGCACGAGGAAGCTGTGGCCTCACTGAAGAACAC
ATCTGATATGGTGTATTTGAAGGTGGCCAAGCCAGGCAGCCTCCACCTCA
ACGACATGTACGCTCCCCCTGACTACGCCAGCACTTTTACTGCCTTGGCT
GACAACCACATAAGCCATAATTCCAGCCTGGGTTATCTCGGGGCTGTGGA
GAGCAAGGTCAGCTACCCTGCTCCTCCTCAGGTTCCCCCCACCCGCTACT
CTCCTATTCCCAGGCACATGCTGGCTGAGGAGGACTTCACCAGAGAGCCT
CGCAAGATCATCCTGCACAAAGGCTCCACAGGCCTGGGCTTCAACATCGT
AGGAGGAGAGGATGGAGAAGGCATTTTTGTCTCCTTCATCCTGGCAGGAG
GCCCAGCTGACCTGAGTGGGGAGCTGCGCAGGGGAGACCGGATCTTATCG
GTGAATGGAGTGAATCTGAGGAATGCAACTCATGAGCAGGCTGCAGCTGC
TCTGAAACGGGCCGGCCAGTCAGTCACCATTGTGGCCCAGTACAGACCTG
AAGAATACAGTCGCTTTGAATCGAAGATACATGACTTACGAGAACAAATG
ATGAACAGCAGCATGAGCTCTGGGTCTGGGTCCCTCCGAACAAGTGAAAA
GAGGTCCTTGTATGTCAGGGCCCTGTTTGATTATGATCGGACTCGGGACA
GCTGCCTGCCAAGCCAGGGGCTCAGCTTCTCTTATGGTGACATTCTGCAT
GTCATTAATGCCTCTGATGATGAGTGGTGGCAGGCAAGGCTGGTGACCCC
ACACGGAGAAAGTGAGCAGATCGGTGTGATCCCCAGTAAGAAGAGGGTGG
AAAAGAAAGAAAGAGCTCGATTGAAAACTGTGAAGTTCCATGCCAGGACG
GGGATGATTGAGTCTAACAGGGACTTCCCGGGGTTAAGTGACGATTATTA
TGGAGCAAAGAACCTGAAAGGACAAGAGGATGCTATTTTGTCATATGAGC
CAGTGACACGGCAAGAAATTCACTATGCAAGGCCTGTGATCATCCTGGGC
CCAATGAAGGACCGAGTCAATGATGACCTGATCTCCGAATTTCCACATAA
ATTTGGATCCTGTGTGCCACATACTACCCGGCCTCGACGTGATAATGAGG
TGGATGGACAAGACTACCACTTTGTGGTGTCCCGAGAACAAATGGAGAAA
GATATTCAGGACAACAAGTTCATCGAGGCGGCCAATTTAATGATAACCT
CTATGGGACCAGCATCCAGTCAGTGCGGGCAGTTGCAGAGAGGGGCAAGC
ACTGCATCTTAGATGTTTCCGGCAATGCTATCAAGAGACTGCAGCAAGCA
CAACTTTACCCCATTGCCATTTTCATCAAGCCCAAGTCCATTGAAGCCCT
TATGGAAATGAACCGAAGGCAGACATATGAACAAGCAAATAAGATCTATG

TABLE 5-continued

| ILLUSTRATIVE HUMAN DASD POLYNUCLEOTIDE SEQUENCES RETREIVED FROM GENBANK LIBRARY DATABASE USING THE DISCLOSURE IN TABLES 1-4 |
|---|
| ACAAAGCCATGAAACTGGAGCAGGAATTTGGAGAGTACTTTACAGCCATT GTACAGGGTGACTCACTGGAAGAGATTTATAACAAAATCAAACAAATCAT TGAGGACCAGTCTGGGCACTACATTTGGGTCCCATCCCCTGAAAAACTCT GAAGAATCCCCTCCAACCATTCTCTTGTGAACAGAAGAAATCAAGTCCCT CTTCCCTCCTCCCTCTTCATTCCTGTCCCCATG |

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method of identifying a test mammalian cell having a gene expression profile observed in individuals diagnosed with autism comprising:

observing an expression profile of at least one gene selected from the group consisting of SEQ ID NO: 7, SEQ ID NO:8, SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16 in the test mammalian cell;

wherein an expression profile of a gene in the group that is at least two standard deviations from a mean expression profile of the gene in a control mammalian cell obtained from an individual not affected with autism identifies the test mammalian cell as having a gene expression profile observed in individuals diagnosed with autism.

2. The method of claim 1, wherein the expression of a gene in the group is at least three, four or five standard deviations from the mean expression of the gene observed in a control mammalian cell.

3. The method of claim 1, wherein the expression level of a gene in the group is at least 20, 30, 40, 50, 60 or 70% above or below the expression level of the gene observed in the control mammalian cell.

4. The method of claim 1, wherein mRNA expression is observed.

5. The method of claim 1, wherein polypeptide expression is observed.

6. The method of claim 1, wherein the expression profile is observed using quantitative PCR (qPCR).

7. The method of claim 1, wherein the expression profile is observed using Southern blotting.

8. The method of claim 1, wherein the expression profile is observed using an antibody.

9. The method of claim 1, wherein the expression profile of the test mammalian cell is observed using a microarray of polynucleotides.

10. The method of claim 1, wherein the expression profile of the test mammalian cell is observed using a computer system comprising a processor element and a memory storage element adapted to process and store data from one or more expression profiles.

11. The method of claim 1, wherein the test mammalian cell or the control mammalian cell is a leukocyte obtained from the peripheral blood.

12. The method of claim 1, wherein the test mammalian cell is obtained from an individual previously identified as exhibiting restricted repetitive behaviors or speech delay.

13. The method of claim 1, wherein the control mammalian cell is obtained from an individual previously identified as not exhibiting restricted repetitive behaviors or speech delay.

14. The method of claim 1, wherein the test mammalian cell and the control mammalian cell are obtained from individuals who are related as siblings or as a parent and a child.

15. The method of claim 14, wherein the control mammalian cell is obtained from a male sibling unaffected by autism.

16. The method of claim 1, wherein the test mammalian cell is obtained from an individual identified as having a family member previously identified as exhibiting restricted repetitive behaviors or speech delay.

17. The method of claim 1, wherein an expression profile of at least, 2, 3, 4, 5, 6, 7, 8, 9 or 10 genes in the group are observed.

* * * * *